US008809329B2

(12) United States Patent
Itokawa et al.

(10) Patent No.: US 8,809,329 B2
(45) Date of Patent: Aug. 19, 2014

(54) DETECTION AND TREATMENT OF SCHIZOPHRENIA

(75) Inventors: Masanari Itokawa, Tokyo (JP); Toshio Miyata, Kanagawa (JP); Makoto Arai, Tokyo (JP)

(73) Assignees: Tokyo Metropolitan Institute of Medical Science, Tokyo (JP); Renascience Co., Ltd., Tokyo (JP)

( * ) Notice: Subject to any disclaimer, the term of this patent is extended or adjusted under 35 U.S.C. 154(b) by 238 days.

(21) Appl. No.: 12/674,018

(22) PCT Filed: Jul. 31, 2008

(86) PCT No.: PCT/JP2008/063803
§ 371 (c)(1),
(2), (4) Date: Feb. 18, 2010

(87) PCT Pub. No.: WO2009/025159
PCT Pub. Date: Feb. 26, 2009

(65) Prior Publication Data
US 2011/0028470 A1 Feb. 3, 2011
US 2012/0065198 A2 Mar. 15, 2012

(30) Foreign Application Priority Data
Aug. 20, 2007 (JP) .................................. 2007-214047

(51) Int. Cl.
A61K 31/5355 (2006.01)
A61P 25/18 (2006.01)
A61K 31/4152 (2006.01)
A61K 31/4355 (2006.01)
A61K 31/4155 (2006.01)
A61K 31/416 (2006.01)
A61K 31/4709 (2006.01)
A61K 31/44 (2006.01)
A61K 31/427 (2006.01)

(52) U.S. Cl.
USPC ........ 514/232.2; 514/351; 514/404; 514/371; 514/381; 514/405; 514/312; 514/302

(58) Field of Classification Search
USPC .............. 514/232.2, 351, 404, 371, 381, 405, 514/312, 302
See application file for complete search history.

(56) References Cited

U.S. PATENT DOCUMENTS

| 7,645,882 B2 | 1/2010 | Miyata et al. | |
| 2003/0157548 A1 | 8/2003 | Nawa et al. | |
| 2004/0241685 A1 | 12/2004 | Nawa et al. | |
| 2005/0009779 A1* | 1/2005 | Kiliaan et al. | 514/52 |
| 2005/0164400 A1 | 7/2005 | Hashimoto et al. | |
| 2005/0249823 A1 | 11/2005 | Murphy et al. | |
| 2010/0137635 A1 | 6/2010 | Natori et al. | |

FOREIGN PATENT DOCUMENTS

| EP | 1 420 068 | 5/2004 |
| EP | 1693369 A1 | 8/2006 |
| JP | 52102431 A | 8/1977 |
| JP | 2001245661 | 9/2001 |
| JP | 200338198 | 2/2003 |
| JP | 2003212795 | 7/2003 |
| JP | 2004251865 | 9/2004 |
| JP | 200555227 | 3/2005 |
| JP | 2005278490 | 10/2005 |
| WO | 02/061065 | 8/2002 |
| WO | 2004005935 | 1/2004 |
| WO | 2006132205 A1 | 12/2006 |

OTHER PUBLICATIONS

Wolff, Manfred E. "Burger's Medicinal Chemistry, 5ed, Part I", John Wiley & Sons, 1995, pp. 975-977.*
Voziyan, P.A. et al, Pyridoxamine as a multifunctional pharmaceutical: targeting pathogenic glycation and oxidative damage, Cellular and Molecular Life Sciences, vol. 62, No. 15, Aug. 2005, pp. 1671-1681.
Reedy, R. et al., Peripheral oxyradical scavenging enzymes in Schizophrenia, Biological Psychiatry, Elseview Science, May 1, 1990, p. 106A, Abstract 144.
Prabakaran, S. et al., Mitochondrial dysfunction in schizophrenia: evidence for compromised brain metabolism and oxidative stress, Molecular Psychiatry, vol. 9, No. 7, Jul. 1, 2004, pp. 684-697.
Ozyurt et al, A preliminary study of the levels of testis oxidative stress parameters after MK-801-induced experimental psychosis model: Protective effects of CAPE, Toxicology, vol. 230, No. 1, Jan. 12, 2007, pp. 83-89.
ESR dated Jul. 14, 2010 for EP application No. 08792016.

(Continued)

*Primary Examiner* — San-Ming Hui
*Assistant Examiner* — Kathrien Cruz
(74) *Attorney, Agent, or Firm* — Roylance, Abrams, Berdo & Goodman, L.L.P.

(57) ABSTRACT

The present invention provides a method for diagnosing schizophrenia, and a schizophrenia diagnostic reagent or device for use in the method. The present invention further provides a therapeutic or ameliorating agent for schizophrenia, which is effective for the treatment or amelioration of schizophrenia. The therapeutic or ameliorating agent for schizophrenia contains a carbonyl scavenger or a carbonyl-modified protein formation inhibitor as an active ingredient. The method for diagnosing schizophrenia according to the present invention includes measuring at least one parameter in a subject, the parameter being selected from the group consisting of: (1) a genetic abnormality of glyoxalase I gene; (2) the expression level or activity of glyoxalase I in a biological sample; (3) the amount of a carbonyl compound or a carbonyl-modified protein that is a protein modified with the carbonyl compound; and (4) the amount of pyridoxal in a biological sample.

12 Claims, 11 Drawing Sheets

(56) References Cited

OTHER PUBLICATIONS

Turner et al., Genetic markers for schizotaxia., Biol. Psychiatry, 1979, vol. 14, No. 1, p. 177-206.

Young, J. et al., Biomarkers of oxidative stress in schizophrenic and control subjects, Prostaglandings, Leukotrienes and Essential Fatty Acids, 2007, vol. 76, No. 2, pp. 73-85.

Sugiyama, S. et al., Plasma levels of pentosidine in diabetic patients: an advanced glycation end product, Journal of the American Society of Nephrology, 1998, vol. 9, No. 9, pp. 1681-1688.

Tsukahara, H. et al., High levels of urinary pentosidine, an advanced glycation end product, in children with acute exacerbation of atopic dermatitis: relationship with oxidative stress, Metabolism, 2003, vol. 52, No. 12, pp. 1601-1605.

Partial European Search Report dated Sep. 23, 2013 for EP Patent Application No. 13003496.0.

Levine, J. et al., Homocysteine-reducing strategies improve symptoms in chronic schizophrenic patients with hyperhomocysteinemia, Biol. Psychiatry, 2006, 60 (3), pp. 265-269.

Seikagaku Jiten, the 3rd edition, 1998, p. 1105.

Turner et al., Genetic markers for schizotaxia., Biol. Psychiatry, 1979, vol. 14, No. 1, p. 117-206.

Gale et al., Common polymorphisms in the glyoxalase-1 gene and their association with pro-thrombotic factors, Diab. Vasa. Dis. Res., 2004, vol. 1, No. 1, p. 34-39.

Miyata et al., Glyoxalase I deficiency is associated with an unusual level of advanced glycation end products in a hemodialysis patient, Kidney Int., 2001, vol. 60, No. 6, p. 2351-2359.

Politi et al., Association analysis of the functional Ala111Glu polymorphism of the glyoxalase I gene in panic disorder. Neurosci. Lett., 2006, vol. 396, No. 2, p. 163-166.

Sacco et al., Case-control and family-based association studies of candidate genes in autistic disorder and its endophenotypes: TPH2 and GL01. BMC Med. Genet. 2007, vol. 8:11, 9 pages.

McGlashan et a., A selective review of recent North American long-term followup studies of schizophrenia. Schizophr. Bull., 1988, vol. 14, No. 4, 515-542.

\* cited by examiner

Fig. 1

|   | Diagnostic Criteria for Schizophrenia as Outlined by "International Classification of Diseases, Tenth Revision" (ICD-10) |
|---|---|
| (a) | thought echo, thought insertion or withdrawal, and thought broadcasting; |
| (b) | delusions of control, influence, or passivity, clearly referred to body or limb movements or specific thoughts, actions, or sensations; delusional perception; |
| (c) | hallucinatory voices giving a running commentary on the patient's behaviour, or discussing the patient among themselves, or other types of hallucinatory voices coming from some part of the body; |
| (d) | persistent delusions of other kinds that are culturally inappropriate and completely impossible, such as religious or political identity, or superhuman powers and abilities (e.g. being able to control the weather, or being in communication with aliens from another world); |
| (e) | persistent hallucinations in any modality, when accompanied either by fleeting or half-formed delusions without clear affective content, or by persistent over-valued ideas, or when occurring every day for weeks or months on end; |
| (f) | breaks or interpolations in the train of thought, resulting in incoherence or irrelevant speech, or neologisms; |
| (g) | catatonic behaviour, such as excitement, posturing, or waxy flexibility, negativism, mutism, and stupor; |
| (h) | "negative" symptoms such as marked apathy, paucity of speech, and blunting or incongruity of emotional responses, usually resulting in social withdrawal and lowering of social performance; it must be clear that these are not due to depression or to neuroleptic medication; |
| (i) | a significant and consistent change in the overall quality of some aspects of personal behaviour, manifest as loss of interest, aimlessness, idleness, a self-absorbed attitude, and social withdrawal. |

Diagnostic Guidelines
The normal requirement for a diagnosis of schizophrenia is that a minimum of one very clear symptom (and usually two or more if less clear-cut) belonging to any one of the groups listed as (a) to (d) above, or symptoms from at least two of the groups referred to as (e) to (h), should have been clearly present for most of the time during a period of 1 month or more.

Fig. 2

Diagnostic Criteria for Schizophrenia as Outlined by DSM-IV

A. Characteristic symptoms: Two (or more) of the following, each present for a significant portion of time during a 1-month period (or less if successfully treated):

( 1 )    delusions ( 2 )    hallucinations ( 3 )    disorganized speech (e.g., frequent derailment or incoherence)

( 4 )    grossly disorganized or catatonic behavior ( 5 )    negative symptoms, i.e., affective flattening, alogia, or avolition Note: Only one Criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder exclusion: Schizoaffective Disorder and Mood Disorder with Psychotic Features have been ruled out because either ( 1 )    no Major Depressive Episode, Manic Episode, or Mixed Episode have occurred concurrently with the active-phase symptoms; or ( 2 )    if mood episodes have occurred during active-phase symptoms, their total duration has been brief relative to the duration of the active and residual periods.

E. Substance/general medical condition exclusion: The disturbance is not due to the direct physiological effects of a substance (e.g., a drug of abuse, a medication) or a general medical condition.

F. Relationship to a Pervasive Developmental Disorder: If there is a history of Autistic Disorder or another Pervasive Developmental Disorder, the additional diagnosis of Schizophrenia is made only if prominent delusions or hallucinations are also present for at least a month (or less if successfully treated).

Fig. 3

Therapeutic Agent for Schizophrenia

| Drug Name | Volume (mg/day) |
|---|---|
| Typical Antipsychotic Drugs (Conventional) | |
|   Butyrophenones | |
|     Haloperidol | 0.75 – 6 |
|     Pipamperone | 50 – 600 |
|     Spiperone | 0.45 – 4.5 |
|     Moperone | 10 – 30 |
|     Pimozide | 1 – 9 |
|     Timiperone | 0.5 – 12 |
|     Bromperidol | 3 – 36 |
|   Phenothiazines | |
|     Chlorpromazine | 30 – 450 |
|     Levomepromazine | 25 – 200 |
|     Thioridazine | 30 – 400 |
|     Propericyazine | 10 – 60 |
|     Perphenazine | 6 – 48 |
|     Fluphenazine | 0.25 – 10 |
|     Prochlorperazine | 15 – 45 |
|     Trifluoperazine | 5 – 30 |
|   Benzamides | |
|     Sulpiride | 150 – 600 |
|     Sultopride | 300 – 1800 |
|     Nemonapride | 9 – 60 |
|   Thiepines | |
|     Zotepine | 75 – 450 |
|   Indoles | |
|     Oxypertine | 40 – 300 |
|   Iminodibenzyls | |
|     Carpipramine | 75 – 225 |
|     Clocapramine | 30 – 150 |
|     Mosapramine | 30 – 300 |
| Atypical Antipsychotic Drugs | |
|   SDA | |
|     Risperidone | 2 – 8 |
|     Perospirone | 12 – 48 |
|   Dibenzothiazepines | |
|     Quetiapine | 50 – 750 |
|   MARTA | |
|     Olanzapine | 5 – 20 |

Activity of glyoxalase I  mU/million red blood cells

Fig. 5
A
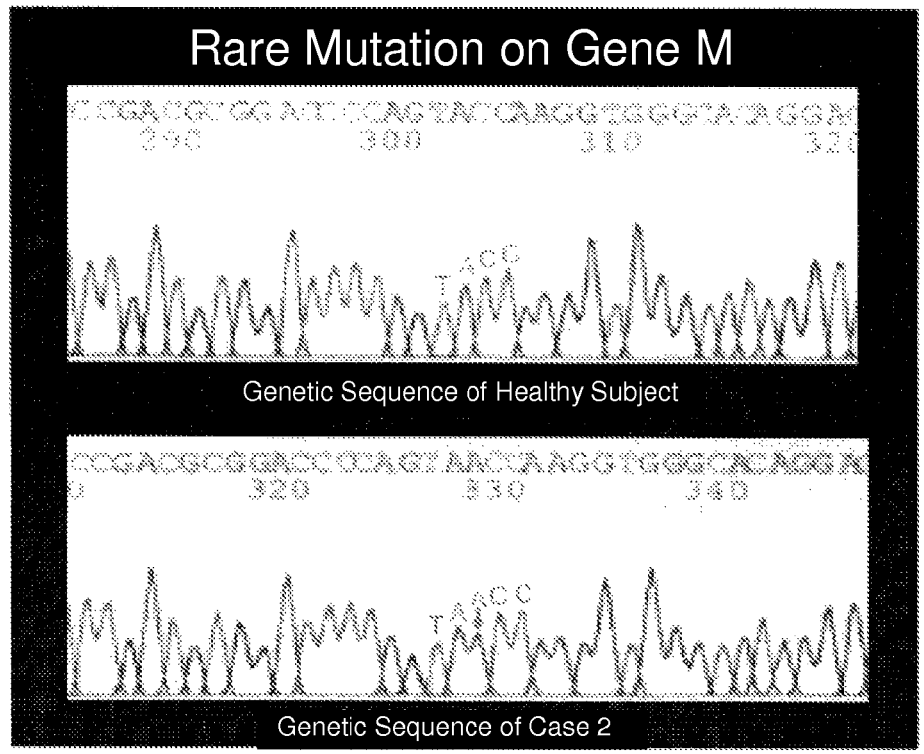
B
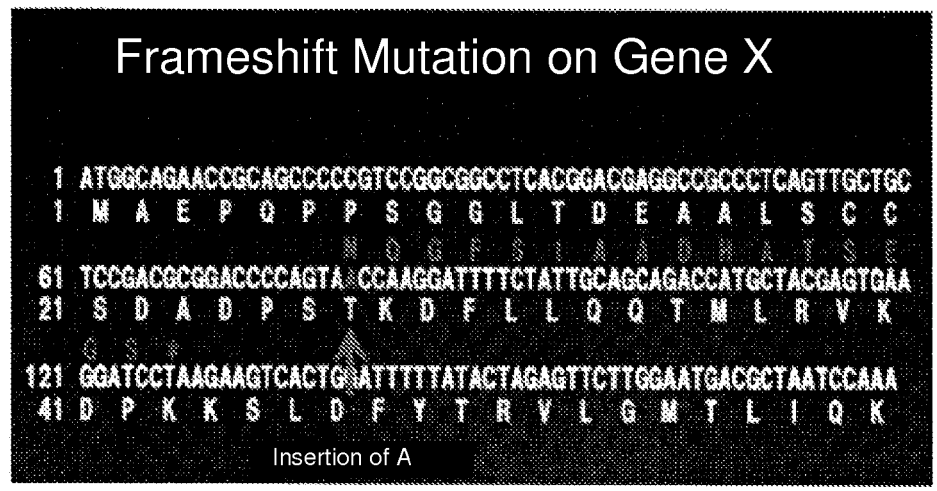

Fig. 8
A
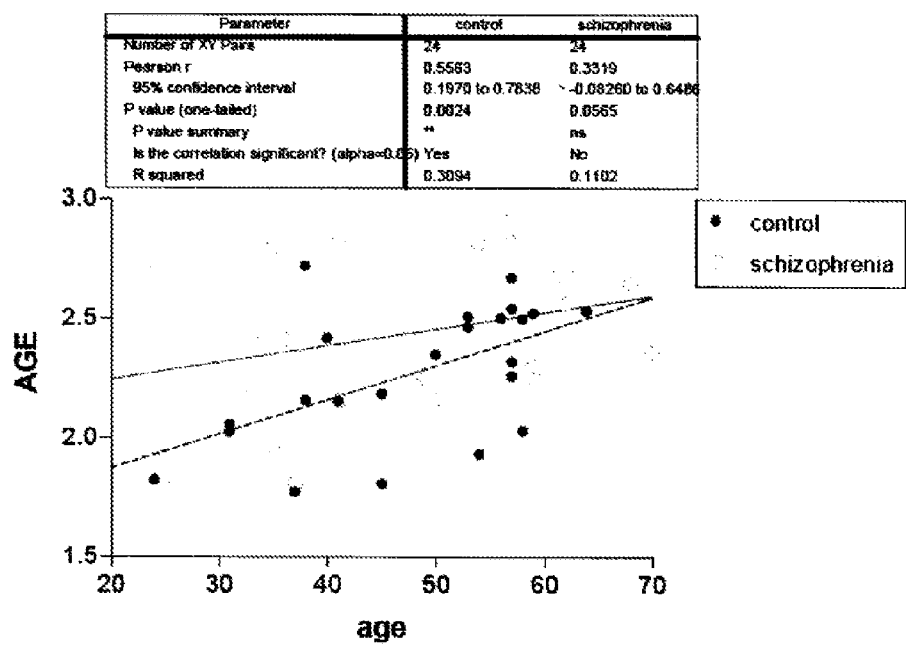
B
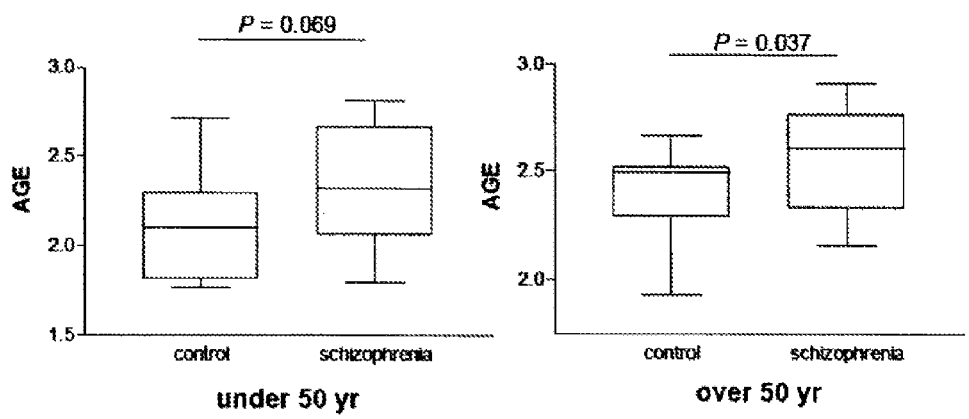

Fig. 12

| Reference Level | | | | Glyoxalase I Activity | | Pentosidine (nmol/in g) | M 6.0-20.0 F 4.0-19.0 | M 0.6 or less F 0.6 or less | M 3.0 or less F 3.0 or less | 180-914 | 3.1 or more | 3.7-13.5 | M 0.61-1.04 F 0.47-0.79 | | |
|---|---|---|---|---|---|---|---|---|---|---|---|---|---|---|---|
| Group | Name | Age | Sex | Activity $ (mUnit/10⁶ RBC) | Based on Healthy Subjects as 100 (%) | | Vitamin B6 (ng/ml) | | | Vitamin B12 (pg/ml) | Folate (ng/ml) | Homocysteine (nmol/l) | Creatinine (mg/dl) | eGFR (ml/min/1.73m²) | Diabetic or Not |
| | | | | | | | Pyridoxal | Pyridoxamine | Pyridoxine | | | | | | |
| Patient — Frameshift Case | MZ-70 | 60 | Male | 2.8 | 45 | 5.4 | 2.8 | 0.2 or less | 3.0 or less | 442 | 2.9 | 26.5 | 1.05 | 53.4 | · |
| | NP-50 | 60 | Female | 3.0 | 48 | 3.2 | 2.0 or less | 0.2 or less | 3.0 or less | 327 | 5.9 | 15.4 | 0.82 | 52.7 | · |
| | mean | | | 2.9 | 47 | 4.3 | 2.5 | | | 385 | 4.4 | 21.0 | 0.9 | 53.1 | |
| | SD | | | 0.1 | 2.3 | 1.6 | 0.5 | | | 81 | 2.1 | 7.8 | 0.2 | 0.5 | |
| Patient — A/a/Ab Type | TZ-61 | 50 | Female | 4.3 | 69 | 4.2 | 7.5 | 0.2 or less | 3.0 or less | | | 10.5 | 0.57 | 83.2 | · |
| | MZ-65 | 66 | Male | 4.2 | 68 | 10.4 | 7.3 | 0.2 or less | 3.0 or less | | | 9.9 | 0.86 | 65.9 | · |
| | MZ-86 | 50 | Male | 4.3 | 69 | 3.2 | 3.6 | 0.2 or less | 3.0 or less | 391 | 2.4 | 23.7 | 0.72 | 85.6 | · |
| | NP-85 | 72 | Female | 4.9 | 79 | 2.4 | 15.6 | 0.2 or less | 3.0 or less | 349 | 6.0 | 15.1 | 0.57 | 77.3 | · |
| | NP-300 | 52 | Male | 4.5 | 73 | 2.5 | 9 | | | 370 | 4.2 | 46.9 | 0.67 | 92.3 | · |
| | mean | | | 4.4 | 72 | 4.5 | 8.6 | | | | | 21.2 | 0.7 | 80.9 | |
| | SD | | | 0.3 | 5 | 3.4 | 4.4 | | | 30 | 2.5 | 15.4 | 0.1 | 9.9 | |
| Patient — G U/A/a Type | MZ-179 | 63 | Male | 5.3 | 85 | 2.2 | 5.6 | 0.2 or less | 3.0 or less | 419 | 3.3 | 9.9 | 0.75 | 77.9 | · |
| Healthy Subjects | IT | 45 | Male | 5.9 | | 1.9 | 14.6 | 0.2 or less | 3.0 or less | | 5.7 | 12.6 | 0.88 | 65.9 | · |
| | HA | 58 | Male | 5.9 | | 2.0 | | 0.2 or less | 3.0 or less | 330 | | 8.9 | 0.76 | 59.5 | · |
| | YU | 51 | Female | 6.8 | | 1.8 | 14.1 | 0.2 or less | 3.0 or less | 247 | 4.1 | 9.8 | 0.90 | 73.9 | · |
| | TA | 29 | Male | 5.7 | | 1.2 | 5.5 | 0.2 or less | 3.0 or less | 451 | 9.2 | 13.7 | 0.60 | 80.8 | · |
| | IZ | 43 | Female | 6.0 | | 1.5 | | | | | | 8.8 | | | · |
| | KA | | | 7.0 | | 2.0 | 7.2 | | 3.0 or less | | | 11.6 | 0.80 | 85.3 | · |
| | W | 28 | Male | 6.2 | | 1.0 | 10.4 | 0.2 or less | | | | 10.9 | 0.8 | 73.1 | · |
| | mean | | | 6.2 | | 1.6 | | | | 343 | 6.3 | 10.9 | 0.8 | 73.1 | |
| | SD | | | 0.5 | | 0.4 | 4.7 | | | 103 | 2.6 | 2.0 | 0.1 | 10.6 | |

$ Calculated based on 10% hematocrit as 0.6 × 10⁹

SEQUENCE LISTING

```
<160> NUMBER OF SEQ ID NOS: 11

<210> SEQ ID NO 1
<211> LENGTH: 2071
<212> TYPE: DNA
<213> ORGANISM: Homo sapiens
<220> FEATURE:
<221> NAME/KEY: CDS
<222> LOCATION: (123)..(674)

<400> SEQUENCE: 1
agcggtctcc cgcccgcggc gccatcgcgc cattcctagt taaggcggca cagggccgag      60
gcgtagtgtg ggtgactcct ccgttccttg ggtcccgtcg tctgtgatac tgcagcgcag     120 cc atg gca gaa ccg cag ccc ccg tcc ggc ggc ctc acg gac gag gcc       167
   Met Ala Glu Pro Gln Pro Pro Ser Gly Gly Leu Thr Asp Glu Ala
```

```
              1               5              10              15
gcc ctc agt tgc tgc tcc gac gcg gac ccc agt acc aag gat ttt cta    215
Ala Leu Ser Cys Cys Ser Asp Ala Asp Pro Ser Thr Lys Asp Phe Leu
                    20                  25                  30 ttg cag cag acc atg cta cga gtg aag gat cct aag aag tca ctg gat    263
Leu Gln Gln Thr Met Leu Arg Val Lys Asp Pro Lys Lys Ser Leu Asp
                35                  40                  45 ttt tat act aga gtt ctt gga atg acg cta atc caa aaa tgt gat ttt    311
Phe Tyr Thr Arg Val Leu Gly Met Thr Leu Ile Gln Lys Cys Asp Phe
            50                  55                  60 ccc att atg aag ttt tca ctc tac ttc ttg gct tat gag gat aaa aat    359
Pro Ile Met Lys Phe Ser Leu Tyr Phe Leu Ala Tyr Glu Asp Lys Asn
        65                  70                  75 gac atc cct aaa gaa aaa gat gaa aaa ata gcc tgg gcg ctc tcc aga    407
Asp Ile Pro Lys Glu Lys Asp Glu Lys Ile Ala Trp Ala Leu Ser Arg
80                  85                  90                  95 aaa gct aca ctt gag ctg aca cac aat tgg ggc act gaa gat gat gag    455
Lys Ala Thr Leu Glu Leu Thr His Asn Trp Gly Thr Glu Asp Asp Glu
                    100                 105                 110 acc cag agt tac cac aat ggc aat tca gac cct cga gga ttc ggt cat    503
Thr Gln Ser Tyr His Asn Gly Asn Ser Asp Pro Arg Gly Phe Gly His
                115                 120                 125 att gga att gct gtt cct gat gta tac agt gct tgt aaa agg ttt gaa    551
Ile Gly Ile Ala Val Pro Asp Val Tyr Ser Ala Cys Lys Arg Phe Glu
            130                 135                 140 gaa ctg gga gtc aaa ttt gtg aag aaa cct gat gat ggt aaa atg aaa    599
Glu Leu Gly Val Lys Phe Val Lys Lys Pro Asp Asp Gly Lys Met Lys
        145                 150                 155 ggc ctg gca ttt att caa gat cct gat ggc tac tgg att gaa att ttg    647
Gly Leu Ala Phe Ile Gln Asp Pro Asp Gly Tyr Trp Ile Glu Ile Leu
160                 165                 170                 175 aat cct aac aaa atg gca acc tta atg tagtgctgtg agaattctcc           694
Asn Pro Asn Lys Met Ala Thr Leu Met
                180 tttgagattt cagaagaaag gaaacaatgt gattcaagat atttacatac cagaagcatc   754 taggactgat ggatcactgt cccgattcaa attattcttc agtccatttc cccttcctat   814 ttcagctgtt cctttttcacc taactgttca gtcattctgg ttttcaagca gtgctttatc  874 tcatgtcctt gaatatagtt gtgtaacttt attttttagg taataattag aacagttccc   934 ttcagaggct gcatttgcct tcttctgcca cctaaatatt acttcccttc aaatctgcct   994 ttgaatcatc atttttaaaa aaaaattaac atgttttttgt tgtagttatc ttctggggtt  1054 tcaattcctc agaaacaact tttttcacaa cggaaaggaa agaacactag tgttctttca   1114 gtaaagtaca aagtgtttat tttacaaaag agtaggtact cttgagagca attcaaatca   1174 tgctgacaag gatactgata gaaaaagtga tttcttctta ttataaagta catttaaagt   1234 tcaaggacta accttattta tttgggaaag gggaggagga aggaaatgat atggtaccca   1294 gacactgggc taggctgcaa ctttatctca tttaatactc ccagctgtca tgtgagaaag   1354 aaagcaggct aggcatgtga atcactttc atggattatt aatggattta agagggcatc    1414 aatcagctca actcaagatt tcataatcat tttagtatt tagattgtgc ctcaaagttg    1474 tagtacctca caatacctcc actggtttcc tgttgtaaaa accttcagtg agtttgacca   1534 ttgtgctctt ggctcttggg ctggagtacc gtggtgaggg agtaaacact agaagtcttt   1594 agtacaaaac tgctctaggg acacctggtg attcctacac aagtgatgtt tatatttctc   1654 ataaagagtc ttccctatcc caaggtcttc atgatgccag tagccatata tgataaatta   1714
```

```
tgttcagtga taacttagtt atcagaaatc agctcagtgg tcttccccgc catgattcac    1774
atttgatgag tttttaaaaa tcaaagtgat tttgaaaatc tctaatggct cagaaaataa    1834
aaacatccag tttgtggatg actatattta gatttctcta gactctagtg aagacctttt    1894
ggaaaggcca tgccaaccgt gcttgtactg ctagaagcac tttatgtttc ctttttgggt    1954
gaaatggatt tatgtgagtg ctttaaacaa atagcaatac ttatagactg aaataaaatg    2014
aaacttcaaa taagactatg tttaatttgt aaaaaaaaaa aaaaaaaaaa aaaaaaa      2071
```

<210> SEQ ID NO 2
<211> LENGTH: 552
<212> TYPE: DNA
<213> ORGANISM: Homo sapiens

<400> SEQUENCE: 2

```
atggcagaac cgcagccccc gtccggcggc ctcacggacg aggccgccct cagttgctgc     60
tccgacgcgg accccagtac caaggatttt ctattgcagc agaccatgct acgagtgaag    120
gatcctaaga agtcactgga tttttatact agagttcttg gaatgacgct aatccaaaaa    180
tgtgattttc ccattatgaa gttttcactc tacttcttgg cttatgagga taaaaatgac    240
atccctaaag aaaagatgaa aaaatagcc tgggcgctct ccagaaaagc tacacttgag    300
ctgacacaca ttggggcac tgaagatgat gagacccaga gttaccacaa tggcaattca    360
gaccctcgag gattcggtca tattggaatt gctgttcctg atgtatacag tgcttgtaaa    420
aggtttgaag aactgggagt caaatttgtg aagaaacctg atgatggtaa atgaaaggc    480 ctggcattta ttcaagatcc tgatggctac tggattgaaa ttttgaatcc taacaaaatg    540
gcaaccttaa tg                                                        552
```

<210> SEQ ID NO 3
<211> LENGTH: 184
<212> TYPE: PRT
<213> ORGANISM: Homo sapiens

<400> SEQUENCE: 3

```
Met Ala Glu Pro Gln Pro Pro Ser Gly Gly Leu Thr Asp Glu Ala Ala
1               5                   10                  15

Leu Ser Cys Cys Ser Asp Ala Asp Pro Ser Thr Lys Asp Phe Leu Leu
            20                  25                  30

Gln Gln Thr Met Leu Arg Val Lys Asp Pro Lys Lys Ser Leu Asp Phe
        35                  40                  45

Tyr Thr Arg Val Leu Gly Met Thr Leu Ile Gln Lys Cys Asp Phe Pro
    50                  55                  60

Ile Met Lys Phe Ser Leu Tyr Phe Leu Ala Tyr Glu Asp Lys Asn Asp
65                  70                  75                  80

Ile Pro Lys Glu Lys Asp Glu Lys Ile Ala Trp Ala Leu Ser Arg Lys
                85                  90                  95

Ala Thr Leu Glu Leu Thr His Asn Trp Gly Thr Glu Asp Asp Glu Thr
            100                 105                 110

Gln Ser Tyr His Asn Gly Asn Ser Asp Pro Arg Gly Phe Gly His Ile
        115                 120                 125

Gly Ile Ala Val Pro Asp Val Tyr Ser Ala Cys Lys Arg Phe Glu Glu
    130                 135                 140

Leu Gly Val Lys Phe Val Lys Pro Asp Asp Gly Lys Met Lys Gly
145                 150                 155                 160
```

Leu Ala Phe Ile Gln Asp Pro Asp Gly Tyr Trp Ile Glu Ile Leu Asn
            165                 170                 175

Pro Asn Lys Met Ala Thr Leu Met
            180

<210> SEQ ID NO 4
<211> LENGTH: 200
<212> TYPE: DNA
<213> ORGANISM: Artificial Sequence
<220> FEATURE:
<223> OTHER INFORMATION: Upstream sequence (1-200) of adenine in 201
      position of base sequence of Glyoxalase I gene (SEQ:No.1)

<400> SEQUENCE: 4
agcggtctcc cgcccgcggc gccatcgcgc cattcctagt taaggcggca cagggccgag      60
gcgtagtgtg ggtgactcct ccgttccttg ggtcccgtcg tctgtgatac tgcagcgcag     120
ccatggcaga accgcagccc cgtccggcg gcctcacgga cgaggccgcc ctcagttgct     180
gctccgacgc ggaccccagt                                                 200

<210> SEQ ID NO 5
<211> LENGTH: 300
<212> TYPE: DNA
<213> ORGANISM: Artificial Sequence
<220> FEATURE:
<223> OTHER INFORMATION: Downstream sequence (203-502) of cytosine in
      202 position of base sequence of Glyoxalase I gene (SEQ:No.1)

<400> SEQUENCE: 5
caaggatttt ctattgcagc agaccatgct acgagtgaag gatcctaaga agtcactgga      60
tttttatact agagttcttg gaatgacgct aatccaaaaa tgtgattttc ccattatgaa     120
gttttcactc tacttcttgg cttatgagga taaaaatgac atccctaaag aaaagatga     180 aaaaatagcc tgggcgctct ccagaaaagc tacacttgag ctgacacaca attggggcac     240
tgaagatgat gagacccaga gttaccacaa tggcaattca ccctcgagg attcggtca     300

<210> SEQ ID NO 6
<211> LENGTH: 300
<212> TYPE: DNA
<213> ORGANISM: Artificial Sequence
<220> FEATURE:
<223> OTHER INFORMATION: Upstream sequence (154-453) of adenine in 454
      position of base sequence of Glyoxalase I gene (SEQ:No.1)

<400> SEQUENCE: 6
tcacggacga ggccgccctc agttgctgct ccgacgcgga ccccagtacc aaggattttc      60
tattgcagca gaccatgcta cgagtgaagg atcctaagaa gtcactggat ttttatacta     120
gagttcttgg aatgacgcta atccaaaaat gtgattttcc cattatgaag ttttcactct     180
acttcttggc ttatgaggat aaaaatgaca tccctaaaga aaagatgaa aaaatagcct     240 gggcgctctc cagaaaagct acacttgagc tgacacacaa ttggggcact gaagatgatg     300

<210> SEQ ID NO 7
<211> LENGTH: 300
<212> TYPE: DNA
<213> ORGANISM: Artificial Sequence
<220> FEATURE:
<223> OTHER INFORMATION: Downstream sequence (455-754) of adenine in
      454 position of base sequence of Glyoxalase I gene (SEQ:No.1)

<400> SEQUENCE: 7
gacccagagt taccacaatg gcaattcaga ccctcgagga ttcggtcata ttggaattgc      60

```
tgttcctgat gtatacagtg cttgtaaaag gtttgaagaa ctgggagtca aatttgtgaa      120
gaaacctgat gatggtaaaa tgaaaggcct ggcatttatt caagatcctg atggctactg      180
gattgaaatt ttgaatccta acaaaatggc aaccttaatg tagtgctgtg agaattctcc      240
tttgagattt cagaagaaag gaaacaatgt gattcaagat atttacatac cagaagcatc      300

<210> SEQ ID NO 8
<211> LENGTH: 20
<212> TYPE: DNA
<213> ORGANISM: Artificial Sequence
<220> FEATURE:
<223> OTHER INFORMATION: Forward primer for PCR-direction sequence

<400> SEQUENCE: 8
gagtttgcct cctttatgcg                                                   20

<210> SEQ ID NO 9
<211> LENGTH: 20
<212> TYPE: DNA
<213> ORGANISM: Artificial Sequence
<220> FEATURE:
<223> OTHER INFORMATION: Reverse primer for PCR-direction sequence

<400> SEQUENCE: 9
aacagatccc ctccacactt                                                   20

<210> SEQ ID NO 10
<211> LENGTH: 20
<212> TYPE: DNA
<213> ORGANISM: Artificial Sequence
<220> FEATURE:
<223> OTHER INFORMATION: Forward primer for PCR-direction sequence

<400> SEQUENCE: 10
tcagagtgtg tgatttcgtg                                                   20

<210> SEQ ID NO 11
<211> LENGTH: 20
<212> TYPE: DNA
<213> ORGANISM: Artificial Sequence
<220> FEATURE:
<223> OTHER INFORMATION: Reverse primer for PCR-direction sequence

<400> SEQUENCE: 11
catggtgaga tggtaagtgt                                                   20
```

DETECTION AND TREATMENT OF SCHIZOPHRENIA

TECHNICAL FIELD

The present invention provides a method for diagnosing schizophrenia, and a schizophrenia diagnostic reagent or device for use in the method. The present invention further provides a therapeutic or ameliorating agent for schizophrenia, which is effective for the treatment or amelioration of schizophrenia.

BACKGROUND ART

"Integration dysfunction syndrome" (schizophrenia), formerly called "mind-split-disease", is a typical psychiatric disorder characterized by hallucinations and delusions. Schizophrenia affects about 1% of the population, and 700,000 people are currently under treatment for schizophrenia in Japan. Late adolescence and early adulthood from the ages of 17 to 27 are the peak years for the onset of schizophrenia, and the disorder becomes chronic after those ages. Therefore, in 1996, patients with schizophrenia occupied 22% of all hospital beds. The peak years for males for the onset of this disorder are the ages of from 15 to 24, whereas the peak years for females for the onset of the same are the ages of from 25 to 34; thus, the onset in women is late. Furthermore, since menopause is another peak age for the onset of schizophrenia, female sex hormones are sometimes said to have an inhibitory effect on the pathological conditions associated with schizophrenia. However, the detailed reasons for this are still unknown. As described later herein, only symptomatic medication is used for the main treatment, and no decisive therapeutic method has yet to be established.

The involvement of a genetic factor in the onset of schizophrenia is suggested by the fact that the simultaneous onset of schizophrenia in identical twins is 35 to 58%, which is higher than that of fraternal twins, i.e., 13 to 27%. The heritability is estimated to be about 80%. Even compared with the heritability of hypertension, which is 30%, and the heritability of obesity, which is 40 to 70%, the influence of hereditary factors on schizophrenia is great. For this reason, many candidate genes have been studied since the 1990s, and the number of genes studied so far has reached the triple digits. Further, a large-scale linkage study has also been performed. Although several candidate genes have been identified by positional approaches, the pathological conditions are still inexplicable in terms of biochemistry etc. Moreover, the results of the candidate gene analyses of various researchers are inconsistent. Therefore, schizophrenia is not considered to be a so-called "hereditary disease" (monogenic disease), but rather a multifactorial genetic disease that is developed by a combination of a plurality of genes having low pathogenic effects, and environmental factors.

The main symptoms of schizophrenia are positive symptoms prominently observed during the acute phase (e.g., hallucinations, delusions, and incoherence), and negative symptoms that become prominent during the chronic phase (e.g., apathy, lack of emotion and motivation, and social withdrawal).

Diagnosis of schizophrenia is currently made based on interviews with the patient in consideration of the patient's remarks and facial expressions, sometimes with additional information from the family, according to one of the following criteria: the "International Classification of Diseases, Tenth Revision" (ICD-10) of the World Health Organization (WHO) (see FIG. 1), or the "Diagnostic and Statistical Manual, Fourth Edition" (DSM-IV) of the American Psychiatric Association (APA) (see FIG. 2). Accordingly, a final diagnosis inevitably depends on the doctor's personal opinion, based on his experience. Thus, diagnoses are not always sufficiently accurate. Therefore, the chromosomal mapping of the gene that causes schizophrenia and the identification thereof, and research using biological samples such as patient's blood or urine have been actively carried out. As a result, several biological markers that can be used for the diagnosis of schizophrenia have been reported (see Patent Documents 1 to 7). However, no decisive method has yet to be established.

The main treatment of schizophrenia is the administration of an antipsychotic (see FIG. 3). The administration must be continued almost throughout a person's entire life. The pharmacological effects of antipsychotics on hallucinations and delusions are based on dopamine receptor blocking activity. However, since the inhibition of dopamine neurons causes Parkinsonian symptoms as side effects, an anti-Parkinson's agent is generally used with the antipsychotic. In recent years, in place of conventional antipsychotics, which are effective for positive symptoms of schizophrenia but substantially ineffective for negative symptoms thereof, atypical antipsychotics that are also effective for the negative symptoms have been developed and used. Compared to conventional antipsychotics, such atypical antipsychotics have weak blocking effects on dopamine receptors, and are thus advantageous in terms of decreased side effects such as Parkinson's symptoms.

Examples of therapeutic methods other than administration of an antipsychotic include electroconvulsive therapy (ECT), which is a therapeutic method in which a general convulsion is induced by applying an alternating current of 100V for 5 seconds; and psychiatric rehabilitation, in which social skills training (SST) and occupational therapies such as farming, woodworking, handicrafts, and recreation are carried out. ECT, mentioned above as the first example, is used when immediate improvement of the condition is required, for example, in the case of immediate suicide risk, malnutrition, or catatonia, or when patients are resistant to pharmaceutical treatment. Psychiatric rehabilitation, mentioned as the second example, is used to acquire life skills and thus reduce stress in social life, thereby preventing recurrences.

However, these methods are all symptomatic treatments. Although the data is old, the results of a 15-year follow-up study of schizophrenia conducted using, as subjects, chronic intractable patients for whom drug treatment was ineffective are as follows: 6% recovered; 8% were good; 23% were moderate; 23% were marginal; and 41% continued to be incapacitated (Non-patent Document 1).

Advanced Glycation End products (hereinafter sometimes referred to as "AGEs") are substances formed in the body by a non-enzymatic reaction (Maillard reaction) between a protein (an amino group) and a carbonyl compound produced from sugar, lipid, etc. under conditions of hyperglycemia or oxidative stress (the term "carbonyl-modified protein that is a protein modified with the carbonyl compound" as used herein includes the AGEs). AGEs are a heterogeneous group of many substances, including pentosidine. Pentosidine, which is one type of AGE structure, is a fluorescent substance that was isolated from human dura mater collagen by Sell et al. in 1989. In recent years, the results of analysis using antibodies against AGEs (anti-AGEs antibodies) have revealed that AGEs levels increase in tissues and blood in various pathological conditions. For example, in diabetes, due to hyperglycemia, an increase in the levels of sugar-derived carbonyl compounds, which are precursors of AGEs, and carbonyl-modified proteins (AGEs) is observed. Due to the decreased excretion of carbonyl compounds and increased oxidative stress in renal failure, and the increased oxidative stress in inflammatory diseases, the production of carbonyl compounds is promoted, and thus an increase in the level of carbonyl-modified proteins (AGEs) is observed. It has also been reported that AGE levels increase in patients who are deficient in glyoxalase, which is an enzyme for removing carbonyl compounds. Therefore, blood AGE levels are actually used in clinical tests as an indicator of vascular complications resulting from diabetes and renal failure. Examples of methods of determining AGE levels include an ELISA method of measuring the amount of pentosidine, which is one of the AGE structures, using an anti-pentosidine antibody; and a method of measuring the amount of pentosidine in skin using an AGE Reader.

Patent Document 1: Japanese Unexamined Patent Publication No. 2001-245661
Patent Document 2: Japanese Unexamined Patent Publication No. 2003-38198
Patent Document 3: Japanese Unexamined Patent Publication No. 2003-212795
Patent Document 4: WO2004/005935 pamphlet
Patent Document 5: Japanese Unexamined Patent Publication No. 2004-251865
Patent Document 6: Japanese Unexamined Patent Publication No. 2005-55227
Patent Document 7: Japanese Unexamined Patent Publication No. 2005-278490
Non-patent Document 1: McGlashan, Schizophr Bull, 1988

DISCLOSURE OF THE INVENTION

Problem to be Solved by the Invention

Schizophrenia has unique pathological features, and, as mentioned above, schizophrenia patients have a long clinical history. Therefore, the mental distress and burden on the patients themselves and their families is great. Furthermore, since the number of schizophrenia patients is as high as 1% of the population, the social loss due to this mental disorder is immeasurable. Further, as mentioned above, the fact that patients with schizophrenia occupy 22% of all hospital beds is also a big problem from the viewpoint of medical economics. Therefore, the comprehensive diagnosis and early establishment of a therapeutic system, including early diagnosis, treatment, social rehabilitation activities, and recurrence prevention, have been desired.

The present invention was made to solve the above problem. An object of the present invention is to provide a novel method that can be effectively used for the diagnosis and treatment of schizophrenia. More specifically, an object of the invention is to provide a method for diagnosing schizophrenia; a schizophrenia diagnostic reagent or device for use in the method; and a therapeutic or ameliorating agent for schizophrenia, which is effective for the treatment or amelioration of schizophrenia.

Means for Solving the Problem

Itokawa, one of the present inventors, performed genetic analysis using families with a history of schizophrenia as subjects, and found the following. Among the families with a history of schizophrenia, a plurality of the families were deficient in glyoxalase due to a point mutation of one allele, causing a frameshift. Miyata, another of the present inventors, performed biological and chemical analyses on the patients, and found that the erythrocyte glyoxalase activity in the families with a history of schizophrenia was decreased to about half of that of a healthy person; that the blood carbonyl compound and AGE levels were high (i.e., carbonyl stress) in spite of the absence of other diseases, such as renal failure, diabetes, or inflammation; and that vitamin $B_6$ (pyridoxal) in the body was consumed for carbonyl removal, thus resulting in a low vitamin $B_6$ level, and thus leading to an increase in the homocysteine level. More specifically, Miyata confirmed that a series of biochemical abnormalities occur due to genetic abnormality of glyoxalase in schizophrenia patients.

As a result of additional research, the present inventors further confirmed that carbonyl stress and lack of vitamin $B_6$ occur not only in schizophrenia patients who are deficient in glyoxalase, but also in a portion of general schizophrenia patients. More specifically, the erythrocyte glyoxalase activity in schizophrenia patients having an amino acid mutation (Glu→Ala) at position 111 of glyoxalase I as a homozygote (5 out of 1,099 patients) was decreased to about 80% of that of a healthy person; high blood levels of carbonyl compounds and AGEs (carbonyl stress), and a low level of vitamin $B_6$ were also confirmed. Although glyoxalase I gene is known to have polymorphisms (including polymorphisms having a low activity), an Ala/Ala homozygote at position 111 was not detected in any of the 854 healthy persons. Therefore, decreased glyoxalase activity caused by this mutation is considered to cause a series of biochemical abnormalities associated with schizophrenia.

Thus, the present inventors confirmed the following. When at least one parameter selected from the group consisting of: (1) a genetic abnormality of glyoxalase I gene; (2) the activity of glyoxalase I in a biological sample; (3) the amount of a carbonyl compound or a carbonyl-modified protein that is a protein modified with the carbonyl compound (such as AGEs); and (4) the amount of pyridoxal in a biological sample is measured in a subject, and preferably (1) a genetic abnormality of glyoxalase I gene, or (3) the amount of at least one AGE is measured, and used as an indicator, the diagnosis of schizophrenia, which conventionally depended on a doctor's subjective judgment based on inquiries to the patient, can be easily and objectively made. A portion of the present invention was thus accomplished. Based on the above findings, the present inventors further confirmed that a carbonyl scavenger for inhibiting carbonyl stress, or an AGEs formation inhibitor are effective for treating or ameliorating schizophrenia. Another portion of the present invention was thus accomplished.

More specifically, the present invention provides a method for diagnosing schizophrenia, and a schizophrenia diagnostic reagent for use in the method; and a therapeutic or ameliorating agent for schizophrenia.

I. Method for Diagnosing Schizophrenia (I-1) A method for diagnosing schizophrenia comprising measuring at least one parameter in a subject, the parameter being selected from the group consisting of: (1) a genetic abnormality of glyoxalase I gene; (2) the expression level or activity of glyoxalase I in a biological sample; (3) the amount of a carbonyl compound or a carbonyl-modified protein that is a protein modified with the carbonyl compound; and (4) the amount of pyridoxal in a biological sample.

(I-2) The method for diagnosing schizophrenia according to Item (I-1), further comprising measuring (5) the amount of homocysteine in a biological sample in addition to (4) the amount of pyridoxal in the sample.

(I-3) The method for diagnosing schizophrenia according to Item (I-1) or (I-2), wherein the subject has symptoms or signs characteristic of schizophrenia according to diagnostic criteria for schizophrenia, or the subject is a borderline schizophrenic patient according to the criteria.

(I-4) The method for diagnosing schizophrenia according to one of Items (I-1) to (I-3), wherein the subject does not have renal dysfunction, diabetes, or inflammation.

(I-5) The method for diagnosing schizophrenia according to any one of Items (I-1) to (I-4), wherein (1) the genetic abnormality of glyoxalase I gene is a frameshift mutation caused by adenine insertion between adenine at position 79 and cytosine at position 80 in a base sequence (SEQ ID NO: 2) of glyoxalase I gene shown in SEQ ID NO: 1.

(I-6) The method for diagnosing schizophrenia according to any one of Items (I-1) to (I-4), wherein (1) the genetic abnormality of glyoxalase I gene is a base substitution mutation that changes the amino acid residue at position 111 from Glu to Ala in an amino acid sequence of glyoxalase I shown in SEQ ID NO: 3.

(I-7) The method for diagnosing schizophrenia according to any one of Items (I-1) to (I-4), wherein the subject has a genetic abnormality of glyoxalase I gene that lowers glyoxalase I activity, the method comprising measuring at least one parameter selected from the group consisting of the above parameters (2) to (4) in the subject.

(I-8) The method for diagnosing schizophrenia according to Item (I-7), wherein the glyoxalase I gene abnormality is a frameshift mutation caused by either adenine insertion between adenine at position 79 and cytosine at position 80 in a base sequence (SEQ ID NO: 2) of glyoxalase I gene shown in SEQ ID NO: 1, or a base substitution mutation that changes the amino acid residue at position 111 from Glu to Ala in an amino acid sequence of glyoxalase I shown in SEQ ID NO: 3.

(I-9) The method for diagnosing schizophrenia according to any one of Items (I-1) to (I-8), wherein (3) the amount of the carbonyl-modified protein is measured by an immunoassay using an anti-carbonyl-modified protein antibody, high-performance liquid chromatography, gas chromatography/mass spectrometry, or a method using an AGE Reader.

(I-10) The method for diagnosing schizophrenia according to any one of Items (I-1) to (I-9), wherein the carbonyl-modified protein is pentosidine.

(I-11) The method for diagnosing schizophrenia according to any one of Items (I-1) to (I-10), comprising the steps of:

(A) measuring at least one parameter in a subject, the parameter being selected from the group consisting of: (2) the expression level or activity of glyoxalase I in a biological sample; (3) the amount of a carbonyl compound or a carbonyl-modified protein that is a protein modified with the carbonyl compound; and (4) the amount of pyridoxal in a biological sample; and (B) comparing a parameter value obtained in step (A) with a healthy person's value of the same parameter (a control value).

(I-12) The method for diagnosing schizophrenia according to Item (I-11), wherein the subject is diagnosed as schizophrenic when the parameter value of the subject meets the following conditions:

(2) the expression level or activity of glyoxalase I in the biological sample of the subject is lower than that of a healthy person;

(3) the amount of the carbonyl compound or the carbonyl-modified protein in the subject is larger than that of a healthy person; or (4) the amount of pyridoxal in the subject is smaller than that of a healthy person.

II. Reagent or Device for the Diagnosis of Schizophrenia, and Use Thereof (II-1) A labeled or unlabeled 15- to 35-base oligonucleotide that hybridizes with a continuous oligo- or polynucleotide of 16 or more bases comprising adenine at position 79 and cytosine at position 80 in a base sequence (SEQ ID NO: 2) of a coding region of glyoxalase I gene shown in SEQ ID NO: 1 (when the oligo- or polynucleotide is RNA, the base "t" in the base sequence is replaced with "u"), and which is used for specifically amplifying the continuous oligo- or polynucleotide.

(II-2) A primer comprising the labeled or unlabeled oligonucleotide of Item (II-1), which is used for identifying adenine insertion between adenine at position 79 and cytosine at position 80 in the base sequence (SEQ ID NO: 2) of a coding region of glyoxalase I gene shown in SEQ ID NO: 1 to diagnose schizophrenia in a subject.

(II-3) A labeled or unlabeled 16- to 500-base oligonucleotide which hybridizes with a continuous oligo- or polynucleotide of 16 or more bases comprising adenine at position 79 and cytosine at position 80, or a continuous oligo- or polynucleotide of 16 or more bases comprising a base at position 332 in a base sequence (SEQ ID NO: 2) of a coding region of glyoxalase I gene shown in SEQ ID NO: 1 (when the oligo- or polynucleotide is RNA, the base "t" in the base sequence is replaced with "u"), and which is used for specifically detecting the continuous oligo- or poly-nucleotide.

(II-4) A probe comprising the labeled or unlabeled oligonucleotide of Item (II-3), which is used for identifying adenine insertion between adenine at position 79 and cytosine at position 80, or mutation at position 332 from adenine to cytosine in the base sequence (SEQ ID NO: 2) of a coding region of glyoxalase I gene shown in SEQ ID NO: 1 to diagnose schizophrenia in a subject.

(II-5) A reagent for use in the diagnosis of schizophrenia comprising the primer of Item (II-2) and/or the probe of Item (II-4), or a kit comprising the reagent.

(II-6) A reagent for use in the diagnosis of schizophrenia comprising measuring the expression level or activity of glyoxalase I, the reagent comprising at least one compound selected from the group consisting of anti-glyoxalase I antibody and a substrate reactive with glyoxalase I.

(II-7) A reagent for use in the diagnosis of schizophrenia comprising measuring (3) the amount of a carbonyl compound or a carbonyl-modified protein in a biological sample of a subject, the reagent comprising at least one compound selected from the group consisting of (a) a carbonyl compound or a carbonyl-modified protein of a known concentration, and (b) an unlabeled or labeled anti-carbonyl-modified protein antibody.

(II-8) The reagent according to (II-5), wherein the carbonyl-modified protein is pentosidine.

(II-9) An AGE Reader for measuring the amount of carbonyl-modified proteins in skin, the AGE Reader being used for the diagnosis of schizophrenia comprising measuring (3) the amount of a carbonyl-modified protein in a subject.

(II-10) The AGE Reader according to Item (II-9), which is accompanied by a document stating that the AGE Reader can be used for the diagnosis of schizophrenia.

(II-11) Use of an AGE Reader for measuring the amount of carbonyl-modified proteins in skin to diagnose schizophrenia.

(II-12) A reagent for use in the diagnosis of schizophrenia comprising measuring (4) the amount of pyridoxal in a biological sample of a subject, the reagent comprising at least one compound selected from the group consisting of (a) pyridoxal of a known concentration, and (b) a reagent for determining pyridoxal.

III. Therapeutic or Ameliorating Agent for Schizophrenia (III-1) A therapeutic or ameliorating agent for schizophrenia, comprising a carbonyl scavenger or a carbonyl-modified protein formation inhibitor (hereinafter sometimes referred to as an "AGEs formation inhibitor") as an active ingredient.
(III-2) The therapeutic or ameliorating agent for schizophrenia according to Item (III-1), wherein the carbonyl scavenger is vitamin $B_6$.
(III-3) The therapeutic or ameliorating agent for schizophrenia according to Item (III-1), wherein the AGE formation inhibitor is a compound containing a substituent that inhibits binding of vitamin $B_6$ molecules to the 4-position of 1-substituted-, unsubstituted-3-substituted- or unsubstituted-2-pyrazolin-5-one in free form or salt form (the substituent may be one derived from vitamin $B_6$ molecules), or an intramolecular rearrangement product thereof.
(III-4) The therapeutic or ameliorating agent for schizophrenia according to Item (III-3), wherein the compound is selected from compounds in free form or salt form which are represented by Formula (1)

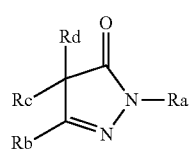

or compounds represented by Formula (2)

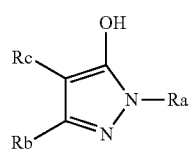

wherein Ra is a substituted or unsubstituted aromatic group, each of Rb, Rc, and Rd is a hydrogen atom or a monovalent organic group, or Rb and Rc may be combined to form a fused ring, or Rc and Rd may be combined to form a divalent organic group.
(III-5) The therapeutic or ameliorating agent for schizophrenia according to Item (III-4), wherein the aromatic group represented by Ra in Formula (1) or (2) is a carbocyclic or heterocyclic aromatic group containing up to 20 ring constituent atoms that may include up to 4 heteroatoms, the aromatic group being optionally substituted with up to 3 substituents.
(III-6) The therapeutic or ameliorating agent for schizophrenia according to Item (III-4) or (III-5), wherein the monovalent organic group represented by Rb, Rc or Rd in Formula (1) of (2) is either a straight, branched or cyclic, aliphatic, alicyclic or aromatic hydrocarbon group containing up to 30 carbon atoms and being optionally substituted with up to 3 substituents, or a group selected from the group consisting of halogen, nitro, amino, hydroxy, thiol, carboxy, carboxy(lower)alkyl, lower alkoxycarbonyl, formyl, lower alkanoyl, lower alkylamino, di(lower)alkylamino, lower alkanoylamino, aryl(lower)alkanoyl, aryloxy-amino, sulfonic acid, and 3- to 7-membered heterocyclic groups, each of which may optionally be substituted with one or more substituents.
(III-7) The therapeutic or ameliorating agent for schizophrenia according to Item (III-4) or (III-5), wherein the fused ring formed by combining Rb and Rc in Formula (1) or (2) is a 5- or 6-membered saturated carbocyclic ring which may optionally be substituted with one or more substituents.
(III-8) The therapeutic or ameliorating agent for schizophrenia according to Item (III-4) or (III-5), wherein the divalent organic group formed by combining Rc and Rd in Formula (1) or (2) is a group selected from the group consisting of phenylmethylene, phenyl-alkenylmethylene, quinolinyl-methylene, furanyl-methylene, diazolyl-methylene, aminomethylene, di(lower)alkylaminomethylene, pyridylmethylene, and thiophenylmethylene, each of which may optionally be substituted with one or more substituents.
(III-9) The therapeutic or ameliorating agent for schizophrenia according to any one of Items (III-4) to (III-8), wherein the compound is represented by Formula (1) or (2), wherein the substituent is selected from the group consisting of lower alkyl, lower alkenyl, lower alkoxy, lower alkenyloxy, lower alkanoyl, halo(lower)alkyl, carboxyl, lower alkoxycarbonyl, carboxy(lower)alkyl, halogen, nitro, amino, lower alkylamino, di(lower)alkylamino, lower alkanoylamino, hydroxy, thiol, hydroxysulfonyl, aminosulfonyl, aryl(lower) alkanoyl, aryloxyamino, aryl, aryl(lower)alkyl, cyclo(lower) alkyl, cyclo(lower)alkenyl, cyclo(lower)alkyl(lower)alkyl, and 3- to 7-membered heterocyclic groups.
(III-10) The therapeutic or ameliorating agent for schizophrenia according to Item (III-4), wherein the compound is represented by Formula (1), wherein Ra is a phenyl group, Rb is a methyl group, and Rc and Rd are combined to form 3-hydroxy-5-hydroxymethyl-2-methylpyridin-4-ylmethylene.
(III-11) The therapeutic or ameliorating agent for schizophrenia according to Item (III-4), wherein the compound is represented by Formula (2) wherein Ra is a phenyl group, Rb is a methyl group, and Rc is a 6-methyl-1,3-dihydrofuro[3,4-c]pyridin-7-ol group.
(III-12) The therapeutic or ameliorating agent for schizophrenia according to Item (III-4), wherein the compound is edaravone (3-methyl-1-phenyl-2-pyrazolin-5-one).
(III-13) The therapeutic or ameliorating agent for schizophrenia according to Item (III-1), wherein the AGEs formation inhibitor is a compound represented by Formula (1)

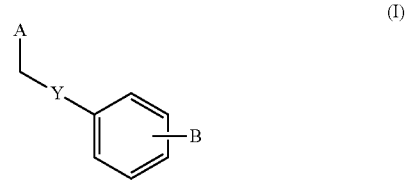

wherein A is a group represented by Formula (A1), (A2), or (A3)

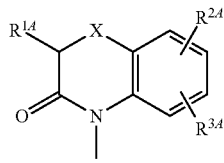
(A1)

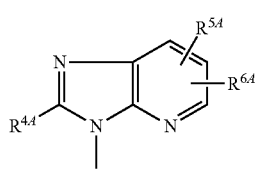
(A2)

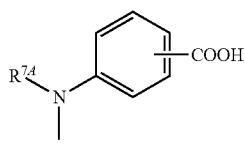
(A3)

B is 1H-tetrazol-5-yl or 2,4-dioxo-1,3-thiazolidin-5-yl; X is methylene, an oxygen atom, or a sulfur atom; Y is a single bond or a $C_{6-10}$ arylene group; $R^{1A}$ is a hydrogen atom or a $C_{1-6}$ alkyl group; $R^{2A}$ and $R^{3A}$ are the same or different, and each represent a hydrogen atom, a carboxyl group or a $C_{1-6}$ alkyl group; $R^{4A}$, $R^{5A}$, and $R^{6A}$ are the same or different, and each represent a hydrogen atom or a $C_{1-6}$ alkyl group; and $R^{7A}$ is a $C_{1-10}$ alkylcarbonyl group; provided that when A is a group represented by (A2), B is 2,4-dioxothiazolidin-5-yl); or a pharmaceutically acceptable salt or ester thereof.

(III-14) The therapeutic or ameliorating agent for schizophrenia according to Item (III-13), wherein B in Formula (1) is 1H-tetrazol-5-yl.

(III-15) The therapeutic or ameliorating agent for schizophrenia according to Item (III-13) or (III-14), wherein Y in Formula (1) is a $C_{6-10}$ arylene group.

(III-16) The therapeutic or ameliorating agent for schizophrenia according to any one of Items (III-13) to (III-15), wherein Y in Formula (1) is phenylene.

(III-17)

The therapeutic or ameliorating agent for schizophrenia according to any one of Items (III-13) to (III-16), wherein B in Formula (I) is 2,4-dioxo-1,3-thiazolidin-5-yl.

(III-18) The therapeutic or ameliorating agent for schizophrenia according to any one of Items (III-3) to (III-7), wherein A in Formula (I) is a group represented by Formula (A1), and B is 1H-tetrazol-5-yl.

(III-19) The therapeutic or ameliorating agent for schizophrenia according to any one of Items (III-13) to (III-18), wherein A in Formula (1) is a group represented by Formula (A2), and B is 2,4-dioxo-1,3-thiazolidin-5-yl.

(III-20) The therapeutic or ameliorating agent for schizophrenia according to Item (III-13), wherein the AGE formation inhibitor is a compound represented by Formula (IA3)

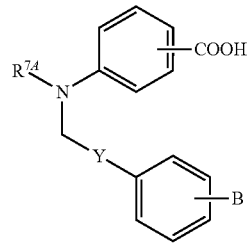
(IA3)

wherein B is 1H-tetrazol-5-yl or 2,4-dioxo-1,3-thiazolidin-5-yl, Y is a single bond or a $C_{6-10}$ arylene group, and $R^{7A}$ is a $C_{1-10}$ alkylcarbonyl group; or a pharmaceutically acceptable salt or ester thereof.

(III-21) The therapeutic or ameliorating agent for schizophrenia according to Item (III-20), wherein B in Formula (IA3) is 1H-tetrazol-5-yl.

(III-22) The therapeutic or ameliorating agent for schizophrenia according to Item (III-13), wherein the AGE formation inhibitor is a compound selected from the group consisting of 3-[N-[[4-[2-(1H-tetrazol-5-yl)phenyl]phenyl]methyl]-N-pentanoylamino]benzoic acid, 3-[N-[[4-[2-(1H-tetrazol-5-yl)phenyl]phenyl]methyl]-N-butanoylamino]benzoic acid, 3-N-[[4-[2-(1H-tetrazol-5-yl)phenyl]phenyl]methyl]-N-[heptanoylamino]benzoic acid, 2-oxo-3-propyl-1-[[4-[2-(1H-tetrazol-5-yl)phenyl]phenyl]methyl]-1,3,4-trihydroquinoline-7-carboxylic acid, and 5-[4-[(2-ethyl-5,7-dimethylimidazo[4,5-b]pyridin-3-yl)methyl]phenyl]-1,3-thiazolidine-2,4-dione; or a pharmaceutically acceptable salt or ester thereof.

(III-23) The therapeutic or ameliorating agent for schizophrenia according to Item (III-13), wherein the AGE formation inhibitor is 3-[N-[4-(2,4-dioxothiazolidine 5-yl)benzyl]-N-pentanoylamino]benzoic acid or 3-[N-[[4-[2-(1H-tetrazol-5-yl)phenyl]phenyl]methyl]-N-octanoylamino]benzoic acid; or a pharmaceutically acceptable salt or ester thereof.

(III-24) The therapeutic or ameliorating agent for schizophrenia according to Item (III-13), wherein the AGE formation inhibitor is a compound represented by Formula (II)

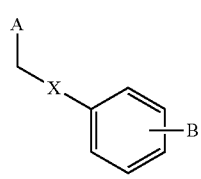
(II)

wherein A is a group represented by Formula (A4), (A5), (A6), or (A7),

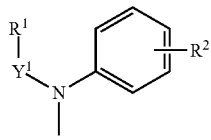
(A4)

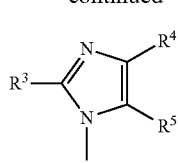
(A5)

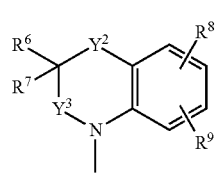
(A6)

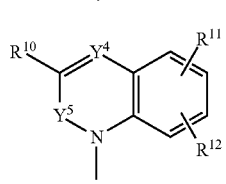
(A7)

B is 1H-tetrazol-5-yl or 2,4-dioxo-1,3-thiazolidin-5-yl;

X is a single bond or a $C_{6-30}$ arylene group;

$Y^1$ is carbonyl, sulfonyl, or a single bond;

$Y^2$ is a $C_{1-6}$ alkylene group or a single bond;

$Y^3$ is methylene, carbonyl, or a single bond;

$Y^4$ is methine or a nitrogen atom;

$Y^5$ is methylene, carbonyl, or a single bond;

$R^1$ is a $C_{1-8}$ alkyl group (the $C_{1-8}$ alkyl group may optionally be substituted with 1 to 3 substituents selected from the group α of substituents shown below), a $C_{6-14}$ aryl group (the $C_{6-14}$ aryl group may optionally be substituted with 1 to 5 substituents selected from the group β of substituents shown below), a $C_{6-14}$ aryl-$C_{1-6}$ alkyl group (the $C_{6-14}$ aryl-$C_{1-6}$ alkyl group may optionally be substituted with 1 to 5 substituents selected from the group β of substituents shown below), a 4- to 10-membered heterocyclic group containing 1 to 3 identical or different heteroatoms selected from the group consisting of nitrogen, oxygen, and sulfur (the heterocyclic group may optionally be substituted with 1 to 5 substituents selected from the group β of substituents shown below), a 4- to 10-membered heterocyclic-$C_{1-6}$ alkyl group containing 1 to 3 identical or different heteroatoms selected from the group consisting of nitrogen, oxygen, and sulfur (the heterocyclic-$C_{1-6}$ alkyl group may optionally be substituted with 1 to 5 substituents selected from the group β of substituents shown below), a $C_{3-7}$ cycloalkyl group (the $C_{3-7}$ cycloalkyl group may optionally be substituted with 1 to 5 substituents selected from the group β of substituents shown below), a $C_{3-7}$ cycloalkyl-$C_{1-6}$ alkyl group (the $C_{3-7}$ cycloalkyl-$C_{1-6}$ alkyl group may optionally be substituted with 1 to 5 substituents selected from the group β of substituents shown below), a $C_{6-14}$ aryl-carbonyl-$C_{1-6}$ alkyl group (the $C_{6-14}$ aryl-carbonyl-$C_{1-6}$ alkyl group may optionally be substituted with 1 to 5 substituents selected from the group β of substituents shown below), or a $C_{1-6}$ aliphatic acyl group (the $C_{1-6}$ aliphatic acyl group may optionally be substituted with 1 to 5 substituents selected from the group β of substituents shown below);

$R^2$ is a hydrogen atom, a group selected from the group β of substituents shown below, a carboxyl group, or a group represented by —C(O)NR$^{13}$R$^{14}$;

$R^3$ is a hydrogen atom, a $C_{1-8}$ alkyl group (optionally substituted with 1 to 3 substituents selected from the group α of substituents shown below), a $C_{6-14}$ aryl group (optionally substituted with 1 to 5 substituents selected from the group β of substituents shown below), or a 4- to 10-membered heterocyclic group containing 1 to 3 identical or different heteroatoms selected from the group consisting of nitrogen, oxygen, and sulfur (the heterocyclic group may optionally be substituted with 1 to 5 substituents selected from the group β of substituents shown below);

$R^4$ and $R^5$ are the same or different, and each represent a hydrogen atom or a $C_{6-14}$ aryl group (the $C_{6-14}$ aryl group may optionally be substituted with 1 to 5 substituents selected from the group β of substituents shown below);

$R^6$ and $R^7$ may join to form $C_{3-7}$ cycloalkane, or may be the same or different and each represent a hydrogen atom or a $C_{1-8}$ alkyl group (the alkyl group may optionally be substituted with 1 to 3 substituents selected from the group α of substituents);

$R^8$ and $R^9$ are the same or different, and each represent a hydrogen atom, a group selected from the group β of substituents shown below, a carboxyl group, or a group represented by —C(O)NR$^{13}$R$^{14}$;

$R^{18}$ is a hydrogen atom, a $C_{1-8}$ alkyl group (the $C_{1-8}$ alkyl group may optionally be substituted with 1 to 3 substituents selected from the group α of substituents shown below) a $C_{6-14}$ aryl group (the $C_{6-14}$ aryl group may optionally be substituted with 1 to 5 substituents selected from the group β of substituents shown below), or a 4- to 10-membered heterocyclic group containing 1 to 3 identical or different heteroatoms selected from the group consisting of nitrogen, oxygen, and sulfur (the heterocyclic group may optionally be substituted with 1 to 5 substituents selected from the group β of substituents);

$R^{11}$ and $R^{12}$ are the same or different, and each represent a hydrogen atom, a group selected from the group β of substituents listed below, a carboxyl group, or a group represented by —C(O)NR$^{13}$R$^{14}$;

$R^{13}$ and $R^{14}$ may join to form a 4- to 10-membered, nitrogen-containing heterocyclic ring (the heterocyclic ring may optionally be substituted with 1 to 5 substituents selected from the group β of substituents shown below), or may be the same or different and each represent a hydrogen atom or a $C_{1-8}$ alkyl group (the $C_{1-8}$ alkyl group may optionally be substituted with 1 to 3 substituents selected from the group α of substituents shown below), provided that:

(1) when $R^1$ is a $C_{1-8}$ alkyl group and $Y^1$ is a single bond, B is 2,4-dioxo-1,3-thiazolidine-5-yl;

(2) when $Y^2$ is methylene, neither $R^6$ nor $R^7$ is a hydrogen atom;

(3) when $R^1$ is an unsubstituted $C_{1-8}$ alkyl group, $Y^1$ is not carbonyl; and (4) when $R^1$ is an unsubstituted $C_{1-6}$ aliphatic acyl group, $Y^1$ is not a single bond;

the group α of substituents consisting of halogen atoms, $C_{1-6}$ alkylthio groups, $C_{1-6}$ aliphatic acyl groups, $C_{1-6}$ alkylsulfonyl groups, $C_{1-6}$ alkoxy groups, a cyano group, and a nitro group; and the group β of substituents consisting of halogen atoms, $C_{1-6}$ alkyl groups, halo-$C_{1-6}$ alkyl groups, $C_{1-6}$ alkoxy groups, $C_{1-6}$ alkylthio groups, $C_{1-6}$ alkylsulfonyl groups, $C_{1-6}$ aliphatic acyl groups, an oxo group, a cyano group, a nitro group, $C_{3-7}$ cycloalkyl groups, $C_{6-14}$ aryl groups, $C_{1-6}$ alkoxyimino groups, $C_{6-14}$ aryl-carbonyl groups, and a 4- to 10-membered heterocyclic group containing 1 to 3 identical or different heteroatoms selected from the group consisting of nitrogen, oxygen, and sulfur; or a pharmaceutically acceptable salt or ester thereof.

(III-25) The therapeutic or ameliorating agent for schizophrenia according to Item (III-13), wherein the AGE formation inhibitor is a compound represented by Formula (II)

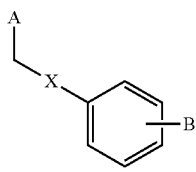

(II)

wherein A is a group represented by Formula (A4), (A5), (A6), or (A7),

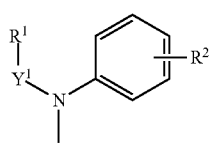

(A4)

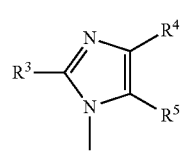

(A5)

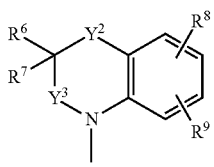

(A6)

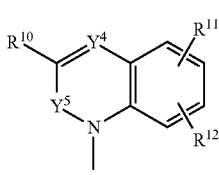

(A7)

B is 1H-tetrazol-5-yl or 2,4-dioxo-1,3-thiazolidin-5-yl;
X is a single bond or a $C_{6-10}$ arylene group;
$Y^1$ is carbonyl, sulfonyl, or a single bond;
$Y^2$ is a $C_{1-6}$ alkylene group or a single bond;
$Y^3$ is methylene, carbonyl, or a single bond;
$Y^4$ is methine or a nitrogen atom;
$Y^5$ is methylene, carbonyl, or a single bond;
$R^1$ is a $C_{1-8}$ alkyl group (the $C_{1-8}$ alkyl group may optionally be substituted with 1 to 3 substituents selected from the group α of substituents shown below), a $C_{6-14}$ aryl group (the $C_{6-14}$ aryl group may optionally be substituted with 1 to 5 substituents selected from the group β of substituents shown below), a $C_{6-14}$ aryl-$C_{1-6}$ alkyl group (the $C_{6-14}$ aryl-$C_{1-6}$ alkyl group may optionally be substituted with 1 to 5 substituents selected from the group β of substituents shown below), a 4- to 10-membered heterocyclic group containing 1 to 3 identical or different heteroatoms selected from the group consisting of nitrogen, oxygen, and sulfur (the heterocyclic group may optionally be substituted with 1 to 5 substituents selected from the group β of substituents shown below), a 4- to 10-membered heterocyclic-$C_{1-6}$ alkyl group containing 1 to 3 identical or different heteroatoms selected from the group consisting of nitrogen, oxygen, and sulfur (the heterocyclic-$C_{1-6}$ alkyl group may optionally be substituted with 1 to 5 substituents selected from the group β of substituents shown below), a $C_{3-7}$ cycloalkyl group, a $C_{3-7}$ cycloalkyl-$C_{1-6}$ alkyl group, or a $C_{6-14}$ aryl-carbonyl-$C_{1-6}$ alkyl group (the $C_{6-14}$ aryl-carbonyl-$C_{1-6}$ alkyl group may optionally be substituted with 1 to 5 substituents selected from the group β of substituents shown below);

$R^2$ is a hydrogen atom, a group selected from the group β of substituents shown below, a carboxyl group, or a group represented by —C(O)NR$^{13}$R$^{14}$;

$R^3$ is a hydrogen atom, a $C_{1-8}$ alkyl group (the $C_{1-8}$ alkyl group may optionally be substituted with 1 to 3 substituents selected from the group α of substituents shown below), a $C_{6-14}$ aryl group (the $C_{6-14}$ aryl group may optionally be substituted with 1 to 5 substituents selected from the group β of substituents shown below), or a 4- to 10-membered heterocyclic group containing 1 to 3 identical or different heteroatoms selected from the group consisting of nitrogen, oxygen, and sulfur (the heterocyclic group may optionally be substituted with 1 to 5 substituents selected from the group β of substituents shown below);

$R^4$ and $R^5$ are the same or different, and each represent a hydrogen atom or a $C_{6-14}$ aryl group (the $C_{6-14}$ aryl group may optionally be substituted with 1 to 5 substituents selected from the group β of substituents shown below);

$R^6$ and $R^7$ may join to form $C_{3-7}$ cycloalkane, or may be the same or different and each represent a hydrogen atom or a $C_{1-8}$ alkyl group (the $C_{1-8}$ alkyl group may optionally be substituted with 1 to 3 substituents selected from the group α of substituents);

$R^8$ and $R^9$ are the same or different, and each represent a hydrogen atom, a group selected from the group β of substituents shown below, a carboxyl group, or a group represented by —C(O)NR$^{13}$R$^{14}$;

$R^{10}$ is a hydrogen atom, a $C_{1-8}$ alkyl group (the $C_{1-8}$ alkyl group may optionally be substituted with 1 to 3 substituents selected from the group α of substituents shown below) a $C_{6-14}$ aryl group (the $C_{6-14}$ aryl group may optionally be substituted with 1 to 5 substituents selected from the group β of substituents shown below), or a 4- to 10-membered heterocyclic group containing 1 to 3 identical or different heteroatoms selected from the group consisting of nitrogen, oxygen, and sulfur (the heterocyclic group may optionally be substituted with 1 to 5 substituents selected from the group β of substituents);

$R^{11}$ and $R^{12}$ are the same or different, and each represent a hydrogen atom, a group selected from the group β of substituents listed below, a carboxyl group, or a group represented by —C(O)NR$^{13}$R$^{14}$;

$R^{13}$ and $R^{14}$ may join to form a 4- to 10-membered, nitrogen-containing heterocyclic ring (the nitrogen-containing heterocyclic ring may optionally be substituted with 1 to 5 substituents selected from the group β of substituents shown below), or may be the same or different and each represent a hydrogen atom or a $C_{1-8}$ alkyl group (the $C_{1-8}$ alkyl group may optionally be substituted with 1 to 3 substituents selected from the group α of substituents shown below), provided that:

(1) when $R^1$ is a $C_{1-8}$ alkyl group and $Y^1$ is a single bond, B is 2,4-dioxo-1,3-thiazolidine-5-yl;

(2) when $Y^2$ is methylene, neither $R^6$ nor $R^7$ is a hydrogen atom;

(3) when $R^1$ is an unsubstituted $C_{1-8}$ alkyl group, $Y^2$ is not carbonyl; and (4) when $R^1$ is an unsubstituted $C_{1-6}$ aliphatic acyl group, $Y^1$ is not a single bond;

the group α of substituents consisting of halogen atoms, $C_{1-6}$ alkylthio groups, $C_{1-6}$ alkylsulfonyl groups, $C_{1-6}$ alkoxy groups, a cyano group, and a nitro group; and the group β of substituents consisting of halogen atoms, $C_{1-6}$ alkyl groups, halo-$C_{1-6}$ alkyl groups, $C_{1-6}$ alkoxy groups, $C_{1-6}$ alkylthio groups, $C_{1-6}$ alkylsulfonyl groups, $C_{1-6}$ aliphatic acyl groups, a cyano group, a nitro group, $C_{3-7}$ cycloalkyl groups, $C_{6-14}$ aryl groups, and a 4- to 10-membered heterocyclic group containing 1 to 3 identical or different heteroatoms selected from the group consisting of nitrogen, oxygen, and sulfur; or a pharmaceutically acceptable salt or ester thereof.

(III-25) The therapeutic or ameliorating agent for schizophrenia according to Item (III-23) or (III-24), wherein B in Formula (II) is 1H-tetrazol-5-yl, and X is a $C_{6-10}$ arylene group.

(III-26) The therapeutic or ameliorating agent for schizophrenia according to Item (III-25), wherein X in Formula (II) is phenylene.

(III-27) The therapeutic or ameliorating agent for schizophrenia according to Item (III-23) or (III-24), wherein B is 2,4-dioxothiazolidin-5-yl, and X is a single bond.

(III-28) The therapeutic or ameliorating agent for schizophrenia according to Item (III-23) or (III-24), wherein A in Formula (II) is a group represented by Formula (A1), and $R^2$ is a hydrogen atom or a carboxyl group.

(III-29) The therapeutic or ameliorating agent for schizophrenia according to Item (III-23) or (III-24), wherein A in Formula (II) is a group represented by Formula (A2), and $R^3$ is a hydrogen atom or a $C_{6-14}$ aryl group (the $C_{6-14}$ aryl group may optionally be substituted with 1 to 5 substituents selected from the group β of substituents below).

(III-30) The therapeutic or ameliorating agent for schizophrenia according to Item (III-23) or (III-24), wherein A in Formula (II) is a group represented by Formula (A3), $Y^3$ is carbonyl or a single bond, and $R^8$ and $R^9$ are the same or different, and each represents a hydrogen atom or a carboxyl group.

(III-31) A therapeutic or ameliorating agent for schizophrenia according to Item (III-23), wherein A in Formula (II) is a group represented by Formula (A4), $Y^5$ is carbonyl or a single bond, and $R^{11}$ and $R^{12}$ are the same or different, and each represents a hydrogen atom or a carboxyl group.

(III-32) The therapeutic or ameliorating agent for schizophrenia according to Item (III-23) or (III-24), wherein the AGE formation inhibitor is at least one compound selected from the group consisting of:

(1) 3-{N-(3-phenylpropiol)-N-[2'-(1H-tetrazol-5-yl)biphenyl-4-ylmethyl]amino}benzoic acid,
(2) 3-{N-pentyl-N-[4-(2,4-dioxo-1,3-thiazolidin-5-yl)benzyl]amino}benzoic acid,
(3) 1-[4-(2,4-dioxo-1,3-thiazolidin-5-yl)benzyl]-2-methyl-1,2,3,4-tetrahydroquinoline-7-carboxylic acid,
(4) 5-[4-(N-methylsulfonyl-N-phenylaminomethyl)phenyl]-1,3-thiazolidine-2,4-dione,
(5) 5-[4-(N-butylsulfonyl-N-phenylaminomethyl)phenyl]-1,3-thiazolidine-2,4-dione,
(6) 3-{N-[4-(2,4-dioxo-1,3-thiazolidin-5-yl)benzyl]-N-(methylsulfonyl)amino}benzoic acid,
(7) 3-{N-butylsulfonyl-N-[4-(2,4-dioxo-1,3-thiazolidin-5-yl)benzyl]amino}benzoic acid,
(8) 5-{4-[2-(2-pyridyl)benzimidazol-1-ylmethyl]phenyl}-1,3-thiazolidin-2,4-dione,
(9) 5-[4-(2-phenylimidazol-1-ylmethyl)phenyl]-1,3-thiazolidine-2,4-dione,
(10) 1-[4-(2,4-dioxo-1,3-thiazolidin-5-yl)benzyl]-2-oxo-3-propyl-1,2-dihydroquinoline-7-carboxylic acid,
(11) 3-{N-cyclohexanecarbonyl-N-[4-(2,4-dioxo-1,3-thiazolidin-5-yl)benzyl]amino}benzoic acid,
(12) 3-{N-[4-(2,4-dioxo-1,3-thiazolidin-5-yl)benzyl]-N-(pyridin-3-carbonyl)amino}benzoic acid,
(13) 3-{N-[4-(2,4-dioxo-1,3-thiazolidin-5-yl)benzyl]-N-(3-phenylpropiol)amino}benzoic acid,
(14) 3-{N-(biphenyl-4-carbonyl)-N-[4-(2,4-dioxo-1,3-thiazolidin-5-yl)benzyl]amino}benzoic acid,
(15) 3-{N-(phenylsulfonyl)-N-[4-(2,4-dioxo-1,3-thiazolidin-5-yl)benzyl]amino}benzoic acid,
(16) 3-{N-(4-methylphenylsulfonyl)-N-[4-(2,4-dioxo-1,3-thiazolidin-5-yl)benzyl]amino}benzoic acid,
(17) 3-{N-(biphenyl-4-sulfonyl)-N-[4-(2,4-dioxo-1,3-thiazolidin-5-yl)benzyl]amino}benzoic acid,
(18) 3-{N-(2-naphthylsulfonyl)-N-[4-(2,4-dioxo-1,3-thiazolidin-5-yl)benzyl]amino}benzoic acid,
(19) 3-{N-(benzylsulfonyl)-N-[4-(2,4-dioxo-1,3-thiazolidin-5-yl)benzyl]amino}benzoic acid,
(20) 1-[4-(2,4-dioxo-1,3-thiazolidin-5-yl)benzyl]-2-oxo-3-propyl-2,3-1H-indole-6-carboxylic acid,
(21) 1-[4-(2,4-dioxo-1,3-thiazolidin-5-yl)benzyl]-2-oxo-3-propyl-2,3,4,5-tetrahydro-1H-benzo[b]azepine-8-carboxylic acid,
(22) 3,3-dimethyl-1-[4-(2,4-dioxo-1,3-thiazolidin-5-yl)benzyl]-2-oxo-1,2,3,4-tetrahydroquinoline-7-carboxylic acid,
(23) 1'-[4-(2,4-dioxo-1,3-thiazolidin-5-yl)benzyl]-2'-oxo-1',4'-dihydro-2'H-spiro[cyclopropane-1,3'-quinoline]-7'-carboxylic acid,
(24) 3-{N-phenethyl-N-[2'-(1H-tetrazol-5-yl)biphenyl-4-ylmethyl]amino}benzoic acid,
(25) 3-{N-[4-(2,4-dioxo-1,3-thiazolidin-5-yl)benzyl]-N-[(5-methyl-2-phenyl-1,3-oxazol-4-yl)acetyl]amino}benzoic acid,
(26) 3-{N-(3-cyclohexylpropanoyl)-N-[2'-(1H-tetrazol-5-yl)biphenyl-4-ylmethyl]amino}benzoic acid,
(27) 3-{N-(2-oxo-2-phenylethyl)-N-[2'-(1H-tetrazol-5-yl)biphenyl-4-ylmethyl]amino}benzoic acid,
(28) 3-{N-[4-(2,4-dioxo-1,3-thiazolidin-5-yl)benzyl]-N-[4-(2-methylthiazole4-yl)benzenesulphonyl]amino}benzoic acid, and
(29) 3-{N-(biphenyl-4-ylmethyl)-N-[4-(2,4-dioxo-1,3-thiazolidin-5-yl)benzyl]amino}benzoic acid; or a pharmaceutically acceptable salt or ester thereof.

(III-33) A packaged pharmaceutical product comprising the therapeutic or ameliorating agent for schizophrenia of any one of Items (III-1) to (III-32), and a document, the document stating that the therapeutic or ameliorating agent can be used for treatment or amelioration of schizophrenia, or describing how to use the product.

(III-34) A method for treating or ameliorating schizophrenia comprising administering a pharmaceutically effective amount of the therapeutic or ameliorating agent for schizophrenia of any one of Items (III-1) to (III-32) to a warm-blooded animal.

IV. Method of Screening a Therapeutic or Ameliorating Agent for Schizophrenia (IV-1) A method of screening a therapeutic or ameliorating agent for schizophrenia, comprising selecting, from test substances, a substance having an effect of carbonyl removal or an inhibitory effect on carbonyl-modified protein formation.

Effect of the Invention

According to the diagnostic method of the present invention, at least one parameter selected from the group consisting of: (1) a genetic abnormality of glyoxalase I gene; (2) the expression level or activity of glyoxalase I in a biological sample; (3) the amount of a carbonyl compound or a carbonyl-modified protein that is a protein modified with the carbonyl compound; and (4) the amount of pyridoxal in a biological sample is measured in a subject, and the obtained value is used as an indicator, whereby the diagnosis of schizophrenia, which conventionally depended on a doctor's subjective judgment based on inquiries to the patient, can be easily and objectively made. Further, according to the present invention, a compound having an effect of carbonyl removal (a carbonyl scavenger effect) or an inhibitory effect on AGE formation is used to inhibit carbonyl stress in patients, whereby schizophrenia can be treated or the condition can be ameliorated. The therapeutic or ameliorating agent for schizophrenia according to the present invention is particularly effective for schizophrenia caused by carbonyl stress resulting from glyoxalase I gene abnormality.

According to the screening method of the present invention, a substance effective for treating or ameliorating schizophrenia, i.e., a therapeutic or ameliorating agent for schizophrenia can be easily selected from test substances and obtained by using carbonyl-removing effects or AGE formation inhibitory effects as an indicator. The screening method of the present invention is effective as a method for searching for a substance effective for treating and ameliorating schizophrenia caused by carbonyl stress resulting from glyoxalase I gene abnormality.

DESCRIPTION

Best Mode for Carrying Out the Invention

I. Method for Diagnosing Schizophrenia

The method for diagnosing schizophrenia of the present invention can be conducted by measuring at least one parameter mentioned below using a biological sample derived from a subject:

(1) the presence of genetic abnormality of glyoxalase I gene,
(2) the expression level or activity of glyoxalase I,
(3) the amount of a carbonyl compound or a carbonyl-modified protein (for example, the amount of "Advanced Glycation End products" (AGEs)), and
(4) the amount of pyridoxal.

When schizophrenia is diagnosed by measuring (4) the amount of pyridoxal in a biological sample, (5) the amount of homocysteine in a biological sample may also be measured.

Examples of the biological samples that can be used in the test of the invention include blood and blood components (serum, plasma, hemocyte, etc.), urine, spinal fluid, saliva, lacrimal fluid, sweat and like liquid components derived from a living body; and hair, partial tissues excised by biopsy and like solid components derived from a living body. Among these, blood and blood components are preferable, and serum is particularly preferable. The samples may be used, as the biological samples of the invention, immediately after being collected from a living body or after being subjected to some treatment.

An example of a preferable subject is a human being. However, the subject is not limited to human beings, and may be selected from mammals other than human beings, such as monkeys, mice, rats, and guinea pigs.

The subject has symptoms or signs characteristic of schizophrenia according to diagnostic criteria for schizophrenia, or the subject is suspected of having schizophrenia according to the criteria. In the invention, the criteria ordinarily used in the art can be used as the diagnostic criteria for schizophrenia. Specifically, the "International Classification of Diseases" (ICD) of the World Health Organization (WHO), and the "Diagnostic and Statistical Manual of Mental Disorders" (DSM) of the American Psychiatric Association (APA) can be used as the diagnostic criteria for schizophrenia. FIG. 1 shows the criteria for diagnosing schizophrenia in the "International Classification of Diseases, Tenth Revision" (ICD-10), and FIG. 2 shows the criteria in the "Diagnostic and Statistical Manual of Mental Disorders, Fourth Edition" (DSM-IV).

When schizophrenia is diagnosed by using at least one of the parameters (2) to (4), or (2) to (5), the subject may be one who has a genetic abnormality of glyoxalase I gene, and may also be a subject who had the test for detecting a genetic abnormality of glyoxalase I gene described (1) below. Here, the genetic abnormality of glyoxalase I gene in the invention includes genetic abnormalities that reduce the glyoxalase I activity, such as deficient or defective expression of glyoxalase I. Specifically, the target genetic abnormalities include a frameshift mutation caused by point mutation of at least one allele of glyoxalase I gene (adenine insertion between adenine at position 79 and cytosine at position 80 in a base sequence (SEQ ID NO: 2) of a coding region of glyoxalase-I gene), and a mutation homozygously including a mutation (Glu→Ala) of amino acid residue at position 111 in an amino acid sequence of glyoxalase I shown in SEQ ID NO: 3. It was confirmed that, in the former type of genetic abnormality, the glyoxalase I activity in blood was reduced by about 50% compared to that of a healthy subject. It was also confirmed that, in the latter type of genetic abnormality, the glyoxalase I activity in blood was reduced by about 20% compared to that of a healthy subject (see the Examples). The genetic abnormalities of the invention are not limited to those, and may include any type of genetic abnormality that causes reduction of glyoxalase I activity.

When schizophrenia is diagnosed by using at least one of the parameters (3) and (4), or (3) to (5), it is preferable that the subject does not have at least renal dysfunction, diabetes and inflammations. This is because the parameters of (3) the amount of a carbonyl compound or a carbonyl-modified proteins (sucha as AGEs), (4) the amount of pyridoxal, and (5) the amount of homocysteine vary depending on the presence or absence of renal dysfunction, diabetes and/or inflammation. Therefore, when schizophrenia is diagnosed based on parameters (3) and (4) or parameters (3) to (5) described above, it is preferable to check the presence or absence of renal dysfunctions, diabetes and/or inflammations by oral consultation and/or biochemical examination prior to or at the same time of conducting the test of the invention.

(1) Detection of Genetic Abnormality of Glyoxalase I Gene

The genetic abnormalities of glyoxalase I gene (hereunder, glyoxalase I gene may be referred to as "GLO-I" gene) targeted by the invention include those resulting in reduction of GLO-I activity, such as deficient in glyoxalase I (GLO-I) and defective expression of GLO-I. There is no limitation to the genetic abnormalities, as long as they reduce the GLO-I activity. Specific examples thereof include (1-1) a frameshift mutation caused by point mutation (adenine insertion between adenine at position 79 and cytosine at position 80) of at least one allele in a base sequence (SEQ ID NO: 2) of a coding region of GLO-I gene, and (1-2) a base substitution mutation that homozygously causes the mutation (Glu→Ala) of amino acid residue at position 111 in the amino acid sequence (SEQ ID NO: 3) of GLO-I. As described above, it was confirmed that, in the former type of genetic abnormality, the GLO-I activity in blood is decreased by about 50% compared to a healthy subject; and, in the latter type of genetic abnormality, the GLO-I activity in blood is decreased by about 20% compared to a healthy subject (see the Examples).

Detection of such genetic abnormalities can be conducted by known methods such as those described below.

(i) Conducting PCR in the region including a genetic abnormality, followed by detection by SSCP;

(ii) Conducting PCR in the region including a genetic abnormality, followed by detection based on the cleavage pattern of the PCR products cleaved by a restriction enzyme;

(iii) Determining the sequence by subjecting the PCR product to direct sequencing;

(iv) An ASO (Allele Specific Oligonucleotide) method wherein an oligonucleotide that hybridizes to the region including a genetic abnormality is used as a probe, and the probe is hybridized to an individual DNA; and (v) A method wherein an oligonucleotide that hybridizes to the region including a genetic abnormality is used as a probe, and the detection is conducted by using a mass spectrograph, etc.

Specific detection methods include (1-1) a method for identifying insertion of one base (adenine insertion) between adenine at position 79 and cytosine at position 80 in the base sequence (SEQ ID NO: 2) of a coding region of GLO-I gene, and (1-2) a method for identifying mutation (a→c) at position 332, which is one polymorphism, in the base sequence (SEQ ID NO: 2) of a coding region of GLO-I gene that causes the mutation (Glu→Ala) of the amino acid residue at position 111 in an amino acid sequence (SEQ ID NO: 3) of GLO-I gene. The detection methods can be conducted by the steps (a) and (b) described below.

(a) Extracting genomic DNA from a biological sample derived from a subject; and (b) Using the GLO-I gene included in the extracted genomic DNA as a test sample, and identifying the base sequence in the region from position 79 to position 81, or the base at position 332 in the coding region.

In step (b), the GLO-I gene does not have to actually be identified in the extracted genomic DNA. The detection may be conducted by using the extracted genomic DNA as a whole and identifying the base sequence between the base sequence of SEQ ID NO: 4 and that of SEQ ID NO: 5, or the base between the base sequence of SEQ ID NO: 6 and that of SEQ ID NO: 7.

Here, the base sequence shown in SEQ ID NO: 4 corresponds to the base sequence having 200 bases at the 5'-end (upstream) of the base sequence (ac) located at position 79 to position 80 of the base sequence (SEQ ID NO: 2) in the coding region of the base sequence (SEQ ID NO: 1) of human GLO-I gene (Genbank accession number NM 006708). The base sequence shown in SEQ ID NO: 5 corresponds to the base sequence having 300 bases at the 3'-end (downstream) in the base sequence (ac) located at position 79 to position 80 of the base sequence (SEQ ID NO: 2) in the coding region of the base sequence (SEQ ID NO: 1). The base sequences shown in SEQ ID NOs: 6 and 7 respectively correspond to the base sequence having 300 bases at the 5'-end (upstream) and the base sequence having 300 bases at the 3'-end (downstream) in the base (c) at position 332 of the base sequence (SEQ ID NO: 2) in the coding region of the base sequence (SEQ ID NO: 1).

It is preferable that the method (1-1) described above further comprises the step (c-1) described below.

(c-1) Detecting whether adenine is inserted between the adenine at position 79 and the cytosine at position 80 in the base sequence (SEQ ID NO: 2) of a coding region of GLO-I gene.

If the result of the detection indicates that (1-1) adenine is inserted between the adenine at position 79 and the cytosine at position 80 in the base sequence (SEQ ID NO: 2) of a coding region of GLO-I gene, the subject who provided the genomic DNA sample most likely has schizophrenia, or will have schizophrenia in the future.

It is preferable that method (1-2) of the invention further includes step (c-2) described below.

(c-2) Identifying whether the base at position 332 in the base sequence (SEQ ID NO: 2) of a coding region of GLO-I gene is adenine or cytosine.

When the results indicate that (1-2) the base at position 332 is a cytosine-cytosine homozygote (C/C), the subject who provided the genomic DNA sample most likely has schizophrenia or will have schizophrenia in the future.

The methods of the invention make it possible to determine whether the subject has schizophrenia, and the degree of potential risk of onset of schizophrenia. The method of the invention can be automatically conducted using the genetic abnormalities described above as the index, without requiring the judgment of those who have special knowledge, such as medical doctors. Therefore, the method of the invention can also be considered a method for diagnosing schizophrenia.

Note that step (a) (extraction of genomic DNA) and step (b) (identification of the target base) can be conducted by a known method such as, for example, that disclosed in Bruce et al., Geneme Analysis/A Laboratory Manual (vol. 4), Cold Spring Harbor Laboratory, NY., (1999).

Various materials that were isolated from a subject, a clinical specimen, etc. may be used as the sample that is subjected to extraction of genomic DNA in step (a). Examples of usable materials include cells (including cultured cells, but excluding germ cells), tissues (for example, liver, kidney, adrenal gland, uterus, and brain; including cultured tissues), and body fluids (for example, saliva, lymph, respiratory tract mucosa, sperm, sweat, and urine). Leukocytes and mononuclear cells isolated from peripheral blood are preferable as the material, and leukocytes are particularly preferable. These materials can be isolated by a method ordinarily employed in clinical laboratory tests.

For example, when leukocytes are used as the material, leukocytes are isolated from peripheral blood drawn from a subject by an ordinary method. Subsequently, proteinase K and sodium dodecyl sulfate (SDS) are added to the leukocytes to decompose and denature protein contained therein, followed by extraction using phenol/chloroform to obtain genomic DNA (including RNA). If necessary, RNA may be removed using RNase. In addition to the method described above, extraction of genomic DNA may also be conducted by any other method known in the art (for example, a method disclosed in Sambrook J. et al., "Molecular Cloning: A Laboratory Manual ($2^{nd}$ Ed.)" Cold Spring Harbor Laboratory, NY may be employed), by using a commercially available DNA extraction kit, etc. If necessary, GLO-I gene, or DNA that contains GLO-I gene may be isolated. The isolation of such DNA may be conducted using a primer that hybridizes to GLO-I gene, and conducting PCR or the like using the genomic DNA as the template.

In step (b), insertion of a base between position 79 and position 80 in the base sequence (SEQ ID NO: 2) of a coding region of GLO-I gene in the above-obtained extract that contains human genomic DNA is detected, or the type of the base at position 332 in the base sequence (SEQ ID NO: 2) of a coding region of GLO-I gene is identified. The identification of the base can be conducted by isolating the coding region of GLO-I gene from the sample that contains human genomic DNA and directly determining the base sequence thereof so as to determine the presence or absence of a base between position 79 and position 80 in the base sequence, or to identify the type of the base (adenine or cytosine) at position 332.

Examples of the methods for identifying the target base, other than that explained above wherein the gene sequence of the target region is directly identified, include those described below:

A method wherein the genotype is identified using the differences in the cutting patterns of a fragment cleaved by a restriction enzyme, when the polymorphic sequence is in a site recognized by a restriction enzyme (hereunder this method is referred to as RFLP). A method wherein the base is identified based on the hybridization conducted using a probe that specifically hybridizes to a polymorphism (specific examples thereof include a method wherein specific probes are applied on a chip, glass slide or nylon membrane, and the difference in the strength of hybridization to each probe is determined to identify the type of the polymorphism; a method wherein the genotype is identified based on the hybridization efficiencies of specific probes obtained by determining the amounts of the probes decomposed by a polymerase when a double strand is amplified; a method wherein the polymorphism is identified based on the difference in the double-strand-melting temperature determined by following the change with temperature in the fluorescence emitted by a fluorochrome bound to a specific double strand; and a method wherein the genotype is identified by adding sequences complementary to each other to each end of an oligoprobe that specifically binds to a polymorphic site, and determining whether the probe intramolecularly forms a secondary structure or hybridizes to the target region at predetermined temperatures). Another example of the method for identifying the target base is that a method wherein a chain elongation from a template-specific primer is conducted using polymerase, and the bases uptaken in the polymorphic site are identified (specific examples thereof include a method wherein dideoxynucleotides are fluoresceinated, and the fluorescence of each dideoxynucleotide is determined, and a method wherein the uptaken dideoxynucleotides are identified by mass spectrometry). Still another example of the usable method is such that the presence of a base pair complementary or non-complementary to the mutation site is determined using an enzyme, after conducting the elongation using a template-specific primer Typically known methods for detecting genetic polymorphism are described below. However, the methods applicable to the invention are not limited to these methods.

(a) RFLP (Restriction Fragment Length Polymorphism) analysis, (b) PCR-SSCP (Polymerase Chain Reaction-Single Strand Conformation Polymorphism Analysis; Biotechniques, 16, 296-297 (1994), and Biotechniques, 21, 510-514 (1996)), (c) ASO (Allele Specific Oligonucleotide) hybridization method (Clin. Chim. Acta, 189, 153-157 (1990)), (d) direct sequencing method (Biotechniques, 11, 246-249 (1991)), (e) ARMS (Amplification Refracting Mutation System; Nuc. Acids. Res., 19, 3561-3567 (1991); Nuc. Acids. Res., 20, 4831-4837 (1992)), (f) denaturing gradient gel electrophoresis; DGGE (Biotechniques, 27, 1016-1018 (1999)), (g) RNaseA-cleavage method (DNA Cell. Biol., 14, 87-94 (1995)), (h) chemical cleavage method (Biotechniques, 21, 216-218 (1996)), (i) DOL (Dye-labeled Oligonucleotide Ligation) method (Genome Res., 8, 549-556 (1998)), (j) Taq-Man-PCR method (Genet. Anal., 14, 143-149 (1999); J. Clin. Microbiol., 34, 2933-2936 (1996)), (k) invader assay (Science, 5109, 778-783 (1993); J. Biol. Chem., 30, 21387-21394 (1999); Nat. Biotechnol., 17, 292-296 (1999)), (l) MALDI-TOF/MS (Matrix Assisted Laser Desorption-time of Flight/Mass Spectrometry; Genome Res., 7, 378-388 (1997); Eur. J. Clin. Chem. Clin. Biochem., 35, 545-548 (1997)), (m) TDI (Template-directed Dye-terminator Incorporation; Proc. Natl. Acad. Sci. USA, 94, 10756-10761 (1997)) assay, (n) Molecular Beacon-based method (Nat. Biotechnol., 1, p49-53 (1998); Gene & Medicine, 4, pp. 46-48 (2000)), (o) Dynamic Allele-Specific Hybridization; DASH (Nat. Biotechnol., 1. pp. 87-88 (1999); Gene & Medicine, 4, 47-48 (2000), (p) Padlock Probe assay (Nat. Genet., 3, pp. 225-232 (1998); Gene & Medicine, 4, pp. 50-51 (2000)), (q) UCAN method (see homepage of Takara Shuzo Co., Ltd,: http://www.takara.co.jp), (r) DNA chip or DNA microarray method (SNP Idenshi Tagata no Sentryaku "Strategy for SNP genetic polymorphism"; Kenichi MATSUBARA, Yoshiki SAKAKI, Nalayama-shoten, pp. 128-135), (s) ECA method (Anal. Chem., 72, 1334-1341, (2000)).

Typical methods for detecting genetic polymorphism are described above. However, the methods for detecting genetic polymorphism applicable to the schizophrenia diagnostic method of the invention are not limited to these, and other known methods or those to be developed in the future are also usable. In the genetic abnormality detection method of the invention, these genetic polymorphism detection methods may be used singly, or in combination.

If the method of the invention finds that a subject has schizophrenia or a relatively high risk to have schizophrenia in the future, the subject will be informed of the fact so that appropriate countermeasures for treating, alleviating or preventing the onset of schizophrenia can be performed. Therefore, the invention provides a diagnostic method that is very useful in treating schizophrenia, alleviating schizophrenia, preventing the onset thereof, or inhibiting the development (progress) of schizophrenia, at an early stage.

The method of the invention is not limited to that by which a genetic abnormality is detected based on the base sequence, and may include a method that directly detects a mutation (Glu→Ala) of amino acid residue at position 111 in an amino acid sequence (SEQ ID NO: 3) of GLO-I that was generated due to a genetic abnormality. An example of such a method is that by which the presence of the amino-acid mutation in GLO-I gene expression product (such as mRNA and GLO-I) of a subject is detected. Specific examples of such methods are described below:

A method by which the sequence of the GLO-I gene expression product is identified; Western blotting method, dot-blotting method, immunoprecipitation assay, enzyme-linked immunosorbent assay (ELISA), and immunofluorescence assay, wherein an antibody to GLO-I or to mutated GLO-I (Glu111Ala) can be used; and a method wherein the activity generated (or lost) due to the mutation (Glu→Ala) of amino acid residue at position 111 in the amino acid sequence of GLO-I is measured.

(2) Measurement of Expression Level or Activity of Glyoxalase I in Biological Sample Such measurement is preferably conducted using blood, and particularly preferably using serum or hemocyte as the material.

The expression level of GLO-I can be measured by a known immunological technique, such as Western blotting, EIA, RIA, FIA, chemiluminescence immunoassay, and ECLIA, usually using an antibody to GLO-I (polyclonal antibody or monoclonal antibody). Western blotting using a monoclonal antibody to GLO-I is preferable. Specifically, a test sample is treated with mercaptoethanol, and then electrophoresed on SDS-polyacrylamide gel. Subsequently, protein contained therein is transferred onto a PVDF membrane, followed by reaction with a GLO-I antibody and with a labeled second antibody to develop a color to visualize the protein. In Western blotting, by using β-actin or like housekeeping gene-derived protein as an internal standard substance if necessary, the amount of mRNA in GLO-I can be determined more accurately. An antibody to GLO-I can be prepared by a conventional method, and is also commercially available (for example, a GLO1 polyclonal antibody, manufactured by Abnova Corporation/Taipei City 114 Taiwan, Catalog#: H00002739-A01).

The GLO-I activity can be measured by any methods known in the art without limitation. For example, the method disclosed by McLellan et al. (McLellan AC, Thornalley PJ: Glyoxalase activity in human red blood cells fractioned by age. Mech Ageing Dev 48: 63-71, 1989) as explained in Example 1 may be employed. Specifically, the method is such that destructed erythrocytes are reacted with hemithioacetal generated from methylglyoxal and glutathione, and the amount of the resulting S-D-lactoylglutathione is measured to evaluate the GLO-I activity in erythrocyte. In this method, one unit indicates the GLO-I activity with which $10^6$ erythrocytes can produce 1 μmol of S-D-lactoylglutathion per one minute.

To be more specific, the diagnostic method of the invention can be performed in the following manner. Using the above-described method, the expression or activity level of GLO-I in a biological sample derived from a subject is measured, the measurement result is then compared to the expression level (control expression level) or activity level (control activity) of GLO-I in a healthy subject to evaluate whether the measurement result is higher or lower than the control amount. In this method, if the expression or activity level of GLO-I is lower than the control expression level or the control activity, the subject is diagnosed as having schizophrenia.

(3) Measurement of the Amount of Carbonyl Compound or Carbonyl-Modified Protein in Biological Sample The measurement is preferably conducted using blood, and particularly preferably using serum or plasma as a material.

Examples of carbonyl compounds subjected to the measurement include arabinose, GO, MGO, 3-DG, glycolaldehyde, dehydroascorbic acid, hydroxynonenal, malondialdehyde, acrolein, 5-hydroxymethylfurfural, formaldehyde, acetaldehyde, lepulic acid, and furfural. The amounts thereof can be measured using reference standards having ordinary known concentrations, and by conducting high-performance chromatography (HPLC), gas chromatography/mass spectrometry (GC/MS), or like instrumental analysis.

Similarly, the amounts of carbonyl-modified proteins (such as AGEs) formed by the reaction between these carbonyl compounds and biological proteins (hereunder these carbonyl-modified proteins may be referred to as "AGEs") can also be measured by conducting HPLC, GC/MS or like instrumental analysis using reference standards having ordinary known concentrations. Note that AGEs are an assembly of two or more structures (AGEs structure). Therefore, measurement of the amount of AGE can be conducted by measuring the amount of AGEs structure. Examples of the AGEs structure include pentosidine, crossline, pyrropyridine, vesperlysines A, B, and C, glyoxal-lysine dimmer (GOLD), and methylglyoxal-lysine dimmer (MOLD) (these are fluorescent substances); and Nε-(carboxymethyl)lysine (CML), Nε-(carboxyethyl)lysine (CEL), argpyrimidine; pyrraline; imidazolone, and GA-pyridine (these are non-fluorescent substances). Among these, pentosidine is preferable.

Pentosidine is a fluorescent substance that is stable during acidic hydrolysis, and that has a structure wherein pentose cross-links equimolar lysine residue and arginine residue. Pentosidine is known to accumulate in human skin in correlation with aging or the onset of diabetes. It is reported that the amount of pentosidine remarkably increases due to the onset of diabetes or at the terminal stage of nephropathy. The amount of pentosidine contained in blood and like proteins can be measured by HPLC using its fluorescence (Ex: 335 nm, Em: 385 nm), after being subjected to acidic hydrolysis, as an index. The amount of pentosidine can also be measured by immunochemistry methods using a monoclonal antibody to pentosidine (for example, ELISA, particularly sandwich ELISA and competitive ELISA). The monoclonal antibodies and polyclonal antibodies to pentosidine can be prepared by a conventional method. More conveniently, they are also commercially available (for example, products manufactured by Trans Genic, Inc., and products manufactured by Fushimi Pharmaceutical Co., Ltd.). Antibodies to AGEs structure, such as proteins modified with carboxymethyllysine, malondialdehyde and hydroxynonenal are also commercially available.

Competitive ELISA can be conducted in the following manner. A standard AGEs structure and a sample (plasma) that was pretreated with a proteolytic enzyme are added to a microplate on which pentosidine and like AGE structures are solidified; antibodies to the AGEs structures are added to and reacted therewith, followed by washing; an enzyme solution is added thereto, followed by re-washing; and a color coupler is added to measure the absorbance. The procedure has been established as a blood chemical analysis of pentosidine, and can be easily conducted using a quantification kit such as "FSK pentosidine" (product name, manufactured by Fushimi Pharmaceutical Co., Ltd.). The amount of the pentosidine and like AGEs accumulated in the skin can be easily measured using a commercially available AGE Reader (manufactured by DiagnOptics).

More specifically, the diagnostic method of the invention can be conducted by measuring the amount of carbonyl compounds or carbonyl-modified proteins (such as AGEs) in a biological sample derived from a subject in the manner as described above, comparing the measurement result to the amount of that of a healthy subject (control amount), and evaluating whether the measurement result is higher or lower than that of a healthy subject. In this method, the subject is diagnosed as having schizophrenia, or as likely developing schizophrenia in the future based on the measurement result, i.e., having a higher amount of carbonyl compound or AGEs than the control amount as an index. The amount of pentosidine and like AGE structures is known to increase in the living body along with age. Therefore, it is preferable that the sample of the healthy subject be derived from someone who is almost the same age as the subject.

(4) Measurement of the Amount of Pyridoxal and Homocysteine in Biological Sample (4)

The measurement can be conducted by a known method, preferably using blood, and particularly preferably using serum or plasma. For example, the measurement can be conducted by employing HPLC, GC/MS or like instrumental analysis using reference standards having known concentrations.

More specifically, the diagnostic method of the invention can be conducted by, after measuring the amount of pyridoxal in a biological sample derived from a subject, comparing the measuring result to that of a healthy subject (control amount), and evaluating whether the result is higher or lower than that of the control amount. In this case, the subject is diagnosed as having schizophrenia, or most likely will have schizophrenia in the future based on the measurement result, i.e., having a lower pyridoxal amount than that of the control amount as an index. The pyridoxal concentration in serum of a healthy subject is 6.0 to 40.0 ng/ml (male) or 4.0 to 19.0 ng/ml (female).

The pyridoxal value is related to the homocysteine value. Specifically, when the pyridoxal value is lowered, the homocysteine value tends to increase. Therefore, when the pyridoxal amount is measured, it is recommended to also measure the homocysteine amount so as to confirm the accuracy and correctness of the measurement of the pyridoxal amount. In this case, if the pyridoxal amount in the subject is lower than the control amount, and the homocysteine amount in the subject is higher than the homocysteine amount (control amount) of a healthy subject, the subject most likely has schizophrenia, or will have schizophrenia in the future. The homocysteine amount can be measured by a conventional method. For example, the measurement can be conducted by employing HPLC, GC/MS or like instrumental analysis using reference standards having known concentrations. The serum concentration of homocysteine in a healthy subject is 3.7 to 13.5 nmol/ml.

The diagnostic method of the invention can be carried out by conducting at least one of the measurements of (1) to (4) described earlier. Alternatively, the diagnostic method of the invention can be carried out by combining two or more measurements, preferably three or more measurements, and more preferably four measurements of (1) to (4) or more. By combining a plurality of measurements, the accuracy of the diagnosis can be enhanced. Either (1) detecting genetic abnormality of GLO-I gene, or (3) measuring the amount of a carbonyl compound or a carbonyl-modified protein is preferably conducted. More preferably, (1) is combined with (3), or (3) is combined with (2) when measuring the expression or activity level of glyoxalase I. The diagnostic method of the invention can also be conducted in combination with conventional subjective examinations or diagnostic methods (for example, BPRS score based on the criteria defined by ICD or DSM).

The diagnostic method of the invention makes it possible to objectively diagnose whether a subject has schizophrenia using a biological sample. Therefore, the method is usable as a piece of supplementary evidence to determine whether a subject has legal capacity, and as expert psychiatric testimony for purposes other than the determination of legal capacity.

The diagnostic method of the invention makes it possible to determine the cause and desirable treatment for each patient, assess the condition of the patient and conduct follow-ups, evaluate the therapeutic effect, predict prognoses, and distinguish patients with other diseases, including psychiatric disorders other than schizophrenia. In particular, the method of the invention can differentiate patients with schizophrenia caused by carbonyl stress due to reduction of GLO-I activity. Therefore, the method of the invention can accurately select the schizophrenia patients for whom a carbonyl stress elimination therapy using a carbonyl scavenger, AGEs formation inhibitor or the like is effective. This provides an accurate and effective treatment to schizophrenia patients.

II. Schizophrenia Diagnostic Reagent or Device, and Use Thereof

The invention provides a reagent and device for use in the method for diagnosing schizophrenia described above. The reagent and device can be suitably selected depending on the criteria used in schizophrenia diagnosis.

(1) Diagnostic Reagent Used when Presence of Genetic Abnormality Of GLO-I Gene is Used as Diagnostic Index.

When (1) the presence of genetic abnormality of GLO-I gene is used as a diagnostic index, the below-explained probes or primers (these may be labeled or immobilized on a solid phase) may be used as the diagnostic reagents. The reagent may be a kit including, in addition to the above-mentioned probes or primers, if necessary, reagents for hybridization, labels for probes, agents for detecting labeled bodies, buffer solutions, other reagents, and device or the like necessary for the diagnosis of the invention.

(1-1) Probe

In the detection of insertion of adenine between position 79 and position 80, or mutation from adenine to cytosine at position 332 in the base sequence (SEQ ID NO: 2) of a coding region of GLO-I gene, an oligo- or polynucleotide that detects the base sequence or the base by hybridizing specifically to the oligo- or polynucleotide that contains the base sequence from position 79 to position 80, or a base at 332 position in the coding region of the gene is used. Such an oligo- or polynucleotide is designed to have 16 to 500 bases, preferably 20 to 200 bases, and more preferably 20 to 50 bases to hybridize specifically to a continuous genetic region having the above-mentioned base length, wherein the area includes the base sequence (from 79 position to 80 position in the coding region (SEQ ID NO: 2)) or a base (at position 332 in the coding region (SEQ ID NO: 2)) in GLO-I gene (SEQ ID NO: 1).

Here, the expression "hybridizes specifically" means that the oligo- or polynucleotide does not significantly cross-hybridize to other DNAs under ordinary hybridization conditions, preferably stringent hybridization conditions (for example, the conditions disclosed in Sambrook et al., Molecular Cloning, Cold Spring Harbour Laboratory Press, New York, USA, $2^{nd}$ edition, 1989). It is preferable that the oligo- or polynucleotide comprise a base sequence complementary to the genetic region comprising the base sequence or the base detected above. However, it does not have to be completely complementary, as long as the above-described specific hybridization is obtained.

Specific examples of the above-described oligo- or polynucleotides are those having 16 to 500 bases that hybridize to oligo- or polynucleotide having 16 to 500 continuous bases that include the base sequence (ac) from 79 position to 80 position in the base sequence (SEQ ID NO: 2) of a coding region of GLO-I gene (when the polynucleotide is RNA, the base "t" in the base sequence is replaced with "u"), or to oligo- or polynucleotide having 16 to 500 continuous bases that include the base at 332 position in the base sequence (SEQ ID NO: 2) of a coding region of GLO-I gene (when the polynucleotide is RNA, the base "t" in the base sequence is replaced with "u").

The oligo- or polynucleotide is designed as an oligo- or polynucleotide "probe" that hybridizes specifically to oligo- or polynucleotide comprising the region from position 79 to position 80, or the base at position 332 in the base sequence (SEQ ID NO: 2) of a coding region of GLO-I gene, so that the diagnosis as to whether a subject has schizophrenia or has potential risk of onset of schizophrenia can be conducted. These oligo- or polynucleotides can be synthesized based on the base sequence (SEQ ID NO: 1) of GLO-I gene by a conventional method using, for example, a commercially available nucleotide synthesizer.

More preferably, the probe may be labeled with a radioactive substance, fluorescent substance, chemiluminescence substance, or enzyme as described later.

The probe (oligo- or polynucleotide) may be used after being immobilized on any solid phase. Therefore, the present invention provides the probe (oligo- or polynucleotide) in the form of an immobilized probe (for example, a gene chip, cDNA microarray, oligodeoxynucleotide array, membrane filter and the like on which the probe is immobilized). The probe is desirably used as a DNA chip for diagnosing schizophrenia.

There is no limitation to the solid phase used for immobilization, as long as the oligo- or polynucleotide can be immobilized. Specific examples thereof include glass plates, nylon membranes, microbeads, silicon chips, capillary tubes, other substrates, etc. Immobilization of oligo- or polynucleotide on a solid phase may be conducted by placing pre-synthesized oligo- or polynucleotides on a solid phase, or synthesizing objective oligo- or polynucleotides on a solid phase. The immobilization method may be selected from those known in the art (for example, in situ synthesis of oligonucleotide using photolithography (provided by Affymetrix) and ink jet (provided by Rosetta Inpharmatics), depending on the type of the immobilized probe); for example, in the case of a DNA microarray, commercially available spotters (such as a spotter manufactured by Amersham Corporation) may be used.

When TaqMan PCR assay (Livak K J. Gene Anal 14, 143 (1999), Morris T et al., J Clin Microbiol 34, 2933 (1996)), which is a type of ASO, is employed, an oligonucleotide having about 20 bases that is complementary to the region comprising the base sequence from position 79 to position 80 or a base at position 332 is prepared as a probe. The probe has a 5'-end labeled with fluorochrome and a 3'-end labeled with a quencher; it hybridizes specifically to the sample DNA, but does not emit light in its regular state. The probe is detected by fluorochrome liberated by cleavage of fluorochrome at the 5'-end due to the base extension reaction from the upstream of the PCR primer separately added. In the invader method (Lyamichev V. et al., Nat Biotechnol 17, 292 (1999)), which is another type of ASO, two oligonucleotides complementary to the sequences (two types, i.e., at the 3'-end and at the 5'-end) adjacent to the mutated site are prepared as the probes. The detection is conducted using a third probe that is unrelated to either of the two probes or the sample.

(1-2) Primer

The present invention provides an oligonucleotide that can be used as a primer for specifically amplifying the sequence region including the mutation (base insertion between position 79 and position 80, or mutation from adenine to cytosine at position 332) in the base sequence (SEQ ID NO: 2) of a coding region of GLO-I gene. The primer (oligonucleotide) is designed as an oligonucleotide having 15 to 35 bases, preferably about 18 to 30 bases that hybridizes specifically to a portion of continuous oligo- or polynucleotides comprising the nucleotides from position 79 to position 80, or at position 332 in the base sequence of the coding region in GLO-I gene so as to specifically amplify the oligo- or polynucleotide. The length of the oligo- or polynucleotide to be amplified depends on the detection method, and is generally 15 to 1,000 bases, preferably 20 to 500 bases, and more preferably 20 to 200 bases.

Specific examples of the primers include oligonucleotides having 15 to 35 bases, and preferably about 18 to 30 bases that hybridize specifically to continuous oligo- or polynucleotides (when the polynucleotide is RNA, the base "t" in the base sequence is replaced with "u") with 16 or more bases comprising the nucleotide from position 79 to position 80 in human base sequence (SEQ ID NO: 2) of a coding region of GLO-I gene for specifically amplifying the oligo- or polynucleotides; and oligonucleotides having 15 to 35 bases, and preferably about 18 to 30 bases that hybridize specifically to continuous oligo- or polynucleotides (when the polynucleotide is RNA, the base "t" in the base sequence is replaced with "u") with 16 or more bases comprising the nucleotide at 332 position in human base sequence (SEQ ID NO: 2) of a coding region of GLO-I gene for specifically amplifying the oligo- or polynucleotides.

These oligonucleotides can be synthesized by a conventional method using a commercially available nucleotide synthesizer based on the known base sequence (SEQ ID NO: 1) of GLO-I gene.

(1-3) Labeling Product

The probes or primers of the invention described above include those labeled with a labeling substance suitable for detecting genetic abnormality, such as a fluorochrome, enzyme, protein, radioactive isotope, chemiluminescent substance, or biotin.

The fluorochromes desirably used in the invention are those that can label nucleotide to detect or measure the amount of nucleic acid. Specific examples thereof include, but are not limited to, HEX (4,7,2',4',5',7'-hexachloro-6-carboxylfluorescein, green fluorochrome), fluorescein, NED (product name, manufactured by Applied Biosystems Inc., yellow fluorochrome), 6-FAM (product name, manufactured by Applied Biosystems Inc., yellow green fluorochrome), and rhodamin and its derivative (for example, tetramethylrhodamine (TMR)). The method for labeling nucleotide with a fluorochrome can be suitably selected from known labeling methods (see Nature Biotechnology, 14, 303-308 (1996)). Commercially available fluorescence labeling kits may be used (for example, oligonucleotide ECL 3'-oligonucleotide labeling system manufactured by Amersham Pharmacia).

The primer of the invention includes those to which linker sequences for detecting genetic abnormalities are added to its ends. An example of the linker sequences is a flap sequence (a sequence completely unrelated to the sequence in the vicinity of a polymorphism) that is added to the 5'-end of the oligonucleotide used in the invader method described above.

When PCR-direct sequencing is employed to detect genetic abnormalities, in detecting the base sequence from position 79 to position 80 in the base sequence (SEQ ID NO: 2) of a coding region of GLO-I gene, an oligonucleotide comprising the base sequence shown in SEQ ID NO: 8 is preferably used as the forward primer, and the base sequence shown in SEQ ID NO: 9 is preferably used as the reverse primer. In detecting the base sequence comprising the base at position 332 in the base sequence (SEQ ID NO: 2) of a coding region of GLO-I gene, an oligonucleotide comprising the base sequence shown in SEQ ID NO: 10 is preferably used as the forward primer, and the base sequence shown in SEQ ID NO: 11 is preferably used as the reverse primer.

The probes or primers (may be labeled) described above can be used as a reagent for diagnosing schizophrenia, or for determining the risk of onset of schizophrenia.

(2) Reagent When Expression Level of GLO-I is Used as Diagnostic Indicator

Examples of the reagents (2) when the expression level of GLO-I is used as the diagnostic index include GLO-I antibodies (polyclonal antibody and monoclonal antibody). Examples of the reagents when the GLO-I activity is used as the diagnostic index include reactional substrates (such as hemithioacetal) in GLO-I. In the former case, in addition to the GLO-I antibodies, reagents (such as a labeled second antibody, SDS-PAGE, and microplate) used in conducting various immunological procedures, such as Western blotting, EIA, RIA, FIA, chemiluminescence immunoassay, and ECLIA may also be used.

(3) Reagent or Device Used when Amount of Carbonyl Compound or Carbonyl-Modified Protein (such as AGEs) is Used as Diagnostic Index Examples of the reagents when (3) the amount of carbonyl compound or AGEs is used as a diagnostic index include (a) carbonyl compound or AGEs with a known concentration, and (b) AGE antibodies that may be labeled. Specific examples of the carbonyl compound and AGE antibodies are those mentioned above. When pentosidine is used as the (3) carbonyl-modified protein, the amount of pentosidine in the skin can be used as the diagnostic indicator, as described earlier. In this case, a commercially available AGE Reader that can measure the amount of pentosidine in the skin is suitably used as the schizophrenia diagnostic device. In other words, the invention provides an AGE Reader usable as diagnostic device for diagnosing schizophrenia. The device may have a document indicating that the device is usable in diagnosing schizophrenia. In this case, the document may include information regarding the diagnostic criteria for schizophrenia, and/or instructions for the diagnosis.

(4) Reagent when Amount of Pyridoxal is Used as Diagnostic Index and (5) Reagent when Amount of Homocysteine are Used as Diagnostic Index Examples of the reagents when (4) the amount of pyridoxal is used as the diagnostic indicator include (a) pyridoxal with a known concentration, and (b) pyridoxal amount measurement reagents. Examples of the reagents when (5) the amount of homocysteine is used as the diagnostic indicator include (a) homocysteine with a known concentration, and (b) homocysteine amount measurement reagents.

III. Schizophrenia Therapeutic or Ameliorating Agent

One of the major features of the therapeutic or ameliorating agent for schizophrenia of the invention is that it contains a carbonyl scavenger or an AGEs formation inhibitor as the active ingredient.

(1) Carbonyl Scavenger

The carbonyl scavenger targeted by the invention is a substance effective in reducing the amount of carbonyl compound (for example, arabinose, GO, MGO, 3-DG, glycolaldehyde, dehydroascorbic acid, hydroxynonenal, malondialdehyde, acrolein, 5-hydroxymethylfurfural, formaldehyde, acetaldehyde, lepulic acid, and furfural) formed from sugar, lipid, or amino acid in the body due to oxidative stress or the like. The mechanism is not particularly limited; examples thereof include that by which the production of carbonyl compound is suppressed, and that by which the amount of carbonyl compound in the body is reduced by capturing the produced carbonyl compound. Examples of the carbonyl scavengers having such mechanisms include pyridoxamine or pharmaceutically acceptable salts or esters thereof and various carbonyl scavengers that can also be widely used.

(2) AGEs Formation Inhibitor

The carbonyl compounds mentioned above are highly reactive and non-enzymatically react with proteins in the body to produce advanced glycation end products: AGEs (carbonyl stress). AGEs are an assembly of a plurality of structures. Known examples of such structures include pentosidine, crossline, pyrropyridine, vesperlysines A, B, and C, glyoxal-lysine dimmer (GOLD), and methylglyoxal-lysine dimmer (MOLD) (these are fluorescent substances); and $N\epsilon$-(carboxymethyl)lysine (CML), $N\epsilon$-(carboxyethyl)lysine (CEL), argpyrimidine, pyrraline, imidazolone, and GA-pyridine (these are non-fluorescent substances).

The AGEs formation inhibitor targeted by the invention has an effect of inhibiting the formation of AGEs in the body. Here, "inhibiting the formation of AGEs" may be achieved by the action of trapping carbonyl compounds or by inhibiting the reaction of forming carbonyl-modified proteins (AGEs), and there is no limitation to the mechanism thereof as long as the formation of AGEs can eventually be suppressed.

Whether the objective compound has the AGEs formation-inhibition effect can be determined based on test (i) or (ii) described below.

(i) Plasma is collected from a non-diabetic renal failure patient who undergoes dialysis, the compound to be tested is added to the plasma, and the amount of pentosidine produced after a certain period of time is measured using pentosidine, which is a typical AGE, as an index.

(ii) Phenylalanine binds to an OH radical under the presence of hydroxy radical to generate o- or m-tyrosin. Tyrosin reacts with a NO radical under the presence of peroxynitrite to generate nitrotyrosin. It is also known that radicals cause kidney disorders in living bodies. Accordingly, the radical-capturing ability of the tested compound in a phenylalanine-radical reacting system is determined.

It is preferable that the objective compound does not cause vitamin $B_6$ deficiency. Whether the objective compound causes vitamin $B_6$ deficiency can be confirmed by either test (a) or (b) described below.

(a) To a solution of vitamin $B_6$, the compound to be tested is added; and, after a certain period of time, the amount of vitamin $B_6$ remaining is determined.

(b) To a normal rat, the compound to be tested is administered; and, after a certain period of time, the presence or absence of vitamin $B_6$ deficiency is determined.

There is no limitation to the AGEs formation inhibitor of the invention, as long as it exhibits an AGEs formation-inhibition effect. Examples of the active ingredients thereof include a compound containing a substituent that inhibits binding of vitamin $B_6$ molecules to the 4-position of 1-substituted-, unsubstituted-3-substituted- or unsubstituted-2-pyrazolin-5-one in free form or salt form (the substituent may be one derived from vitamin $B_6$ molecules), or an intramolecular rearrangement product thereof. These compounds can eventually inhibit the formation of AGEs, regardless of whether they are in vivo, ex vivo and/or in vitro. Examples of such compounds include edaravone (3-methyl-1-phenyl-2-pyrazolin-5-one) represented by Formulae (1) and (2) below, and analogues thereof. Examples of the active ingredients of the AGE formation inhibitor of the invention includes a phenylene derivative represented by Formulae (I) and (II) below.

(2-1) Edaravone and Analogues Thereof

Edaravone and analogues thereof in free form or salt form usable in the invention are compounds represented by Formula (1):

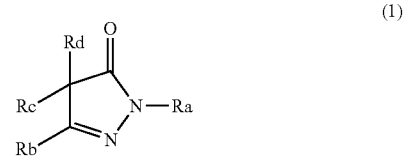

(1)

or compounds represented by the formula (2):

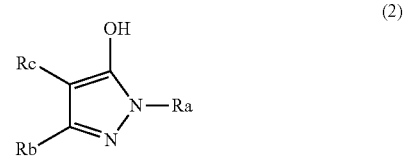

(2)

wherein Ra is a substituted or unsubstituted aromatic group, each of Rb, Rc, and Rd is a hydrogen atom or a monovalent organic group, Rb and Rc may be combined to form a fused ring, or Rc and Rd may be combined to form a divalent organic group.

In Formula (1) or (2), Ra is a hydrogen atom, or a substituted or unsubstituted aromatic group (including heterocyclic group). The "aromatic group" includes those having 20 or fewer annular atoms (oxygen, sulfur, nitrogen or like hetero atom may be included as long as its total number does not exceed four). In particular, aryls (for example, phenyl and naphthyl) having 6 to 10 annular atoms are preferable.

The substituent is at least one member selected from the group consisting of lower alkyl, lower alkenyl, lower alkoxy, lower alkenyloxy, lower alkanoyl, halo(lower)alkyl, carboxyl, lower alkoxycarbonyl, carboxy(lower)alkyl, halo(for example, chlorine, bromine, iodine, and fluorine)nitro, amino, lower alkylamino, di(lower)alkylamino, lower alkanoylamino, hydroxyl, thiol, hydroxysulfonyl, aminosulfonyl, aryl(lower)alkanoyl, aryloxyamino, aryl, aryl(lower)alkyl, cyclo(lower)alkyl, cyclo(lower)alkenyl, cyclo(lower)alkyl(lower)alkyl, and 3-7 membered heterocyclic groups (for example, oxadiazolyl and thiadiazolyl). The number of the substituents is not limited, but generally does not exceed three.

Examples of the substituted or unsubstituted aromatic groups represented by Ra include: phenyl, naphthyl, o-, m-, or p-lower alkylphenyl (for example, o-methylphenyl, p-methylphenyl and p-ethylphenyl), o-, m-, or p-lower alkoxyphenyl (for example, o-, m-, or p-methoxypheny, and o-, m- or p-ethoxyphenyl), o-, m-, or p-aminophenyl, o-, m-, or p-nitrophenyl, o-, m-, or p-halophenyl (for example, o-, m-, or p-chlorophenyl, o-, m-, or p-fluorophenyl), o-, m-, or p-halo(lower)alkylphenyl (for example, o-, m-, or p-trifluoromethylphenyl), o-, m-, or p-sulfamoylphenyl, o-, m-, or p-carboxyphenyl, o-, m-, or p-lower alkoxycarbonylphenyl (for example, o-, m-, or p-carbomethoxyphenyl, o-, m-, or p-carboethoxyphenyl, o-, m-, or p-isopropoxycarbonylphenyl), o-, m-, or p-lower alkanoylphenyl (for example, o-, m-, or p-acetylphenyl), di(lower)alkylphenyl (for example, 3,4-dimethylphenyl), dihydroxyphenyl (for example, 2,4-dihydroxyphenyl), 2-amino-4-carboxyphenyl, 3-amino-5-carboxyphenyl, 3-lower alkoxy-4-hydroxyphenyl (for example, 3-methoxy-4-hydroxyphenyl), and 3-carboxy-4-halophenyl (for example, 3-carboxy-4-chlorophenyl).

Each of Rb, Rc, and Rd is a hydrogen atom or a monovalent organic group. The "monovalent organic group" includes substituted or unsubstituted hydrocarbon group, halo group, nitro group, amino group, hydroxy group, thiol group, carboxy group, carboxy(lower)alkyl group, lower alkoxycarbonyl group, formyl group, lower alkanoyl group, lower alkylamino group, di(lower)alkylamino group, lower alkanoylamino group, aryl(lower)alkanoyl group, aryloxyamino group, sulfonic acid group, and 3-7 membered heterocyclic groups. Examples of the "hydrocarbon groups" include chain or cyclic aliphatic groups, and alicyclic or aromatic hydrocarbon groups having 30 or fewer carbon atoms (preferably not exceeding eight). Specifically, alkyl group, alkenyl group, alkynyl group, cycloalkyl group, cycloalkenyl group, aryl group and the like are included. The "3-7 membered heterocyclic groups" are those containing 3 or fewer hetero atoms as annular atoms, and specific examples thereof include piperidino, morpholino, and thiamorpholino. The types and number of substituents are the same as those described in Ra.

Rb and Rc may be combined to form a fused ring. The fused ring is preferably a 5- or 6-membered saturated carbocyclic (specifically, Rb+Rc=trimethylene or tetramethylene), and optionally contains a substituent. Rc and Rd may be combined to form a divalent organic group. The divalent organic groups include methylene-type organic groups and spiro-type organic groups. Examples of methylene-type organic groups include phenylmethylene, phenyl alkenyl methylene, quinolylmethylene, furylmethylene, diazolylmethylene, aminomethylene, di(lower)alkylaminomethylene, pyridylmethylene, and thiophenylmethylene; these organic groups may optionally contain a substituent, if necessary. The types and number of substituents that may be contained in the fused ring or divalent organic group may be the same as those explained in Ra.

The term "lower" used in relation to alkyl, alkoxy, alkanoyl, etc. usually indicates groups having no more than eight carbon atoms, and preferably no more than five carbon atoms.

Specific examples of compound (1) or (2) of the invention are as follows:

1. 2-(3-amino-5-oxo-1-phenyl-4,5-hydro-1H-pyrazol-4-yl)-2-oxo-N-phenyl-acetamide
2. 2-(3-amino-5-oxo-1-phenyl-4,5-hydro-1H-pyrazol-4-yl)-2-oxo-N-thiazol-2-yl-acetamide
3. 2-(3-amino-5-oxo-1-phenyl-4,5-hydro-1H-pyrazol-4-yl)-2-oxo-acetamide
4. 2-(3-amino-5-oxo-1-phenyl-4,5-hydro-1H-pyrazol-4-yl)-N-(3,4-dimethyl-phenyl)-4-oxo-butyramide
5. 2-(4-amino-phenyl)-4-(2-hydroxy-ethyl)-5-methyl-2,4-hydro-pyrazol-3-one
6. 5-amino-2-phenyl-4-(1-phenyl-1H-tetrazol-5-ylsulfanyl)-2,4-dihydro-pyrazol-3-one
7. 3-(3-methyl-5-oxo-1-penyl-4,5-dihydro-1H-pyrazol-4-yl)-propionic acid
8. N-(3-methyl-5-oxo-1-phenyl-4,5-dihydro-1H-pyrazol-4-yl)-acetamide
9. 4-[(5-hydroxy-3-methyl-1-phenyl-1H-pyrazol-4-yl)-phenyl-methyl]-5-methyl-2-phenyl-2,4-dihydro-pyrazol-3-one
10. 2-phenyl-3a,4,5,6-tetrahydro-2H-cyclopentapyrazol-3-one
11. 4-methyl-N-(3-methyl-5-oxo-1-phenyl-4,5-dihydro-1H-pyrazol-4-yl)-benzenesulfonamide
12. N-(3-methyl-5-oxo-1-phenyl-4,5-dihydro-1H-pyrazol-4-yl)-acetamide
13. 5-methyl-2-(3-nitro-phenyl)-4-(1-phenyl-1H-tetrazol-5-ylsulfanyl)-2,4-dihydro-pyrazol-3-one
14. N-[5-oxo-1-phenyl-4-(1-phenyl-1H-tetrazol-5-ylsulfanyl)-4,5-dihydro-1H-pyrazol-3-yl]-benzamide
15. 4-(hydroxy-phenyl-methyl)-2-phenyl-5-trifluoromethyl-2,4-dihydro-pyrazol-3-one
16. 4-(1-hydroxyimino-ethyl)-2,5-diphenyl-2,4-dihydro-pyrazol-3-one
17. 5,5'-dimethyl-2,2'-diphenyl-2,4,2',4'-tetrahydro-[4,4']bipyrazole-3,3'-dione
18. 2-(4-chloro-phenyl)-4-ethyl-5-methyl-2,4-dihydro-pyrazol-3-one
19. 4-[4-(4-methoxy-phenyl)-thiazol-2-ylsulfanyl]-5-methyl-5-phenyl-2,4-dihydro-pyrazol-3-one
20. 4-(2-oxo-2-phenyl-ethyl)-2-phenyl-5-propyl-2,4-dihydro-pyrazol-3-one
21. 5-methyl-2-phenyl-4-(4-p-toluoyl-thiazol-2-ylsulfanyl)-2,4-dihydro-pyrazol-3-one
22. 2-(4-fluoro-phenyl)-4-[[1-(4-fluoro-phenyl)-5-hydroxy-3-methyl-1H-pyrazol-4-yl]-(2-hydroxy-phenyl)-methyl]-5-methyl-2,4-dihydro-pyrazol-3-one
23. N-(3,4-dimethyl-phenyl)-2-(3-methyl-5-oxo-1-phenyl-4,5-dihydro-1H-pyrazol-4-yl)-2-oxo-acetamide 24. 5-(4-chloro-benzoyl)-4,4-dihydroxy-2-phenyl-2,4-dihydro-pyrazol-3-one
25. sodium 4-hydroxy-3-methyl-5-oxo-1-phenyl-4,5-dihydro-1H-pyrazole-4-sulfonate
26. 5-methyl-4,4-dimorpholine-4-yl-2-phenyl-2,4-dihydropyrazol-3-one
27. sodium 3-benzoylamino-4-hydroxy-5-oxo-1-phenyl-4,5-dihydro-1H-pyrazole-4-sulfonate
28. 3-methyl-1-phenyl-5-oxo-4-spiro(3-oxo-2,3-dihydrobenzo[b]thiophen-2-yl)-4,5-dihydro-1H-pyrazole
29. 4,4,5-trimethyl-2-phenyl-2,4-dihydro-pyrazol-3-one
30. 4,10-dimethyl-2,8,11-triphenyl-2,3,8,9-tetraza-dispiro[4.0.4.1]undeca-3,9-diene-1,7-dione
31. 2-(2-chloro-phenyl)-4-(3-ethoxy-4-hydroxy-benzylidene)-5-methyl-2,4-dihydro-pyrazol-3-one
32. 2-(2-chloro-phenyl)-4-(4-dimethylamino-benzylidene)-5-methyl-2,4-dihydro-pyrazol-3-one
33. 5-methyl-4-(3-phenyl-allylidene-2-(3-trifluoromethyl-phenyl)-2,4-dihydro-pyrazol-3-one
34. 3-{5-[3-methyl-5-oxo-1-(4-sulfamoyl-phenyl)-1,5-dihydro-pyrazol-4-ylidenemethyl]-furan-2-yl}-benzoic acid
35. 4-(4-dimethylamino-benzylidene)-2-(3-fluoro-phenyl)-5-methyl-2,4-dihydro-pyrazol-3-one
36. 3-{4-[4-(3-chloro-4,5-dihydro-pyrazol-1-yl)-benzylidene]-3-methyl-5-oxo-4,5-dihydro-pyrazol-1-yl}-benzoic acid
37. 3-[4-(2-hydroxy-benzyliden)-5-oxo-3-phenyl-4,5-dihydro-pyrazol-1-yl]-benzoic acid
38. 3-[1-(3-chloro-phenyl)-3-methyl-5-oxo-1,5-dihydro-pyrazol-4-ylidenemethyl]-1H-quinolin-2-one
39. 3-{5-[3-methyl-5-oxo-1-(4-sulfamoyl-phenyl)-1,5-dihydro-pyrazol-4-ylidenemethyl]-furan-2-yl}-benzoic acid methyl ester
40. 4-(4-benzo[1,3]dioxol-5-ylmethylene-3-methyl-5-oxo-4,5-dihydro-pyrazol-1-yl)-benzoic acid methyl ester
41. 4-{3-methyl-5-oxo-4-[5-(4-sulfamoyl-phenyl)-furan-2-ylmethylene]-4,5-dihydro-pyrazol-1-yl}-benzoic acid methyl ester
42. 2-(4-chloro-phenyl)-4-(2,4-dihydroxy-benzylidene)-5-methyl-2,4-dihydro-pyrazol-3-one
43. 2-(4-chloro-phenyl)-4-(3-hydroxy-benzylidene)-5-methyl-2,4-dihydropyrazol-3-one
44. 4-(3,4-dihydroxy-benzylidene)-5-methyl-2-p-toluoyl-2,4-dihydro-pyrazol-3-one
45. 3-[1-(4-acetyl-phenyl)-3-methyl-5-oxo-1,5-dihydro-pyrazol-4-ylidene]-1,3-dihydro-indol-2-one
46. 2-(4-fluoro-phenyl)-4-(5-hydroxy-3-methyl-1-O—toluoyl-1H-pyrazol-4-ylmethylene)-5-methyl-2,4-dihydro-pyrazol-3-one
47. 2-(4-chloro-phenyl)-4-(4-hydroxy-3-methoxy-benzylidene)-5-trifluoromethyl-2,4-dihydro-pyrazol-3-one
48. 2-(4-ethyl-phenyl)-4-(4-hydroxy-benzylidene)-5-methyl-2,4-dihydro-pyrazol-3-one
49. 4-[4-(4-hydroxy-benzylidene)-3-methyl-5-oxo-4,5-dihydro-pyrazol-1-yl]-benzenesulfonamide
50. 4-(5-oxo-4-thiophen-2-ylmethylene-3-trifluoromethyl-4,5-dihydro-pyrazol-1-yl)-benzoic acid ethyl ester
51. 4-[4-(4-dimethylamino-benzyliden)-5-oxo-3-trifluoromethyl-4,5-dihydro-pyrazol-1-yl]-benzenesulfonamide
52. 4-isopropylidene-5-methyl-2-phenyl-2,4-dihydro-pyrazol-3-one
53. 4-(4-hydroxy-benzylidene)-2-phenyl-5-trifluoromethyl-2,4-dihydro-pyrazol-3-one
54. 4-(2,4-dihydroxy-benzylidene)-2-(3,4-dimethyl-phenyl)-5-methyl-2,4-dihydro-pyrazol-3-one
55. 3-[4-(3-ethoxy-4-hydroxy-benzylidene)-3-methyl-5-oxo-4,5-dihydro-pyrazol-1-yl]-benzoic acid
56. 4-[4-(3,5-di-tert-butyl-4-hydroxy-benzylidene)-3-methyl-5-oxo-4,5-dihydro-pyrazol-1-yl]-benzoic acid
57. 3-[3-(4-hydroxy-3-methoxy-benzylidene)-3-methyl-5-oxo-4,5-dihydro-pyrazol-1-yl]-benzoic acid
58. 3-[3-hydroxy-4-(4-hydroxy-3-methoxy-benzyliden)-5-oxo-pyrazolidin-1-yl]-benzoic acid
59. 4-(3-hydroxy-2,4-dimethoxy-benzylidene)-5-methyl-2-phenyl-2,4-dihydro-pyrazol-3-one
60. 4-[4-(4-hydroxy-3-methoxy-benzylidene)-3-methyl-5-oxo-pyrazolidin-1-yl]-benzoic acid isopropyl ester
61. 2-chloro-5-[4-(2-chloro-4-hydroxy-5-methoxy-benzylidene)-3-methyl-5-oxo-4,5-dihydro-pyrazol-1-yl]-benzoic acid
62. 4-[4-(4-hydroxy-benzylidene)-3-methyl-5-oxo-4,5-dihydro-pyrazol-1-yl]-benzoic acid ethyl ester
63. 4-[4-(4-hydroxy-benzylidene)-5-oxo-3-trifluoromethyl-4,5-dihydro-pyrazol-1-yl]-benzoic acid ethyl ester
64. 4-[4-(4-hydroxy-benzylidene)-3-methyl-5-oxo-4,5-dihydro-pyrazol-1-yl]-benzoic acid
65. 4-dimethylaminomethylene-5-methyl-2-phenyl-2,4-dihydro-pyrazol-3-one
66. 4-(5-hydroxy-3-methyl-1-phenyl-1H-pyrazol-4-ylmethylene)-5-methyl-2-phenyl-2,4-dihydro-pyrazol-3-one
67. 4-(4-chloro-benzylidene)-5-methyl-2-phenyl-2,4-dihydro-pyrazol-3-one
68. 1-(5-hydroxy-3-methyl-1-phenyl-1H-pyrazol-4-yl)-6-methyl-1,3-dihydro-furo[3,4-c]pyridin-7-ol
69. 1-(5-hydroxy-3-methyl-1-phenyl-1H-pyrazol-4-yl)-6-methyl-1,3-dihydro-furo [3,4-c]pyridin-7-ol; hydrochloric acid salt
70. 4-(4-hydroxy-benzylidene)-5-methyl-2-phenyl-2,4-dihydro-pyrazol-3-one
71. 2-(3-chloro-phenyl)-4-(4-hydroxy-benzylidene)-5-methyl-2,4-dihydropyrazol-3-one
72. 4-(4-benzyloxy-benzylidene)-5-methyl-2-phenyl-2,4-dihydropyrazol-3-one
73. 2-(3-chloro-phenyl)-5-methyl-2H-pyrazole-3,4-dione-4-oxime
74. 5-(5-oxo-1,3-diphenyl-1,5-dihydro-pyrazol-4-ylidene)-4-phenyl-4,5-dihydro-[1,3,4]thiazole-2-carboxylic acid ethyl ester
75. 4-[1,3]dithiolan-2-ylidene-5-methyl-2-phenyl-2,4-dihydro-pyrazol-3-one
76. 5-(4-chloro-phenylsulfanylmethyl)-2-phenyl-4-[N'-(3-trifluoromethyl-phenyl)-hydrazino]-2,4-dihydro-pyrazol-3-one
77. 4-(5-benzoyl-3-phenyl-3H-[1,3,4]thiadiazol-2-ylidene)-2,5-diphenyl-2,4-dihydro-pyrazol-3-one
78. phosphoric acid mono-[5-hydroxy-6-methyl-4-(3-methyl-5-oxo-1-phenyl-1,5-dihydro-pyrazol-4-ylidenemethyl)-pyridin-3-ylmethyl]ester
79. 3-methyl-1-phenyl-2-pyrazolin-5-one.

The above-mentioned compounds (1) and (2) may be in free form or salt form. Examples of compounds (1) and (2) in salt form include pharmaceutically acceptable salts, for example, salts with inorganic or organic bases, acid addition salts such as inorganic acid or organic acid salts, and basic or acidic aminoic acid addition salts. Examples of the salts with an inorganic base include alkali metal (such as sodium and potassium) salts, alkali earth metal (such as calcium and magnesium) salts, aluminum salts and ammonium salts. Examples of the salts with an organic base include salts with primary amines (such as ethanol amine), secondary amines (such as diethyl amine, diethanol amine, dicyclohexyl amine, and N,N'-dibenzylethylenediamine), and tertiary amines (such as trimethylamine, triethylamine, biridine, picoline, and triethanol amine). Examples of the salts with inorganic acid include salts with hydrochloric acid, hydrobromic acid, nitric acid, sulfuric acid and phosphoric acid. Examples of the salts with organic acid include salts with formic acid, acetic acid, lactic acid, trifluoro acetic acid, fumaric acid, oxalic acid, tartaric acid, maleic acid, benzoic acid, citric acid, succinic acid, malic acid, methanesulfonic acid, ethanesulfonic acid, benzenesulfonic acid and p-toluenesulfonic acid. In addition, the salts with basic aminoic acid include salts with arginine, lysine and ornithine. Examples of the salts with acidic aminoic acid include salts with aspargine acid and glutamic acid.

These compounds (1) and (2), pharmaceutically acceptable salts thereof, and pharmaceutically acceptable esters thereof can be manufactured by a known method, for example, that disclosed in WO2005/054205, using known compounds as starting materials. The method for obtaining these compounds may be usable as the method in the invention.

(2-2) Phenylene Derivative (I)

The phenylene derivative of the present invention is a compound represented by Formula (1):

[Chem. 12]

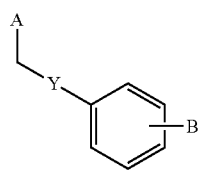

(I)

wherein A is a group represented by Formula (A1), (A2), or (A3):

[Chem. 13]

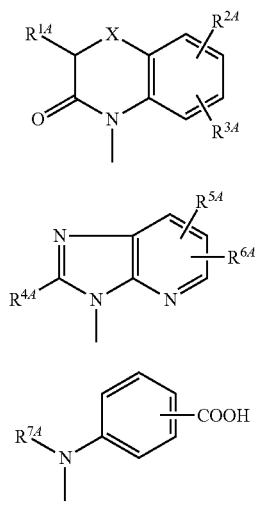

(A1)

(A2)

(A3)

B is 1H-tetrazol-5-yl or 2,4-dioxothiazolidin-5-yl; X is methylene, an oxygen atom, or a sulfur atom; Y is a single bond, or a $C_{6-10}$ arylene group; $R^{1A}$ is a hydrogen atom or a $C_{1-6}$ alkyl group; $R^{2A}$ and $R^{3A}$ are the same or different and each represent a hydrogen atom, a carboxyl group, or a $C_{1-6}$ alkyl group; $R^{4A}$, $R^{5A}$, and $R^{6A}$ are the same or different and each represent a hydrogen atom or a $C_{1-6}$ alkyl group; and $R^{7A}$ is a $C_{1-10}$ alkylcarbonyl group; provided that when A is (A2), B is a 2,4-dioxothiazolidin-5-yl group.

The "$C_{1-6}$ alkyl group" used herein represents a straight- or branched-chain alkyl group having 1 to 6 carbon atoms. Examples thereof include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, and 1,2,2-trimethylpropyl. $R^{1A}$ is preferably a propyl group. $R^{2A}$ and $R^{3A}$ are each preferably a $C_{1-3}$ alkyl group. $R^{4A}$ is preferably a $C_{1-3}$ alkyl group, and more preferably an ethyl group or a propyl group. $R^{5A}$ and $R^{6A}$ are each preferably a $C_{1-3}$ alkyl group, and more preferably a methyl group.

The "$C_{6-10}$ arylene group" represents a divalent aromatic hydrocarbon group having 6 to 10 carbon atoms. Examples thereof include phenylene, indenylene, and naphthylene. Y is preferably a phenylene group.

The "$C_{1-10}$ alkylcarbonyl group" represents a group in which a straight- or branched-chain alkyl group having 1 to 10 carbon atoms is bonded to a carbonyl group. Examples thereof include alkylcarbonyl groups, such as acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, and undecanoyl. $R^{7A}$ is preferably a $C_{4-7}$ alkylcarbonyl group, and more preferably an octanoyl group.

In the present invention, A is preferably a group represented by Formula (A1) or (A3), and more preferably a group represented by Formula (A3).

In the present invention, B is preferably a 1H-tetrazol-5-yl group.

In the present invention, X is preferably methylene or an oxygen atom, and more preferably methylene.

In the present invention, Y is preferably a single bond or phenylene, and more preferably phenylene.

In the present invention, $R^{1A}$ is preferably a propyl group or a hydrogen atom, and more preferably a propyl group.

In the present invention, $R^{2A}$ and $R^{3A}$ are the same or different, and each preferably represent a hydrogen atom, a carboxyl group, or a pharmaceutically acceptable ester thereof.

In the present invention, $R^{4A}$ is preferably an ethyl group or a propyl group.

In the present invention, $R^{4A}$ and $R^{6A}$ are each preferably a methyl group or a hydrogen atom.

In the present invention, $R^{7A}$ is preferably a $C_{4-7}$ alkylcarbonyl group, and more preferably an octanoyl group.

The phenylene derivative (I) of the present invention may be, when containing a basic group, formed into acid addition salts in accordance with a known method. Examples of such salts include salts of hydrohalogenic acids, such as hydrofluoric acid, hydrochloric acid, hydrobromic acid, and hydroiodic acid; inorganic acid salts, such as nitrate, perchlorate, sulfate, and phosphate; salts of lower alkane sulfonic acids, such as methanesulfonic acid, trifluoromethanesulfonic acid, and ethanesulfonic acid; salts of aryl sulfonic acids, such as benzenesulfonic acid and p-toluenesulfonic acid; salts of amino acids, such as glutamic acid and aspartic acid; and salts of carboxylic acids, such as acetic acid, fumaric acid, tartaric acid, oxalic acid, maleic acid, malic acid, succinic acid, benzoic acid, mandelic acid, ascorbic acid, lactic acid, gluconic acid, and citric acid. Of these, salts of hydrohalogenic acids are preferable.

Further, the phenylene derivative (I) may be, when having a carboxyl group, converted into metal salts in accordance with a known method. Examples of such salts include alkali metal salts, such as lithium, sodium, and potassium; alkaline earth metal salts, such as calcium, barium, and magnesium; and aluminum salts. Of these, alkali metal salts are preferable.

The phenylene derivative (I) of the present invention may be converted into pharmaceutically acceptable esters in accordance with a known method. There is no particular limitation to the esters, so long as the esters are medically used, and pharmaceutically accepted.

Examples of ester residues of the esters of the phenylene derivative (I) of the present invention include $C_{1-6}$ straight- or branched-chain alkyl groups (optionally substituted with a trialkylsilyl group); $C_{7-19}$ aralkyl groups; $C_{1-5}$ straight- or branched-chain alkyl group substituted with $C_{1-6}$ straight- or branched-chain alkanoyloxy; $C_{1-5}$ straight- or branched-chain alkyl groups substituted with $C_{1-6}$ straight- or branched-chain alkyloxycarbonyloxy; $C_{1-5}$ straight- or branched-chain alkyl groups substituted with $C_{5-7}$ cycloalkylcarbonyloxy; $C_{1-5}$ straight- or branched-chain alkyl groups substituted with $C_{5-7}$ cycloalkyloxycarbonyloxy; $C_{1-5}$ straight- or branched-chain alkyl groups substituted with $C_{6-10}$ arylcarbonyloxy; $C_{1-5}$ straight- or branched-chain alkyl group substituted with $C_{6-10}$ aryloxycarbonyloxy; and (2-oxo-1,3-dioxolen-4-yl)methyl groups having, as a substituent, $C_{1-6}$ straight- or branched-chain alkyl at the 5-position.

Examples of $C_{1-6}$ straight- or branched-chain alkyl groups include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, and 1,2,2-trimethylpropyl. Among these, $C_{1-4}$ straight- or branched-chain alkyl groups are preferable, methyl, ethyl, propyl, isopropyl, butyl and isobutyl are more preferable, and methyl and ethyl are most preferable.

Examples of $C_{7-19}$ aralkyl groups include benzyl, phenethyl, 3-phenylpropyl, 4-phenylbutyl, 1-naphthylmethyl, 2-naphthylmethyl, and diphenylmethyl. Among these, benzyl is preferred.

Examples of $C_{5-7}$ cycloalkyl groups include cyclopentyl, cyclohexyl, and cycloheptyl. Among these, cyclohexyl is preferred.

Examples of $C_{6-10}$ aryl groups include phenyl and naphthyl. Among these, phenyl is preferred.

Specific preferable examples of ester residues include methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopenthyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl, (5-methyl-2-oxo-1,3-dioxolen-4-yl)methyl, 2-trimethylsilylethyl, and phthalidyl; and more preferable examples thereof include (5-methyl-2-oxo-1,3-dioxolen-4-yl)methyl, pivaloyloxymethyl, and 1-(isopropoxycarbonyloxy)ethyl.

The phenylene derivative represented by Formula (1), salts thereof or esters thereof may form solvates (e.g., hydrates); the present invention encompasses such solvates.

The present invention further encompasses compounds that can be metabolized in vivo and converted into the phenylene derivative (I), salts thereof or esters thereof (i.e., prodrugs, such as amide derivatives).

Specific examples of the phenylene derivatives of the present invention represented by Formula (1), and pharmaceutically acceptable salts or esters thereof include the compounds shown in the tables below. However, the present invention is not limited to the compounds exemplified therein.

In Tables 1 to 3, "Me" represents a methyl group, "Et" represents an ethyl group, "Pr" represents a propyl group, "Bu" represents a butyl group, "t-Bu" represents a t-butyl group, "Hex" represents a hexyl group, "-Ph-" represents a phenylene group, "DMDO" represents a (5-methyl-2-oxo-1,3-dioxolen-4-yl)methyl group, "PHT" represents a phthalidyl group, "Tez" represents a 1H-tetrazolyl-5-yl group, "Tzd" represents a 2,4-dioxothiazolidin-5-yl group, and "-" represents a single bond.

TABLE 1

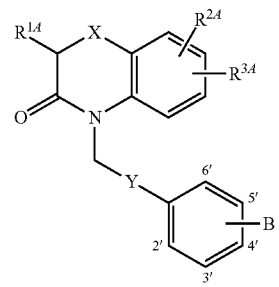

| No. | B | X | Y | $R^{1A}$ | $R^{2A}$ | $R^{3A}$ |
|---|---|---|---|---|---|---|
| 1-1 | 2'-Tez | CH$_2$ | —Ph— | Pr | H | 7-COOH |
| 1-2 | 2'-Tez | CH$_2$ | —Ph— | Pr | H | 7-COO—Me |
| 1-3 | 2'-Tez | CH$_2$ | —Ph— | Pr | H | 7-COO—Et |
| 1-4 | 2'-Tez | CH$_2$ | —Ph— | Pr | H | 7-COO—Pr |
| 1-5 | 2'-Tez | CH$_2$ | —Ph— | Pr | H | 7-COO—Bu |
| 1-6 | 2'-Tez | CH$_2$ | —Ph— | Pr | H | 7-COO—t-Bu |
| 1-7 | 2'-Tez | CH$_2$ | —Ph— | Pr | H | 7-COO—Hex |
| 1-8 | 2'-Tez | CH$_2$ | —Ph— | Pr | H | 7-COO—DMDO |
| 1-9 | 2'-Tez | CH$_2$ | —Ph— | Pr | H | 7-COO—PHT |
| 1-10 | 2'-Tez | CH$_2$ | —Ph— | Pr | H | 6-COOH |
| 1-11 | 4'-Tez | CH$_2$ | — | Pr | H | 7-COOH |
| 1-12 | 2'-Tez | CH$_2$ | —Ph— | H | H | 7-COOH |
| 1-13 | 2'-Tez | CH$_2$ | —Ph— | Me | H | 7-COOH |
| 1-14 | 2'-Tez | CH$_2$ | —Ph— | Et | H | 7-COOH |
| 1-15 | 2'-Tez | CH$_2$ | —Ph— | Bu | H | 7-COOH |
| 1-16 | 2'-Tez | CH$_2$ | —Ph— | Pen | H | 7-COOH |
| 1-17 | 2'-Tez | CH$_2$ | —Ph— | Hex | H | 7-COOH |
| 1-18 | 2'-Tez | CH$_2$ | —Ph— | Pr | 6-Me | 7-COOH |
| 1-19 | 4'-Tez | O | — | Pr | H | 6-COOH |
| 1-20 | 2'-Tez | O | —Ph— | Pr | H | 6-COOH |
| 1-21 | 2'-Tez | O | —Ph— | Pr | H | 6-COO—Me |
| 1-22 | 2'-Tez | O | —Ph— | Pr | H | 6-COO—DMDO |
| 1-23 | 4'-Tez | O | — | Pr | H | 6-COOH |

TABLE 1-continued

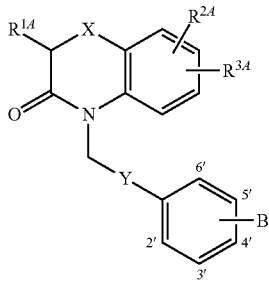

| No. | B | X | Y | $R^{1A}$ | $R^{2A}$ | $R^{3A}$ |
|---|---|---|---|---|---|---|
| 1-24 | 2'-Tez | O | —Ph— | Bu | H | 6-COOH |
| 1-25 | 2'-Tez | S | —Ph— | Pr | H | 6-COOH |
| 1-26 | 2'-Tez | S | —Ph— | Pr | H | 6-COO—Me |
| 1-27 | 2'-Tez | S | —Ph— | Pr | H | 6-COO-DMDO |
| 1-28 | 2'-Tzd | $CH_2$ | —Ph— | Pr | H | 7-COOH |
| 1-29 | 2'-Tez | $CH_2$ | —Ph— | H | H | H |
| 1-30 | 4'-Tez | S | —Ph— | Pr | H | 6-COOH |
| 1-31 | 4'-Tzd | $CH_2$ | —Ph— | Pr | H | 7-COOH |
| 1-32 | 4'-Tzd | $CH_2$ | —Ph— | Pr | H | 7-COO—Et |

TABLE 2

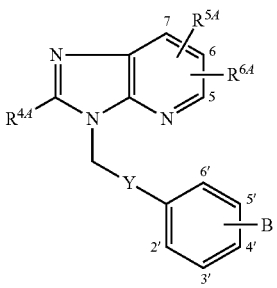

| No. | B | Y | $R^{4A}$ | $R^{5A}$ | $R^{6A}$ |
|---|---|---|---|---|---|
| 2-1 | 4'-Tzd | — | Me | 7-Me | 5-Me |
| 2-2 | 4'-Tzd | — | Et | 7-Me | 5-Me |
| 2-3 | 2'-Tzd | —Ph— | Et | 7-Me | 5-Me |
| 2-4 | 4'-Tzd | — | Et | H | 5-Me |
| 2-5 | 4'-Tzd | — | Et | 7-Me | H |
| 2-6 | 4'-Tzd | — | Et | H | H |
| 2-7 | 4'-Tzd | — | Et | 7-Me | 5-Et |
| 2-8 | 4'-Tzd | — | Et | 7-Me | 6-Me |
| 2-9 | 4'-Tzd | — | Et | 7-Me | 5-Pr |
| 2-10 | 4'-Tzd | — | Et | 7-Me | 5-Bu |
| 2-11 | 4'-Tzd | — | Et | 7-Me | 5-Hex |
| 2-12 | 4'-Tzd | — | Pr | 7-Me | 5-Me |
| 2-13 | 2'-Tzd | —Ph— | Pr | 7-Me | 5-Me |
| 2-14 | 4'-Tzd | — | Pr | H | 5-Me |
| 2-15 | 4'-Tzd | — | Bu | 7-Me | 5-Me |
| 2-16 | 4'-Tzd | — | Pn | 7-Me | 5-Me |
| 2-17 | 4'-Tzd | — | Hex | 7-Me | 5-Me |
| 2-18 | 4'-Tzd | — | Et | 7-Me | 5-Me |

TABLE 3

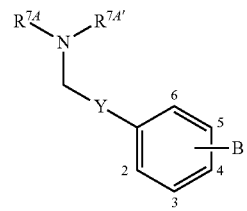

| No. | B | Y | $R^{7A}$ | $R^{7A'}$ |
|---|---|---|---|---|
| 3-1 | 4-Tez | — | $CH_3$—$(CH_2)_3$—CO— | (3-COOH)—Ph |
| 3-2 | 4-Tez | — | $CH_3$—$(CH_2)_3$—CO— | (3-COO—DMDO)—Ph |
| 3-3 | 2-Tez | —Ph— | $CH_3$—$(CH_2)_6$—CO— | (3-COOH)—Ph |
| 3-4 | 2-Tez | —Ph— | $CH_3$—CO— | (3-COOH)—Ph |
| 3-5 | 2-Tez | —Ph— | $CH_3$—$CH_2$—CO— | (3-COOH)—Ph |
| 3-6 | 2-Tez | —Ph— | $CH_3$—$(CH_2)_2$—CO— | (3-COOH)—Ph |
| 3-7 | 2-Tez | —Ph— | $CH_3$—$(CH_2)_3$—CO— | (3-COOH)—Ph |
| 3-8 | 2-Tez | —Ph— | $CH_3$—$(CH_2)_3$—CO— | (2-COOH)—Ph |
| 3-9 | 2-Tez | —Ph— | $CH_3$—$(CH_2)_3$—CO— | (3-COOH)—Ph |
| 3-10 | 2-Tez | —Ph— | $CH_3$—$(CH_2)_3$—CO— | (4-COOH)—Ph |
| 3-11 | 2-Tez | —Ph— | $CH_3$—$(CH_2)_4$—CO— | (3-COOH)—Ph |
| 3-12 | 2-Tez | —Ph— | $CH_3$—$(CH_2)_5$—CO— | (3-COOH)—Ph |
| 3-13 | 2-Tez | —Ph— | $CH_3$—$(CH_2)_6$—CO— | (3-COOH)—Ph |
| 3-14 | 2-Tez | —Ph— | $CH_3$—$(CH_2)_8$—CO— | (3-COOH)—Ph |
| 3-15 | 2-Tez | —Ph— | $CH_3$—$(CH_2)_9$—CO— | (3-COOH)—Ph |
| 3-16 | 2-Tzd | —Ph— | $CH_3$—$(CH_2)_6$—CO— | (3-COOH)—Ph |
| 3-17 | 2-Tez | —Ph— | $CH_3$—$(CH_2)_6$—CO— | (2-COOH)—Ph |
| 3-18 | 4-Tez | —Ph— | $CH_3$—$(CH_2)_6$—CO— | (3-COOH)—Ph |
| 3-19 | 2-Tez | —Ph— | $CH_3$—$(CH_2)_6$—CO— | (4-COOH)—Ph |
| 3-20 | 2-Tez | —Ph— | $CH_3$—$(CH_2)_3$—CO— | (3-COO—Me)—Ph |
| 3-21 | 2-Tez | —Ph— | $CH_3$—$(CH_2)_3$—CO— | (3-COO—Et)—Ph |
| 3-22 | 2-Tez | —Ph— | $CH_3$—$(CH_2)_3$—CO— | (3-COO—Pr)—Ph |
| 3-23 | 2-Tez | —Ph— | $CH_3$—$(CH_2)_3$—CO— | (3-COO—Bu)—Ph |
| 3-24 | 2-Tez | —Ph— | $CH_3$—$(CH_2)_3$—CO— | (3-COO—Hex)—Ph |
| 3-25 | 2-Tez | —Ph— | $CH_3$—$(CH_2)_3$—CO— | (3-COO—DMDO)—Ph |
| 3-26 | 2-Tez | —Ph— | $CH_3$—$(CH_2)_8$—CO— | (3-COO—DMDO)—Ph |
| 3-27 | 2-Tzd | —Ph— | $CH_3$—$(CH_2)_3$—CO— | (3-COO—DMDO)—Ph |
| 3-28 | 2-Tez | —Ph— | $CH_3$—$(CH_2)_3$—CO— | (3-COO—PHT)—Ph |
| 3-29 | 2-Tez | —Ph— | $CH_3$—$(CH_2)_7$—CO— | (3-COOH)—Ph |
| 3-30 | 4-Tzd | — | $CH_3$—$(CH_2)_3$—CO— | (3-COOH)—Ph |
| 3-31 | 4-Tzd | — | $CH_3$—$(CH_2)_3$—CO— | (3-COO—Et)—Ph |
| 3-32 | 4-Tzd | — | $CH_3$—$(CH_2)_3$—CO— | (3-COO—DMDO)—Ph |

Among the compounds shown in the above tables, the compounds of Nos. 1-1, 1-8, 1-10, 1-19, 1-20, 1-25, 1-29, 1-30, 2-2, 2-3, 2-12, 2-18, 3-3, 3-4, 3-5, 3-6, 3-7, 3-8, 3-9, 3-10, 3-13, 3-25, 3-29, and 3-30 are preferable, and the compounds of Nos. 1-1, 2-2, 3-7, 3-6, 3-3, 3-9, 3-13, 3-25, and 3-30 are more preferable.

The phenylene derivative (I), pharmaceutically acceptable salts thereof and pharmaceutically acceptable esters thereof may be prepared in accordance with a method disclosed in, for example, WO2005/030737, using a known compound as a starting material. The production method of the phenylene derivative (I) disclosed in the above publication is incorporated herein by reference.

(2-3) Phenylene Derivative (II)

The phenylene derivative of the present invention is a compound represented by Formula (II):

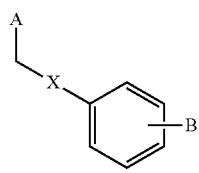

(II)

wherein A is a group represented by Formula (A4), (A5), (A6), or (A7):

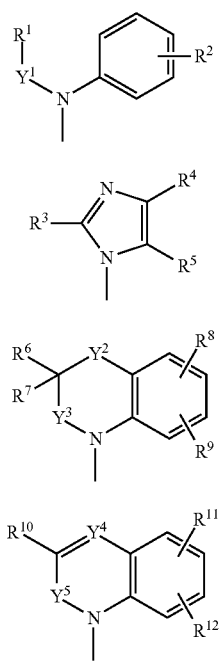

B is 1H-tetrazol-5-yl or 2,4-dioxo-1,3-thiazolidin-5-yl; X is a single bond or a $C_{6-10}$ arylene group; $Y^1$ is carbonyl, sulfonyl, or a single bond; $Y^2$ is a $C_{1-6}$ alkylene group or a single bond; $Y^3$ is methylene, carbonyl, or a single bond; $Y^4$ is methine or a nitrogen atom; $Y^5$ is methylene, carbonyl, or a single bond; $R^1$ is a $C_{1-8}$ alkyl group (optionally substituted with 1 to 3 substituents selected from the group α of substituents shown below), a $C_{6-14}$ aryl group (optionally substituted with 1 to 5 substituents selected from the group β of substituents shown below), a $C_{6-14}$ aryl-$C_{1-6}$ alkyl group (optionally substituted with 1 to 5 substituents selected from the group β of substituents shown below), a 4- to 10-membered heterocyclic group containing 1 to 3 identical or different heteroatoms selected from the group consisting of nitrogen, oxygen, and sulfur (the heterocyclic group is optionally substituted with 1 to 5 substituents selected from the group β of substituents shown below), a 4- to 10-membered heterocyclic-$C_{1-6}$ alkyl group containing 1 to 3 identical or different heteroatoms selected from the group consisting of nitrogen, oxygen, and sulfur (the heterocyclic group is optionally substituted with 1 to 5 substituents selected from the group β of substituents shown below), a $C_{3-7}$ cycloalkyl group (optionally substituted with 1 to 5 substituents selected from the group β of substituents shown below), a $C_{3-7}$ cycloalkyl-$C_{1-6}$ alkyl group (optionally substituted with 1 to 5 substituents selected from the group β of substituents shown below), a $C_{6-14}$ aryl-carbonyl-$C_{1-6}$ alkyl group (optionally substituted with 1 to 5 substituents selected from the group β of substituents shown below), or a $C_{1-6}$ aliphatic acyl group (optionally substituted with 1 to 5 substituents selected from the group β of substituents shown below); $R^2$ is a hydrogen atom, a group selected from the group β of substituents shown below, a carboxyl group, or a group represented by —C(O)NR$^{13}$R$^{14}$; $R^3$ is a hydrogen atom, a 8 alkyl group (optionally substituted with 1 to 3 substituents selected from the group α of substituents shown below), a $C_{6-14}$ aryl group (optionally substituted with 1 to 5 substituents selected from the group β of substituents shown below), or a O-5 to 10-membered heterocyclic group containing 1 to 3 identical or different heteroatoms selected from the group consisting of nitrogen, oxygen, and sulfur (the heterocyclic group is optionally substituted with 1 to 5 substituents selected from the group β of substituents shown below); $R^4$ and $R^5$ are the same or different and each represent a hydrogen atom or a $C_{6-14}$ aryl group (optionally substituted with 1 to 5 substituents selected from the group β of substituents shown below); $R^6$ and $R^7$ join to form $C_{3-7}$ cycloalkane, or are the same or different and each represent a hydrogen atom or a $C_{1-8}$ alkyl group (optionally substituted with 1 to 3 substituents selected from the group α of substituents); $R^8$ and $R^9$ are the same or different and each represent a hydrogen atom, a group selected from the group β of substituents shown below, carboxyl group, or a group represented by —C(O)NR$^{13}$R$^{14}$; $R^{10}$ is a hydrogen atom, a $C_{1-8}$ alkyl group (optionally substituted with 1 to 3 substituents selected from the group α of substituents shown below), a $C_{6-14}$ aryl group (optionally substituted with 1 to 5 substituents selected from the group β of substituents shown below), or a 4- to 10-membered heterocyclic group containing 1 to 3 identical or different heteroatoms selected from the group consisting of nitrogen, oxygen, and sulfur (the heterocyclic group is optionally substituted with 1 to 5 substituents selected from the group β of substituents shown below); $R^{11}$ and $R^{12}$ are the same or different and each represent a hydrogen atom, a group selected from the group β of substituents shown below, a carboxyl group, or a group represented by —C(O)NR$^{13}$R$^{14}$; $R^{13}$ and $R^{14}$ join to form a 4- to 10-membered nitrogen-containing heterocyclic ring (optionally substituted with 1 to 5 substituents selected from the group β of substituents shown below), or are the same or different and each represent a hydrogen atom or $C_{1-8}$ alkyl group (optionally substituted with 1 to 3 substituents selected from the group α of substituents shown below), provided that: (1) when $R^1$ is a $C_{1-8}$ alkyl group and $Y^2$ is a single bond, B is 2,4-dioxo-1,3-thiazolidin-5-yl; (2) when $Y^2$ is methylene, neither $R^6$ nor $R^7$ is a hydrogen atom; (3) when $R^1$ is an unsubstituted $C_{1-8}$ alkyl group, $Y^1$ is not carbonyl; and (4) when $R^1$ is an unsubstituted $C_{1-6}$ aliphatic acyl group, $Y^2$ is not a single bond.

Here, the group α of substituents consists of halogen atoms, $C_{1-6}$ alkylthio groups, $C_{1-6}$ aliphatic acyl groups, $C_{1-6}$ alkylsulfonyl groups, $C_{1-6}$ alkoxy groups, a cyano group, and a nitro group; and the group β of substituents consists of halogen atoms, $C_{1-6}$ alkyl groups, halo-$C_{1-6}$ alkyl groups, $C_{1-6}$ alkoxy groups, $C_{1-6}$ alkylthio groups, $C_{1-6}$ alkylsulfonyl groups, $C_{1-6}$ aliphatic acyl groups, an oxo group, a cyano group, a nitro group, $C_{3-7}$ cycloalkyl groups, $C_{6-14}$ aryl groups, $C_{1-6}$ alkoxyimino, $C_{6-14}$ aryl-carbonyl groups, and 4- to 10-membered heterocyclic groups containing 1 to 3 identical or different heteroatoms selected from the group consisting of nitrogen, oxygen, and sulfur.

In the phenylene derivative represented by Formula (II), the "$C_{6-10}$ arylene group" represents a divalent aromatic hydrocarbon group having 6 to 10 carbon atoms. Examples thereof include 1,2-phenylene, 1,3-phenylene, 1,4-phenylene, 1,2-naphthylene, 1,3-naphthylene, 1,4-naphthylene, 1,5-naphthylene, 1,6-naphthylene, 1,7-naphthylene, 1,8-naphthylene, 2,3-naphthylene, 2,4-naphthylene, and the like.

X is preferably phenylene.

In the phenylene derivative (II), the "$C_{1-6}$ alkylene group" represents a straight- or branched-chain alkylene group having 1 to 6 carbon atoms. Examples thereof include methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, hexamethylene, and the like.

$Y^2$ is preferably a $C_{1-3}$ alkylene group, and more preferably methylene or ethylene.

In the phenylene derivative (II), the "$C_{1-8}$ alkyl groups" represents a straight- or branched-chain alkyl group having 1 to 8 carbon atoms. Examples thereof include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, heptyl, 1-methylpentyl, 2-methylpentyl, n-heptyl, isoheptyl, sec-heptyl, tert-heptyl, n-octyl, isooctyl, tert-octyl, 2-methylhexyl, 2-ethylhexyl, and the like.

(1) When $Y^1$ is a sulfonyl group, $R^1$ is preferably a $C_{1-6}$ alkyl group, more preferably methyl, ethyl, propyl, butyl, pentyl or hexyl, and still more preferably methyl or butyl; and (2) when $Y^1$ is a single bond or a carbonyl group, $R^1$ is preferably a $C_{4-8}$ alkyl group, more preferably butyl, pentyl, hexyl, heptyl or octyl, and still more preferably pentyl.

$R^3$ is preferably a $C_{1-5}$ alkyl group, and more preferably methyl, ethyl, propyl, butyl or pentyl.

$R^6$ and $R^7$ are each preferably a $C_{1-3}$ alkyl group or methyl, and more preferably ethyl or propyl.

$R^{10}$ is preferably a $C_{1-4}$ alkyl group, and more preferably methyl, ethyl, propyl or butyl.

$R^{13}$ and $R^{14}$ are preferably a $C_{1-3}$ alkyl group, and more preferably methyl and ethyl.

In the phenylene derivative (II), the "$C_{1-6}$ alkyl group" represents a $C_{1-6}$ straight- or branched-chain alkyl group. Examples thereof include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, and the like.

The substituent β is preferably a $C_{1-3}$ alkyl group, and more preferably methyl or ethyl.

In the phenylene derivative (II), the "$C_{6-14}$ aryl group" represents an aromatic hydrocarbon group having 6 to 14 carbon atoms. Examples thereof include phenyl, naphthyl, anthryl, phenanthryl, acenaphthylenyl, and the like.

$R^4$ is preferably a $C_{6-10}$ aryl group, and more preferably phenyl or naphthyl.

$R^3$ is preferably a $C_{6-10}$ aryl group, and more preferably phenyl or naphthyl.

$R^4$ and $R^5$ are preferably a $C_{6-10}$ aryl group, and more preferably phenyl.

$R^{10}$ is preferably a $C_{6-10}$ aryl group, and more preferably phenyl.

The substituent β is preferably a $C_{6-10}$ aryl group, and more preferably phenyl.

In the phenylene derivative (II), a "$C_{6-14}$ aryl-$C_{1-5}$-6 alkyl group" represents a group in which the above-mentioned "$C_{6-14}$ aryl group" is bonded to the above-mentioned "$C_{1-6}$ alkyl group". Examples thereof include benzyl, 1-phenethyl, 2-phenethyl, 3-phenylpropyl, 4-phenylbutyl, 5-phenylpentyl, 5-phenylhexyl, 1-naphthylmethyl, 2-naphthylethyl, anthrylmethyl, phenanthrylmethyl, acenaphthylenylmethyl, and the like.

$R^1$ is preferably a $C_{6-10}$ aryl-$C_{1-3}$ alkyl group, and more preferably benzyl, 1-phenethyl, 2-phenethyl, 3-phenylpropyl, 1-naphthylmethyl, 2-naphthylmethyl, 2-(1-naphthyl)ethyl, or 2-(2-naphthylethyl).

In the phenylene derivative (II), examples of the "4- to 10-membered heterocyclic groups containing 1 to 3 identical or different heteroatoms selected from the group consisting of nitrogen, oxygen, and sulfur" include unsaturated heterocyclic groups, such as pyrrolyl, furyl, thienyl, pyrazolyl, imidazolyl, oxazolyl, isoxazolyl, thiazolyl, isothiazolyl, oxadiazolyl, thiadiazolyl, triazolyl, tetrazolyl, pyranyl, pyridyl, pyridazinyl, pyrimidinyl, pyrazinyl, azepinyl, azocinyl, and the like; and groups in which the above unsaturated heterocyclic group is partially or completely reduced, such as azetidinyl, pyrrolidinyl, pyrrolinyl, imidazolidinyl, imidazolinyl, pyrazolidinyl, pyrazolinyl, piperidyl, piperazinyl, morpholinyl, thiomorpholinyl, perhydroazepinyl, perhydroazocinyl, 1,4,5,6-tetrahydropyrimidinyl, 1,2,3,6-tetrahydropyridyl, and the like. Examples of the groups further include groups in which the above-mentioned unsaturated heterocyclic rings are condensed with each other or groups in which a benzene ring is condensed with the above-mentioned unsaturated heterocyclic ring, such as indolyl, indolinyl, benzofuranyl, benzothienyl, benzimidazolyl, benzisooxazolyl, benzisoxazolyl, benzothiazolyl, benzisothiazolyl, quinolyl, isoquinolyl, quinazolinyl, quinoxalinyl, benzoxadiazolyl, benzothiadiazolyl, pyrrolopyrrolyl, pyrrolooxazolyl, pyrrolothiazolyl, pyrrolopyridyl, furopyrrolyl, furopyridyl, thienopyrrolyl, thienopyridyl, imidazopyrrolyl, imidazoimidazolyl, imidazooxazolyl, imidazoisoxazolyl, imidazothiazolyl, imidazoisothiazolyl, imidazopyridyl, imidazopyridazinyl, imidazopyrimidinyl, imidazopyrazinyl, oxazooxazolyl, oxazoisoxazolyl, oxazothiazolyl, oxazoisothiazolyl, oxazopyridyl, thiazooxazolyl, thiazoisoxazolyl, thiazothiazolyl, thiazoisothiazolyl, thiazopyridyl, and the like.

$R^1$ is preferably a 5- or 6-membered heterocyclic group containing 1 or 2 identical or different heteroatoms selected from the group consisting of nitrogen, oxygen, and sulfur (the heterocyclic ring is optionally condensed with a benzene ring), and more preferably pyridyl, oxazolyl, thiazolyl or quinolyl.

$R^3$ is preferably a 5- or 6-membered heterocyclic group containing 1 or 2 heteroatoms selected from the group consisting of nitrogen, oxygen, and sulfur (the heterocyclic ring is optionally condensed with a benzene ring), and more preferably pyridyl or quinolyl.

$R^{10}$ is preferably a 5- or 6-membered heterocyclic group containing 1 or 2 identical or different heteroatoms selected from the group consisting of nitrogen, oxygen, and sulfur (the heterocyclic ring is optionally condensed with a benzene ring), and more preferably pyridyl or quinolyl.

The substituent β is preferably a 5- or 6-membered heterocyclic group containing 1 or 2 identical or different heteroatoms selected from the group consisting of nitrogen, oxygen, and sulfur (the heterocyclic ring is optionally condensed with a benzene ring); and more preferably imidazolyl, thiazolyl, oxazolyl, oxadiazolyl or pyridyl. This heterocyclic group is optionally substituted with 1 to 3 of the above-mentioned "$C_{1-6}$ alkyl groups".

In the phenylene derivative (II), the "4- to 10-membered nitrogen-containing heterocyclic ring" represents, among the rings constituting the above-mentioned "4- to 10-membered heterocyclic group containing 1 to 3 identical or different heteroatoms selected from the group consisting of nitrogen, oxygen, and sulfur", a ring that contains at least one nitrogen and that may further contain 1 or 2 identical or different heteroatoms selected from the group consisting of nitrogen, oxygen, and sulfur. Examples thereof include unsaturated heterocyclic rings, such as pyrrole, pyrazole, imidazole, triazole, tetrazole and the like; and rings in which the above-mentioned unsaturated heterocyclic ring is partially or completely reduced, such as azetidine, pyrrolidine, pyrroline, imidazolidine, imidazoline, pyrazolidine, pyrazoline, piperidine, piperazine, morpholine, thiomorpholine, perhydroazepine, perhydroazocine, 1,4,5,6-tetrahydropyrimidine, 1,2,3,6-tetrahydropyridine, and the like. Examples of the rings further include rings in which the above unsaturated heterocyclic rings are condensed with each other or rings in which a benzene ring is condensed with the above-mentioned unsaturated heterocyclic ring, such as indole, indoline, benzimidazole pyrrolopyrrole, pyrrolooxazole, pyrrolothiazol, pyrrolopyridine, furopyrrole, thienopyrrole, imidazopyrrole, imidazoimidazole, imidazooxazole, imidazoisoxazole, imidazothiazol, imidazoisothiazol, imidazopyridine, imidazopyridazine, imidazopyrimidine, imidazo pyrazine, and the like.

$R^{13}$ and $R^{14}$ are each preferably an imidazole, pyrrolidine, piperidine, morpholine or indole ring, and more preferably a pyrrolidine, piperidine or morpholine ring.

In the phenylene derivative (II), the "4- to 10-membered heterocyclic-$C_{1-6}$ alkyl group containing 1 to 3 identical or different heteroatoms selected from the group consisting of nitrogen, oxygen, and sulfur" represents a group in which the above-mentioned "4- to 10-membered heterocyclic group containing 1 to 3 identical or different heteroatoms selected from the group consisting of nitrogen, oxygen, and sulfur" is bonded to the above-mentioned "$C_{1-6}$ alkyl group". Examples thereof include pyrrolylmethyl, furylmethyl, thienylmethyl, thienylethyl, thienylpropyl, pyrazolylmethyl, imidazolylmethyl, oxazolylmethyl, isoxazolylmethyl, thiazolylmethyl, isothiazolylmethyl, oxadiazolylmethyl, thiadiazolylmethyl, triazolylmethyl, tetrazolylmethyl, pyranylmethyl, pyridylmethyl, pyridazinylmethyl, pyrimidinylmethyl, pyrazinylmethyl, azepinylmethyl, azocinylmethyl, azetidinylmethyl, pyrrolidinylmethyl, pyrrolinylmethyl, imidazolidinylmethyl, imidazolinylmethyl, pyrazolidinylmethyl, pyrazolinylmethyl, piperidylmethy, piperazinylmethyl, morpholinylmethyl, thiomorpholinylmethyl, perhydroazepinylmethyl, perhydroazocinylmethyl, 1,4,5,6-tetrahydropyrimidinylmethyl, 1,2,3,6-tetrahydropyridylmethyl, indolylmethyl, indolinylmethyl, benzofuranylmethyl, benzothienylmethyl, benzimidazolylmethyl, benzisooxazolylmethyl, benzisoxazolylmethyl, benzothiazolylmethyl, benzisothiazolylmethyl, quinolylmethyl, isoquinolylmethyl, quinazolinylmethyl, quinoxalinylmethyl, benzoxadiazolylmethyl, benzothiadiazolylmethyl, pyrrolopyrrolyl methyl, pyrrolooxazolyl methyl, pyrrolothiazolyl methyl, pyrrolopyridyl methyl, furopyrrolyl methyl, furopyridyl methyl, thienopyrrolyl methyl, thienopyridyl methyl, imidazo pyrrolylmethyl, imidazo imidazolylmethyl, imidazo oxazolylmethyl, imidazo isoxazolylmethyl, imidazo thiazolylmethyl, imidazo isothiazolylmethyl, imidazo pyridylmethyl, imidazo pyridazinylmethyl, imidazo pyrimidinylmethyl, imidazo pyrazinylmethyl, oxazolo oxazolyl methyl, oxazolo isoxazolylmethyl, oxazolo thiazolylmethyl, oxazolo isothiazolylmethyl, oxazolo pyridylmethyl, thiazolo oxazolylmethyl, thiazolo isoxazolylmethyl, thiazolo thiazolylmethyl, thiazolo isothiazolylmethyl, thiazolo pyridylmethyl, and the like.

$R^1$ is preferably a 5- or 6-membered heterocyclic ring-$C_{1-3}$ alkyl group containing 1 or 2 identical or different heteroatoms selected from the group consisting of nitrogen, oxygen, and sulfur (the heterocyclic ring is optionally condensed with a benzene ring), and more preferably oxazolylmethyl, thiazolylmethyl, pyridylmethyl, quinolylmethyl, thienylethyl or thienylpropyl.

In the phenylene derivative (II), the "$C_{3-7}$ cycloalkyl group" represents a $C_{3-7}$ cyclic alkyl group, examples of which include cyclopropyl, cyclobutyl, cyclopentyl, cyclohexyl, cycloheptyl, and the like.

$R^1$ is preferably a $C_{5-6}$ cycloalkyl group, and more preferably cyclopentyl or cyclohexyl.

The substituent β is preferably a $C_{4-6}$ cycloalkyl group, and more preferably cyclopentyl or cyclohexyl.

In the phenylene derivative (II), the "$C_{3-7}$ cycloalkyl-$C_{1-6}$ alkyl group" represents a group in which the above-mentioned "$C_{3-7}$ cycloalkyl group" is bonded to the above-mentioned "$C_{1-6}$ alkyl group". Examples thereof include cyclopropylmethyl, 2-cyclopropylethyl, cyclobutylmethyl, 2-cyclobutylethyl, cyclopentylmethyl, 2-cyclopentylethyl, 3-cyclopentylpropyl, 4-cyclopentylbutyl, 5-cyclopentylpentyl, 6-cyclopentylhexyl, cyclohexylmethyl, 2-cyclohexylethyl, 3-cyclohexylpropyl, 4-cyclohexylbutyl, 5-cyclohexylpentyl, 6-cyclohexylhexyl, cycloheptylmethyl, 2-cycloheptylethyl, and the like.

$R^1$ is preferably a $C_{5-6}$ cycloalkyl-$C_{1-3}$ alkyl group, and more preferably cyclohexylmethyl or 2-cyclohexylethyl.

In the phenylene derivative (II), the "$C_{6-14}$ aryl-carbonyl-$C_{1-6}$ alkyl group" represents a group in which the above-mentioned "$C_{6-14}$ aryl group" that is bonded to a carbonyl group is further bonded to the above "$C_{1-6}$ alkyl group". Examples thereof include benzoylmethyl, 2-benzoylethyl, 3-benzoylpropyl, 4-benzoylbutyl, 5-benzoylpentyl, 6-benzoylhexyl, naphthoylmethyl, 2-naphthoyl ethyl, and the like.

$R^1$ is preferably a $C_{6-10}$ aryl-carbonyl-$C_{1-3}$ alkyl group, and more preferably benzoylmethyl or naphthoylmethyl.

In the phenylene derivative (II), the "$C_{1-6}$ aliphatic acyl group" represents a group in which a hydrogen atom, or saturated or unsaturated $C_{2-5}$ chain hydrocarbon group is bonded to a carbonyl group. Examples thereof include formyl, acetyl, propionyl, butyryl, isobutyryl, valeryl, isovaleryl, pivaloyl, hexanoyl, acryloyl, methacryloyl, crotonoyl, and the like.

$R^1$ is preferably a $C_{1-4}$ aliphatic acyl group, and more preferably butyryl.

The substituents α and β are each preferably a $C_{1-4}$ aliphatic acyl group, more preferably acetyl or propionyl, and most preferably acetyl.

In the phenylene derivative (II), the "$C_{3-7}$ cycloalkane" represents a $C_{3-7}$ cyclic alkane, examples of which include cyclopropane, cyclobutane, cyclopentane, cyclohexane, cycloheptane, and the like.

$R^6$ and $R^7$ preferably join to form a $C_{3-5}$ cycloalkane, and more preferably form a cyclopropane.

In the phenylene derivative (II), examples of the "halogen atom" include fluorine, chlorine, bromine, and iodine.

The substituents α and β are each preferably a fluorine atom, a chlorine atom or a bromine atom, more preferably a fluorine atom or a chlorine atom, and most preferably a fluorine atom.

In the phenylene derivative (II), the "$C_{2-6}$ alkoxy group" represents a hydroxyl group substituted with the above-mentioned $C_{2-6}$ alkyl group. Examples thereof include methoxy, ethoxy, 1-propoxy, 2-propoxy, 1-butoxy, 2-butoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, and the like.

The substituents α and β are each preferably a $C_{1-4}$ alkoxy group, more preferably methoxy or ethoxy, and most preferably methoxy.

In the phenylene derivative (II), the "$C_{1-6}$ alkylthio group" represents a mercapto group substituted with the above-mentioned $C_{1-6}$ alkyl group. Examples thereof include a methylthio, ethylthio, 1-propylthio, 2-propylthio, 1-butylthio, 2-butylthio, 2-methyl-1-propylthio, 2-methyl-2-propylthio, 1-pentylthio, 2-pentylthio, 3-pentylthio, 2-methyl-2-butylthio, 3-methyl-2-butylthio, 1-hexylthio, 2-hexylthio, 3-hexylthio, 2-methyl-1-pentylthio, 3-methyl-1-pentylthio, 2-ethyl-1-butylthio, 2,2-dimethyl-1-butylthio, 2,3-dimethyl-1-butylthio, and the like.

The substituents α and β are each preferably a $C_{1-4}$ alkylthio group, more preferably methylthio or ethylthio, and most preferably methylthio.

In the phenylene derivative (II), the "$C_{1-6}$ alkylsulfonyl" represents a sulfonyl group (—$SO_2$—) substituted with the above-mentioned $C_{1-6}$ alkyl group, examples of which include a methanesulfonyl, ethanesulfonyl, 1-propanesulfonyl, 2-propanesulfonyl, 1-butanesulfonyl, 2-butanesulfonyl, 2-methyl-1-propanesulfonyl, 2-methyl-2-propanesulfonyl, 1-pentanesulfonyl, 2-pentanesulfonyl, 3-pentanesulfonyl, 2-methyl-2-butanesulfonyl, 3-methyl-2-butanesulfonyl, 1-hexanesulfonyl, 2-hexanesulfonyl, 3-hexanesulfonyl, 2-methyl-1-pentanesulfonyl, 3-methyl-1-pentanesulfonyl, 2-ethyl-1-butanesulfonyl, 2,2-dimethyl-1-butanesulfonyl, 2,3-dimethyl-1-butanesulfonyl, and the like.

The substituents α and β are each preferably a $C_{1-4}$ alkylsulfonyl, more preferably methanesulfonyl or ethanesulfonyl, and most preferably methanesulfonyl.

In the phenylene derivative (II), the "halo-$C_{1-6}$ alkyl group" represents the above-mentioned $C_{1-6}$ alkyl group that is substituted with 1 to 7 of the halogen atoms mentioned above. Examples thereof include fluoromethyl, difluoromethyl, dichloromethyl, dibromomethyl, trifluoromethyl, trichloromethyl, 2-fluoroethyl, 2-bromoethyl, 2-chloroethyl, 2-iodoethyl, 2,2-difluoroethyl, 2,2,2-trifluoroethyl, 2,2,2-trichloroethyl, pentafluoroethyl, 3-fluoropropyl, 3-chloropropyl, 4-fluorobutyl, 5-fluoropentyl, 6-fluorohexyl, and the like.

The substituent β is preferably a $C_{1-4}$ alkyl group that is substituted with 1 to 5 halogen atoms, more preferably fluoromethyl, chloromethyl, difluoromethyl, trifluoromethyl or pentafluoroethyl, and most preferably trifluoromethyl.

In the phenylene derivative (II), the "$C_{6-14}$ aryl-carbonyl group" represents a group in which the above-mentioned "$C_{6-14}$ aryl group" is bonded to a carbonyl group. Examples thereof include benzoyl, naphthylcarbonyl, phenanthrylcarbonyl, and the like.

The substituent β is preferably a $C_{6-10}$ aryl-carbonyl group, and more preferably benzoyl.

In the phenylene derivative (II), the "$C_{1-6}$ alkoxyimino" represents an imino group that is substituted with the above-mentioned $C_{1-6}$ alkoxy group. Examples thereof include methoxyimino, ethoxyimino, 1-propoxyimino, 2-propoxyimino, 1-butoxyimino, 2-butoxyimino, 2-methyl-1-propoxyimino, 2-methyl-2-propoxyimino, 1-pentyloxyimino, 2-pentyloxyimino, 3-pentyloxyimino, 2-methyl-2-butoxyimino, 3-methyl-2-butoxyimino, 1-hexyloxyimino, 2-hexyloxyimino, 3-hexyloxyimino, 2-methyl-1-pentyloxyimino, 3-methyl-1-pentyloxyimino, 2-ethyl-1-butoxyimino, 2,2-dimethyl-1-butoxyimino, 2,3-dimethyl-1-butoxyimino, and the like.

The substituent β is preferably a $C_{1-4}$ alkoxyimino, more preferably methoxyimino or ethoxyimino, and most preferably methoxyimino.

In the phenylene derivative (II), A is preferably a group represented by Formula (A4), (A5), or (A6) shown above.

In the phenylene derivative (II), X is preferably a single bond or phenylene. When X is phenylene, B is preferably a 1H-tetrazol-5-yl group; and when X is a single bond, B is preferably a 2,4-dioxo-1,3-thiazolidin-5-yl group.

In the phenylene derivative (II), $Y^1$ is preferably sulfonyl or carbonyl.

In the phenylene derivative (II), $Y^2$ is preferably a $C_{1-3}$ alkylene group or a single bond, and more preferably methylene, ethylene or a single bond.

In the phenylene derivative (II), $Y^3$ is preferably carbonyl or a single bond.

In the present invention, $Y^4$ is preferably a nitrogen atom.

In the phenylene derivative (II), $Y^5$ is preferably carbonyl or a single bond.

In the phenylene derivative (II), $R^1$ is preferably a $C_{1-8}$ alkyl group (optionally substituted with 1 to 5 $C_{1-6}$ aliphatic acyl groups), a $C_{6-14}$ aryl group (optionally substituted with 1 to 5 groups selected from the group consisting of $C_{1-6}$ alkyl and $C_{6-14}$ aryl), a $C_{6-14}$ aryl-$C_{1-6}$ alkyl group (optionally substituted with 1 to 5 groups selected from the group consisting of $C_{6-14}$ aryl, halogen, $C_{1-6}$ alkoxy, and $C_{6-14}$ aryl-carbonyl), a 5- to 10-membered heterocyclic group containing 1 or 2 identical or different heteroatoms selected from the group consisting of nitrogen, oxygen, and sulfur (the heterocyclic group is optionally substituted with 1 to 5 groups selected from the group consisting of $C_{1-6}$ alkyl and $C_{6-14}$ aryl), a 5 to 10-membered heterocyclic ring-$C_{1-6}$ alkyl group containing 1 or 2 identical or different heteroatoms selected from the group consisting of nitrogen, oxygen, and sulfur, (the heterocyclic ring-$C_{1-6}$ alkyl group is optionally substituted with 1 to 5 groups selected from the group consisting of $C_{1-6}$ alkyl, $C_{6-14}$ aryl, and $C_{4-6}$ alkoxyimino), a $C_{3-7}$ cycloalkyl group (optionally substituted with oxo), a $C_{3-7}$ cycloalkyl-$C_{4-6}$ alkyl group, a $C_{6-14}$ aryl-carbonyl-$C_{1-6}$ alkyl group, or a $C_{4-6}$ aliphatic acyl group. $R^2$ is more preferably a $C_{4-8}$ alkyl group (preferably butyl, pentyl, hexyl, heptyl, or octyl) (the $C_{4-8}$ alkyl group is optionally substituted with 1 to 5 $C_{1-4}$ aliphatic acyl groups (preferably acetyl or propionyl)), a $C_{6-10}$ aryl group (preferably phenyl or naphthyl) (the $C_{6-10}$ aryl group is optionally substituted with 1 to 5 groups selected from the group consisting of $C_{1-3}$ alkyl (preferably methyl or ethyl) and $C_{6-10}$ aryl (preferably phenyl)), a $C_{6-10}$ aryl-$C_{1-3}$ alkyl group (preferably benzyl, 1-phenethyl, 2-phenethyl, 3-phenylpropyl, 1-naphthylmethyl, 2-naphthylmethyl, 2-(1-naphthyl)ethyl, or 2-(2-naphthylethyl)) (the $C_{6-10}$ aryl-$C_{1-3}$ alkyl group is optionally substituted with 1 to 5 groups selected from the group consisting of $C_{6-10}$ aryl (preferably phenyl), halogen (preferably fluorine, chlorine, or bromine), $C_{1-4}$ alkoxy (preferably methoxy or ethoxy), and $C_{6-10}$ aryl-carbonyl (preferably benzoyl)), a 5- or 6-membered heterocyclic group containing 1 or 2 identical or different heteroatoms selected from the group consisting of nitrogen, oxygen, and sulfur (the heterocyclic ring is optionally condensed with a benzene ring, preferably pyridyl, oxazolyl, thiazolyl, or quinolyl) (the heterocyclic group is optionally substituted with 1 to 5 groups selected from the group consisting of a $C_{1-3}$ alkyl group (preferably methyl or ethyl) and a $C_{6-10}$ aryl group (preferably phenyl)), a 5- or 6-membered heterocyclic ring-$C_{1-3}$ alkyl group containing 1 or 2 identical or different heteroatoms selected from the group consisting of nitrogen, oxygen, and sulfur (the heterocyclic ring is optionally condensed with a benzene ring, preferably oxazolylmethyl, thiazolylmethyl, pyridylmethyl, quinolylmethyl, thienylethyl, or thienylpropyl) (the heterocyclic ring-$C_{1-3}$ alkyl group is optionally substituted with 1 to 5 groups selected from the group consisting of a $C_{1-3}$ alkyl group (preferably methyl or ethyl), a $C_{6-10}$ aryl group (preferably phenyl), a $C_{1-4}$ alkoxyimino (preferably methoxyimino or ethoxyimino)), a $C_{5-6}$ cycloalkyl group (preferably cyclopentyl or cyclohexyl) (the $C_{5-6}$ cycloalkyl group is optionally substituted with oxo, a $C_{5-6}$ cycloalkyl-$C_{1-3}$ alkyl group (preferably cyclohexylmethyl or 2-cyclohexylethyl), a $C_{6-10}$ aryl-carbonyl-$C_{1-3}$ alkyl group (preferably benzoylmethyl or naphthoylmethyl), or a $C_{1-4}$ aliphatic acyl group (preferably butyryl).

In the phenylene derivative (II), $R^2$ is preferably a hydrogen atom, a carboxyl group, a phenyl group, or a group represented by —C(O)NR$^{13}$R$^{14}$.

In the phenylene derivative (II), $R^3$ is preferably a hydrogen atom or a $C_{6-14}$ aryl group, and more preferably a hydrogen atom or a $C_{6-10}$ aryl group (preferably phenyl or naphthyl).

In the phenylene derivative (II), $R^4$ and $R^5$ are preferably the same or different and each represent a hydrogen atom or a $C_{6-10}$ aryl group, and more preferably a hydrogen atom or phenyl.

In the phenylene derivative (II), $R^6$ and $R^7$ preferably join to form $C_{3-5}$ cycloalkane, or are the same or different and each represent a hydrogen atom or a $C_{1-3}$ alkyl group; $R^6$ and $R^7$ are more preferably the same or different and each represent a hydrogen atom or a $C_{1-3}$ alkyl group (preferably methyl, ethyl or propyl).

In the phenylene derivative (II), $R^8$ and $R^9$ are preferably the same or different and each represent a hydrogen atom or a carboxyl group, and more preferably, either $R^8$ or $R^9$ is a hydrogen atom, and the other is a carboxyl group.

In the phenylene derivative (II), $R^{10}$ is preferably a hydrogen atom, a $C_{1-4}$ alkyl group, a $C_{6-10}$ aryl group, or a 5- or 6-membered heterocyclic group containing 1 or 2 identical or different heteroatoms selected from the group consisting of nitrogen, oxygen, and sulfur (the heterocyclic group is optionally condensed with a benzene ring); and more preferably, a $C_{1-4}$ alkyl group (preferably methyl, ethyl, propyl or butyl), a $C_{6-10}$ aryl group (preferably phenyl), or a 5- or 6-membered heterocyclic group containing 1 or 2 heteroatoms selected from the group consisting of nitrogen, oxygen, and sulfur (the heterocyclic group is optionally condensed with a benzene ring) (preferably pyridyl or quinolyl).

In the phenylene derivative (II), $R^{11}$ and $R^{12}$ are preferably the same or different and each represent a hydrogen atom or a carboxyl group, more preferably a carboxyl group.

In the phenylene derivative (II), $R^{13}$ and $R^{14}$ preferably join to form a 5- or 6-membered nitrogen-containing heterocyclic ring (the nitrogen-containing heterocyclic ring is optionally condensed with a benzene ring) (preferably imidazole, pyrrolidine, piperidine, morpholine or indole), or are the same or different and each represent a hydrogen atom or a $C_{1-3}$ alkyl group (preferably methyl or ethyl).

Specifically, the following are preferable compounds as the phenylene derivative (II):

(II-1) 3-{N-(3-phenylpropionyl)-N-[2'-(1H-tetrazol-5-yl)biphenyl-4-ylmethyl]amino}benzoic acid;

(II-2) 3-{N-phenylacetyl-N-[2'-(1H-tetrazol-5-yl)biphenyl-4-ylmethyl]amino}benzoic acid;

(II-3) 3-{N-(4-phenylbutyryl)-N-[2'-(1H-tetrazol-5-yl)biphenyl-4-ylmethyl]amino}benzoic acid;

(II-4) 3-{N-cyclohexanecarbonyl-N-[2'-(1H-tetrazol-5-yl)biphenyl-4-ylmethyl]amino}benzoic acid;

(II-5) 3-{N-(pyridine-3-carbonyl)-N-[2'-(1H-tetrazol-5-yl)biphenyl-4-ylmethyl]amino}benzoic acid;

(II-6) 3-{N-pentyl-N-[4-(2,4-dioxo-1,3-thiazolidin-5-yl)benzyl]amino}benzoic acid;

(II-7) 1-[4-(2,4-dioxo-1,3-thiazolidin-5-yl)benzyl]-2-methyl-1,2,3,4-tetrahydroquinoline-7-carboxylic acid;

(II-8) 5-[4-(N-methylsulfonyl-N-phenylaminomethyl)phenyl]-1,3-thiazolidine-2,4-dione;

(II-9) 5-[4-(N-butylsulfonyl-N-phenylaminomethyl)phenyl]-1,3-thiazolidine-2,4-dione;

(II-10) 3-{N-[4-(2,4-dioxo-1,3-thiazolidin-5-yl)benzyl]-N-(methylsulfonyl)amino}benzoic acid;

(II-11) 3-{N-butylsulfonyl-N-[4-(2,4-dioxo-1,3-thiazolidin-5-yl)benzyl]amino}benzoic acid;

(II-12) 5-{4-[(2-oxo-2H-quinolin-1-yl)methyl]phenyl}-1,3-thiazolidine-2,4-dione;

(II-13) 5-{4-[(2-methylbenzimidazol-1-yl)methyl]phenyl}-1,3-thiazolidine-2,4-dione;

(II-14) 5-{4-[(2-propylbenzimidazol-1-yl)methyl]phenyl}-1,3-thiazolidine-2,4-dione;

(II-15) 5-{4-[2-(2-pyridyl)benzimidazol-1-ylmethyl]phenyl}-1,3-thiazolidin-2,4-dione;

(II-16) 5-[4-(2-phenylimidazol-1-ylmethyl)phenyl]-1,3-thiazolidine-2,4-dione;

(II-17) 1-[4-(2,4-dioxo-1,3-thiazolidin-5-yl)benzyl]-2-oxo-3-propyl-1,2-dihydroquinoline-7-carboxylic acid;

(II-18) 3-{N-cyclohexanecarbonyl-N-[4-(2,4-dioxo-1,3-thiazolidin-5-yl)benzyl]amino}benzoic acid;

(II-19) 3-{N-[4-(2,4-dioxo-1,3-thiazolidin-5-yl)benzyl]-N-(pyridine-3-carbonyl)amino}benzoic acid;

(II-20) 3-{N-[4-(2,4-dioxo-1,3-thiazolidin-5-yl)benzyl]-N-(3-phenylpropionyl)amino}benzoic acid;

(II-21) 3-{N-(biphenyl-4-carbonyl)-N-[4-(2,4-dioxo-1,3-thiazolidin-5-yl)benzyl]amino}benzoic acid;

(II-22) 3-{N-(phenylsulfonyl)-N-[4-(2,4-dioxo-1,3-thiazolidin-5-yl)benzyl]amino}benzoic acid;

(II-23) 3-{N-(4-methylphenylsulfonyl)-N-[4-(2,4-dioxo-1,3-thiazolidin-5-yl)benzyl)amino}benzoic acid;

(II-24) 3-{N-(biphenyl-4-sulfonyl)-N-[4-(2,4-dioxo-1,3-thiazolidin-5-yl)benzyl]amino}benzoic acid;

(II-25) 3-{N-(2-naphthylsulfonyl)-N-[4-(2,4-dioxo-1,3-thiazolidin-5-yl)benzyl]amino}benzoic acid;

(II-26) 3-{N-(benzylsulfonyl)-N-[4-(2,4-dioxo-1,3-thiazolidin-5-yl)benzyl]amino}benzoic acid;

(II-27) 1-[4-(2,4-dioxo-1,3-thiazolidin-5-yl)benzyl]-2-oxo-3-propyl-2, 3-1H-indole-6-carboxylic acid;

(II-28) 1-[4-(2,4-dioxo-1,3-thiazolidin-5-yl)benzyl]-2-oxo-3-propyl-2,3,4,5-tetrahydro-1H-benzo[b]azepine-8-carboxylic acid;

(II-29) 3,3-dimethyl-1-[4-(2,4-dioxo-1,3-thiazolidin-5-yl)benzyl]-2-oxo-1,2,3,4-tetrahydroquinoline-7-carboxylic acid;

(II-30) 1'-[4-(2,4-dioxo-1,3-thiazolidin-5-yl)benzyl]-2'-oxo-1',4'-dihydro-2'H-spiro[cyclopropane-1,3'-quinoline]-7'-carboxylic acid;

(II-31) 1-[4-(2,4-dioxo-1,3-thiazolidin-5-yl)benzyl]-2-propyl-1,2,3,4-tetrahydroquinoline-7-carboxylic acid;

(II-32) 3-{N-phenethyl-N-[2'-(1H-tetrazol-5-yl)biphenyl-4-ylmethyl]amino}benzoic acid, (II-33) 3-{N-[4-(2,4-dioxo-1,3-thiazolidin-5-yl)benzyl]-N-[(5-methyl-2-phenyl-1,3-oxazol-4-yl)acetyl]amino}benzoic acid, (II-34) 3-{N-[(2,5-dimethyl-1,3-oxazol-4-yl)carbonyl]-N-[4-(2,4-dioxo-1,3-thiazolidin-5-yl)benzyl]amino}benzoic acid;

(II-35) 2-oxo-3-propyl-1-[2'-(1H-tetrazol-5-ylmethyl)biphenyl-4-ylmethyl]-2,3,4,5-tetrahydro-H-benzo[b]-azepine-8-carboxylic acid;

(II-36) 3-{N-(3-cyclohexylpropanoly)-N-[2'-(1H-tetrazol-5-yl)biphenyl-4-ylmethyl]amino}benzoic acid;

(II-37) 3-{N-[(5-methyl-2-phenyl-1,3-oxazol-4-yl)acetyl]-N-[2'-(1H-tetrazol-5-yl)biphenyl-4-ylmethyl]amino}benzoic acid;

(II-38) 5-[4'-(2-phenylimidazol-1-ylmethyl)biphenyl-2-yl]-1H-tetrazole;

(II-39) 5-[4'-(4-phenylimidazol-1-ylmethyl)biphenyl-2-yl]-1H-tetrazole;

(II-40) 5-[4'-(5-phenylimidazol-1-ylmethyl)biphenyl-2-yl]-1H-tetrazole;

(II-41) 2-propyl-1-[2'-(1H-tetrazol-5-yl)biphenyl-4-ylmethyl]-1,2,3,4-tetrahydroquinoline-7-carboxylic acid;

(II-42) 3-{N-(2-oxo-2-phenylethyl)-N-[2'-(1H-tetrazol-5-yl)biphenyl-4-ylmethyl]amino}benzoic acid;

(II-43) 3-{N-(3-quinolinecarbonyl)-N-[2'-(1H-tetrazol-5-yl)biphenyl-4-ylmethyl]amino}benzoic acid;

(II-44) 3-{N-(2-naphthoyl)-N-[2'-(1H-tetrazol-5-yl)biphenyl-4-ylmethyl]amino}benzoic acid;

(II-45) 3-{N-(4-biphenylcarbonyl)-N-[2'-(1H-tetrazol-5-yl)biphenyl-4-ylmethyl]amino}benzoic acid;

(II-46) 3-{N-[(2,5-dimethyl-1,3-oxazol-4-yl)carbonyl]-N-[2'-(1H-tetrazol-5-yl)biphenyl-4-ylmethyl]amino}benzoic acid;

(II-47) 3-{N-[4-(5-methyl-1,2,4-oxadiazol-3-yl)benzoyl]-N-[2'-(1H-tetrazol-5-yl)biphenyl-4-ylmethyl]amino}benzoic acid;

(II-48) 3-{N-[4-(2-methylthiazol-4-yl)benzenesulfonyl]-N-[2'-(1H-tetrazol-5-yl)biphenyl-4-ylmethyl]amino}benzoic acid;

(II-49) 3-{N-[4-(2-pyridyl)benzoyl]1N-[2'-(1H-tetrazol-5-yl)biphenyl-4-ylmethyl]amino}benzoic acid;

(II-50) N-[3-(morpholinocarbonyl)phenyl]-N-[2'-(1H-tetrazol-5-yl)biphenyl-4-ylmethyl]-4-(2-pyridyl)benzamide;

(II-51) 3-{N-[4-(2-pyridyl)benzoyl]-N-[2'-(1H-tetrazol-5-yl)biphenyl-4-ylmethyl]amino}benzamide;

(II-52) N-[3-(morpholinocarbonyl)phenyl]-N-[2'-(1H-tetrazol-5-yl)biphenyl-4-ylmethyl]quinoline-3-carboxamide;

(II-53) 3-{N-(3-quinolinecarbonyl)-N-[2'-(1H-tetrazol-5-yl)biphenyl-4-ylmethyl]amino}benzamide;

(II-54) 3-{N-benzyl-N-[2'-(1H-tetrazol-5-yl)biphenyl-ylmethyl]amino}benzoic acid;

(II-55) 3-{N-(biphenyl-4-ylmethyl)-N-[2'-(1H-tetrazol-5-yl)biphenyl-4-ylmethyl]amino}benzoic acid;

(II-56) 3-{N-(4-chlorobenzyl)-N-[2'-(1H-tetrazol-5-yl)biphenyl-4-ylmethyl]amino}benzoic acid;

(II-57) 3-{N-(3,4-dimethoxybenzyl)-N-[2'-(1H-tetrazol-5-yl)biphenyl-4-ylmethyl]amino}benzoic acid;

(II-58) 3-{N-[2'-(1H-tetrazol-5-yl)biphenyl-4-ylmethyl]-N-[2-(2-thienyl)ethyl]amino}benzoic acid;

(II-59) 3-{N-[2-(3,4-dimethoxyphenyl)ethyl]-N-[2'-(1H-tetrazol-5-yl)biphenyl-4-ylmethyl]amino}benzoic acid;

(II-60) 3-{N-(2-cyclohexylethyl)-N-[2'-(1H-tetrazol-5-yl)biphenyl-4-ylmethyl]amino}benzoic acid;

(II-61) N-[4-(2,4-dioxo-1,3-thiazolidin-5-yl)benzyl]-N-phenyl-1-naphthalenesulfonamide;

(II-62) N-[4-(2,4-dioxo-1,3-thiazolidin-5-yl)benzyl]-N-phenyl-2-naphthalenesulfonamide;

(II-63) 3-{N-[4-(2,4-dioxo-1,3-thiazolidin-5-yl)benzyl]-N-[4-(2-methylthiazol-4-yl)benzenesulfonyl]amino}benzoic acid;

(II-64) 3-{N-[4-(2,4-dioxo-1,3-thiazolidin-5-yl)benzyl]-N-[4-(5-methyl-1,2,4-oxadiazol-3-yl)benzoyl]amino}benzoic acid;

(II-65) 3-{N-[4-(2,4-dioxo-1,3-thiazolidin-5-yl)benzyl]-N-[4-(2-pyridyl)benzoyl]amino}benzoic acid;

(II-66) 3-{N-[4-(2,4-dioxo-1,3-thiazolidin-5-yl)benzyl]-N-(quinoline-3-carbonyl)amino}benzoic acid;

(II-67) N-[4-(2,4-dioxo-1,3-thiazolidin-5-yl)benzyl]-N-(2-biphenylyl)benzenesulfonamide;

(II-68) 3-{N-(biphenyl-4-ylmethyl)-N-[4-(2,4-dioxo-1,3-thiazolidin-5-yl)benzyl]amino}benzoic acid;

(II-69) 3-{N-(2-cyclohexylethyl)-N-[4-(2,4-dioxo-1,3-thiazolidin-5-yl)benzyl]amino}benzoic acid;

(II-70) 3-{N-butylsulfonyl-N-[4-(2,4-dioxo-1,3-thiazolidin-5-yl)benzyl]amino}benzamide;

(II-71) 5-{4-[N-(3-morpholinocarbonylphenyl)-N-(2-naphthalenesulfonyl)aminomethyl]phenyl}-1,3-thiazolidine-2,4-dione;

(II-72) 5-{4-[{2-(2-naphthyl)imidazol-1-yl}methyl]phenyl}-1,3-thiazolidine-2,4-dione;

(II-73) 5-{4-[{2-(4-biphenylyl)imidazol-1-yl}methyl]}phenyl-1,3-thiazolidine-2,4-dione;

(II-74) 2-oxo-N-phenyl-N-[2'-(1H-tetrazol-5-yl)biphenyl-4-ylmethyl]valeric amide;

(II-75) 3-{N-(7-oxooctanoyl)-N-[2'-(1H-tetrazol-5-yl)biphenyl-4-ylmethyl]amino}benzoic acid;

(II-76) 3-{N-[4-(E)-methoxyimino-4-(2-thienyl)butyryl]-N-[2'-(1H-tetrazol-5-yl)biphenyl-4-ylmethyl]amino}benzoic acid;

(II-77) 3-{N-[4-(Z)-methoxyimino-4-(2-thienyl)butyryl]-N-[2'-(1H-tetrazol-5-yl)biphenyl-4-ylmethyl]amino}benzoic acid;

(II-78) 3-{N-[2-(3-benzoylphenyl)propionyl]-N-[2'-(1H-tetrazol-5-yl)biphenyl-4-ylmethyl]amino}benzoic acid; and (II-79) 3-{N-(3-oxo-1-cyclopentanecarbonyl)-N-[2'-(1H-tetrazol-5-yl)biphenyl-4-ylmethyl]amino}benzoic acid.

Among the above phenylene derivative (II), the compounds of (II-1), (II-6), (II-7), (II-8), (II-9), (II-10), (II-11), (II-15), (II-16), (II-17), (II-18), (II-19), (II-20), (II-21), (II-22), (II-23), (II-24), (II-25), (II-26), (II-27), (II-28), (II-29), (II-30), (II-32), (II-33), (II-36), (II-42), (II-63) (II-68) are particularly preferable.

The above phenylene derivative (II), pharmaceutically acceptable salts thereof and pharmaceutically acceptable esters thereof may be prepared in accordance with a method disclosed in, for example, WO2007/026962, using a known compound as a starting material. The production method of the phenylene derivative (II) disclosed in the above publication is incorporated herein by reference.

Similarly to the phenylene derivative (I), the phenylene derivative (II) of the present invention may be, when containing a basic group, formed into acid addition salts in accordance with a known method. Examples of the salts include those exemplified above in the phenylene derivative (I). Among the examples, salts of hydrohalogenic acids are preferred. Further, the above phenylene derivative (II) may be, when having a carboxyl group, converted into metal salts in accordance with a known method. Examples of such salts include those exemplified in the phenylene derivative (I). Among the examples, alkali metal salts are preferred.

The phenylene derivative (II) of the present invention may be converted into pharmaceutically acceptable esters in accordance with a known method. There is no particular limitation to the esters, so long as the esters are medically used, and pharmaceutically accepted. Specific preferable examples of ester residues include methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopenthyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl, (5-methyl-2-oxo-1,3-dioxolen-4-yl)methyl, 2-trimethylsilylethyl, and phthalidyl. More preferable examples thereof include (5-methyl-2-oxo-1,3-dioxolen-4-yl)methyl, pivaloyloxymethyl, and 1-(isopropoxycarbonyloxy)ethyl The phenylene derivative represented by Formula (II) of the present invention, salts thereof or esters thereof may form solvates (e.g., hydrates); the present invention encompasses such solvates. The present invention further encompasses compounds that can be metabolized in vivo and converted into the phenylene derivative (II), salts thereof or esters thereof (i.e., prodrugs, such as amide derivatives).

Each of the above compounds (1) and (2), and the phenylene derivatives (I) and (II) may be, if necessary, used with a known drug, such as aminoguanidine, pyridoxamine derivative, OPB-9195, biguanide compound, bridge formation inhibitor, enzyme-degrading Amadori compounds, GSH, cysteine, acetylcysteine, vitamin E, ubiquinol, aldose reductase inhibitor, carbonyl compound-trapping agent, and the like; thereby, the sustainability of the inhibitory effect on AGEs formation can be enhanced.

The carbonyl scavenger and AGEs formation inhibitor of the present invention may be administered through various routes. The administration route is not particularly limited, and may be determined according to the forms of each preparation, the patient's age, sex, and other conditions, the severity of the disease, etc. For example, tablets, pills, powders, granules, syrups, liquids, solutions, suspensions, emulsions and capsules are administered by the oral route. Injections are administered singly or in admixture with glucose, amino acid or like conventional infusions by the intravenous route, or, if necessary, administered singly by the intramuscular, intradermal, subcutaneous or intraperitoneal route. Suppositories are administered intrarectally.

Each of the above preparations may be formulated in accordance with a known method by adding, to an active ingredient, a known auxiliary agent that can be generally used in the field of pharmaceutical preparations. Examples of such auxiliary agents include excipients, binders, disintegrants, lubricants, solubilizers, flavoring agents, coating agents, and the like.

In the formation of tablets, a wide variety of carriers known in the art may be utilized. Examples of such carriers include excipients, such as lactose, sucrose, sodium chloride, glucose, urea, starch, calcium carbonate, kaolin, crystalline cellulose, silicic acid, and the like; binders, such as water, ethanol, propanol, glucose liquid, starch liquid, gelatin solution, carboxymethylcellulose, shellac, methylcellulose, potassium phosphate, polyvinylpyrrolidone, and the like; disintegrants, such as dry starch, sodium alginate, agar powder, laminaran powder, sodium hydrogencarbonate, calcium carbonate, polyoxyethylene sorbitan fatty acid ester, sodium lauryl sulfate, stearic acid monoglyceride, starch, lactose, and the like; disintegration inhibitors, such as sucrose, stearic acid, cacao butter, hydrogenated oil, and the like; absorption enhancers, such as quaternary ammonium base, sodium lauryl sulfate, and the like; humectants, such as glycerol, starch, and the like; adsorbents, such as starch, lactose, kaolin, bentonite, colloidal silica, and the like; and lubricants, such as purified talc, stearate, boric acid powder, polyethylene glycol, and the like. Where necessary, tablets may be coated with a usual coating. Examples of such tablets include a sugar-coated tablet, a gelatin-encapsulated tablet, an enteric tablet, a film-coated tablet, a double-layered tablet and a multilayered tablet.

In the formation of pills, a wide variety of carriers known in the art may be utilized. Examples of such carriers include excipients, such as glucose, lactose, starch, cacao butter, hydrogenated vegetable oil, kaolin, talc, and the like; binders, such as gum arabic powder, tragacanth powder, gelatin, ethanol, and the like; and disintegrants, such as laminaran, agar, and the like.

In the formation of suppositories, a wide variety of carriers that are known in the art can be utilized. Examples of such carriers include polyethylene glycol, cacao butter, higher alcohols, higher alcohol esters, gelatin, semi-synthetic glyceride, and the like.

In the formation of injections, it is preferable that a liquid, a solution or a suspension is sterilized and made isotonic to the blood. In the formation of such liquids, solutions, emulsions, or suspensions, any diluents commonly used in the art may be utilized. Examples thereof include water, ethyl alcohol, propylene glycol, ethoxylated isostearyl alcohol, polyoxylated isostearyl alcohol, polyoxyethylene sorbitan fatty acid esters, and the like. In this case, common salt, glucose, or glycerin can be used in the pharmaceutical preparations in an amount sufficient to produce isotonic solutions. In addition, a dissolving agent, buffer, or soothing agent may be added thereto.

Where necessary, a coloring agent, a preservative, a flavor, a flavoring, a sweetener, etc., or other pharmaceutical product may also be added.

The amount of each of the above compounds, which are active ingredients, contained in the pharmaceutical preparation is not particularly limited, and may appropriately be selected from a wide range; however, the amount is usually 1 to 70 parts by weight, and preferably 1 to 30 parts by weight of the total composition. The dose varies depending on the symptoms, patient's age, body weight, administration route, dosage form etc., but the lower limit of the dose per adult per day is usually 0.01 mg (preferably 0.1 mg, and more preferably 1 mg), and the upper limit is usually 2,000 mg (preferably 1,000 mg, and more preferably 200 mg). Such a dose may be administered as a single dose, or as several divided doses.

The above pharmaceutical preparations are administered in an effective amount to a patient diagnosed as having schizophrenia for the purpose of treating or ameliorating the schizophrenia. Therefore, the pharmaceutical preparations of the present invention may be packaged with specifications or instructions stating how to treat or ameliorate schizophrenia.

IV. Method for Treating or Ameliorating Schizophrenia

A method of the present invention for treating or ameliorating schizophrenia can be carried out by administering, to a patient diagnosed as having schizophrenia, an effective amount of a therapeutic or ameliorating agent for schizophrenia comprising the carbonyl scavenger or the AGEs formation inhibitor as an active ingredient.

The carbonyl scavenger or the AGE formation inhibitor can eliminate carbonyl stress in schizophrenia patients, and can be used with a pharmaceutically acceptable carrier or other additives in the form of a pharmaceutical composition in an amount effective for ameliorating or treating schizophrenia. A recipient (subject) of the pharmaceutical composition, an administration form, an administration route, an administration method, and an administration dose of the pharmaceutical composition (dose of the active ingredient) are as mentioned above.

V. Method of Screening a Therapeutic or Ameliorating Agent for Schizophrenia The present invention provides an effective method for developing drugs and food useful for treating or ameliorating schizophrenia, or preventing the development of schizophrenia. Specifically, the present invention provides a method (screening method) for screening a candidate substance effective for treating or ameliorating schizophrenia, or preventing the development of schizophrenia.

The method can be carried out by selecting, from test substances, substances having an effect of carbonyl removal, or an inhibitory effect on the formation of carbonyl-modified proteins (inhibitory effect on AGE formation). Preferably, the method can be carried out by selecting, from test substances, substances having the above effect using an AGEs formation inhibitory effect as an index.

There is no particular limitation to the test substances used in the screening method. Examples thereof include single compounds such as natural compounds, organic compounds, inorganic compounds, proteins, and peptides, as well as compositions such as compound libraries, gene library expression products, cell extracts, cell culture supernatants, fermented microbial products, marine biological extracts, plant extracts, and the like.

The presence or absence of an AGEs formation inhibitory effect can be confirmed by the test (i) below:

(i) Plasma is collected from a non-diabetic renal failure patient who undergoes dialysis, the test substance is added to the plasma, and the amount of pentosidine produced after a certain period of time is measured using pentosidine, which is a typical AGE, as an index.

The details of the method can be referred to as Example 1. The AGE formation inhibitory effect of the test substance can be evaluated by comparing the amount of pentosidine produced by the test substance with that produced by pyridoxamine, which is used in place of the test substance as a positive control. In other words, the test substance that produces an amount of pentosidine that is equal or smaller than that produced by pyridoxamine, i.e., the positive control, can be evaluated as exhibiting an AGE formation inhibitory effect.

The presence or absence of an AGE formation inhibitory effect can also be confirmed by the test (ii) below:

(ii) A radical-capturing ability of the test substance is measured in a phenylalanine-radical reaction system.

The above method utilizes a hydroxy radical produced by the reaction between hydrogen peroxide and copper sulphate hydroxylating phenylalanine to form o- or m-tyrosine. Specifically, this method can be carried out by comparing the amount of the o- or m-tyrosine produced when a test substance is added to a reaction system containing hydrogen peroxide, copper sulphate and phenylalanine with the amount of the o- or m-tyrosine produced when a test substance is not added. If the amount of the o- or m-tyrosine produced is suppressed with the addition of a test substance, the test substance can be considered as having radical-capturing ability, and thus having an AGE formation inhibitory effect. A specific measurement method is described in detail below.

<Measurement Method of Radical-Capturing Ability>

A preparation liquid (total amount: 500 μl) in which phenylalanine at a final concentration of 1 mM, the test substance at final concentrations of 0.1 mM, 0.5 mM or 2.5 mM, hydrogen peroxide at a final concentration of 5 mM, and copper sulphate at a final concentration of 0.1 mM are dissolved in a 200 mM phosphate buffer (pH 7.4) is incubated for 4 hours at 37° C. for reaction. After completion of the reaction, DTPA (diethylene triamine pentaacetic acid) at a final concentration of 1 mM and 260 units of catalase are added to halt the reaction. Subsequently, the amount of o- and m-tyrosine thereby produced is measured using HPLC under the following conditions.

HPLC Condition

Column: $C_{18}$ reversed-phase column (4.6×250 mm, 5 μm, product of Nomura Chemical Co., Ltd.)

Mobile phase:
　buffer A: 0.10% trifluoroacetic acid
　buffer B: 80% acetonitrile containing 0.08% trifluoroacetic acid Gradient: concentration of buffer B increased from 6.5% to 10% in 25 minutes.

Flow rate: 0.6 ml/minute

Detection: detection performed using a fluorescence detector (RF-10A, Shimadzu Corp.) at an excitation wavelength of 275 nm, and a fluorescence wavelength of 305 nm.

It is preferable that the candidate substance does not cause vitamin $B_6$ deficiency. Therefore, it is preferable to further confirm whether the test substances cause vitamin $B_6$ deficiency by either test (a) or (b) described below.

(a) To a solution of vitamin $B_6$, the test substance is added; and, after a certain period of time, the amount of vitamin $B_6$ remaining is determined.

(b) To a normal rat, the test substance is administered; and, after a certain period of time, the presence or absence of vitamin $B_6$ deficiency is determined.

The candidate substance selected by the above method (selection of a candidate substance) undergoes, if required, other pharmacological tests, clinical tests, or toxicity tests, thereby providing an active ingredient more effective and safer for humans, for use in a therapeutic, ameliorating, or preventive agent for schizophrenia.

The candidate substance thus obtained is prescribed or formulated into pharmaceutical preparations according to known procedures, thereby providing a therapeutic, ameliorating, or preventive agent for schizophrenia.

EXAMPLES

The following examples are given below to describe the present invention in greater detail. However, these examples are illustrative only, and in no way limit the invention.

Example 1

Genetic and Biochemical Analyses on Patient with Severe Schizophrenia

A schizophrenic patient (male, 60 years, weight 75.5 kg) hospitalized in a psychiatric hospital (hereinafter "Patient A") underwent analysis of the glyoxalase I gene, as well as measurement of the erythrocyte glyoxalase activity, the serum AGE level, and the quantity of serum vitamin $B_6$. Patient A is one of four siblings, two of whom committed suicide; he and the other remaining sibling are currently hospitalized in a psychiatric hospital. Patient A has been diagnosed with severe familial schizophrenia.

Measurement Methods (1) Measurement of Erythrocyte Glyoxalase Activity

The erythrocyte glyoxalase activity was measured according to the method of McLellan et al. (McLellan AC, Thornalley PJ: Glyoxalase activity in human red blood cells fractioned by age. Mech Ageing Dev 48: 63-71, 1989). Specifically, disrupted erythrocytes were added to a hemithioacetal solution produced from methylglyoxal and glutathione, and the quantity of S-D-lactoylglutathion formed was measured at an absorption wavelength of 240 nm using a spectrophotometer. The S-D-lactoylglutathion concentration was determined from the measured value, using the molar absorption coefficient $\Delta\epsilon_{240}=2.86$ $Mm^{-1}cm^{-1}$, and converted to units. One unit represents 1 µmol of S-D-lactoylglutathion formed by $10^6$ erythrocytes per minute.

(2) Measurement of Serum AGE Level

Pentosidine was used as an index for the AGE level. Pentosidine was measured as follows: collected serum was hydrolyzed in 6N HCl at 110° C. for 16 hours under nitrogen gas, and then quantitative analysis was conducted at the excitation-absorption wavelength (335/385 nm) by reverse-phase high-performance liquid chromatography (HPLC) using synthetic pentosidine of a known concentration as a standard sample.

(3) Measurement of Quantity of Serum Vitamin $B_6$

The pyridoxamine level, pyridoxine level, and pyridoxal level in serum were measured as the quantity of serum vitamin $B_6$. The measurement was conducted by a provider of laboratory testing services (SRL Corporation) by quantitative analysis using reverse-phase high-performance liquid chromatography (HPLC).

Measured Results (1) Erythrocyte Glyoxalase Activity (FIG. 4)

The erythrocyte glyoxalase activity was calculated based on the erythrocyte count at 10% hematocrit as $0.6\times10^9$/ml. As a result, the erythrocyte glyoxalase I activity of Patient A was 2.9 mUnit/$10^6$ RBC, which was lower than the erythrocyte glyoxalase I activity ($6.1\pm0.7$ mUnit/$10^6$ RBC) of healthy subjects (n=5) (FIG. 4).

(2) Analytical Results of Glyoxalase I Gene (FIG. 5)

The results of analysis of the glyoxalase I gene for Patient A are shown in FIG. 5. A comparison of the glyoxalase I gene of Patient A with that of a healthy subject revealed that an A (adenine) was inserted at position 80 of the glyoxalase I gene of Patient A (a point mutation), resulting in a frameshift that prevented normal expression of glyoxalase I. This shows that the lowered erythrocyte glyoxalase activity of Patient A mentioned in Section (1) above can be attributed to the abnormality of the glyoxalase I gene (the frameshift caused by the point mutation).

(3) Measurement of Serum AGE Level (FIG. 6)

FIG. 6 shows a comparison of the serum AGE levels (the quantities of pentosidine) between Patient A and healthy subjects. The results show that the serum AGE level of Patient A was 0.368 nmol/ml, which was significantly higher than the serum AGE level of $0.128\pm0.04$ nmol/ml of the healthy subjects (n=5). The serum AGE level of Patient A when converted to the quantity of pentosidine per 1 mg of protein was 5 pmol/mg protein, which proved to be three times higher than the $1.7\pm0.4$ pmol/mg protein of the healthy subjects.

The estimated glomerular filtration rate (eGFR) of Patient A (60 years, weight: 75.5 kg, creatinine: 1.05 mg/dl) measured using the MDRD formula was 76.7 ml/min, and the estimated creatinine clearance (eCCr) measured using the Cockcroft-Gault formula was 79.9 ml/min, showing a slight decrease in renal function. However, since such a slight decrease in renal function could not lead to the above-mentioned level of increase in AGEs (such as pentosidine), factors for the increased AGEs (such as pentosidine), other than diabetes and renal failure, were considered to be present in schizophrenia. Further taking into account the glyoxalase I deficiency, the increased serum AGE level in schizophrenic patients can be attributed to an abnormality in detoxification of the AGE precursor due to the lowered glyoxalase I activity.

(4) Quantity of Serum Vitamin $B_6$

Of the serum vitamin $B_6$ levels of Patient A, the pyridoxamine and pyridoxine levels were at or below the detection limits, as with the healthy subjects (the detection limit of pyridoxamine: 0.2 ng/ml; the detection limit of pyridoxine: 3.0 ng/ml). On the other hand, the pyridoxal level of Patient A was 2.8 ng/ml, which was significantly lower than that of the healthy subjects ($14.8\pm0.3$ ng/ml, n=2). It is noted that the pyridoxal reference level for males is 6.0 to 40.0 ng/ml. Pyridoxal acts to remove carbonyls in blood. Therefore, the reduced quantity of serum pyridoxal (vitamin $B_6$) in the schizophrenic patient was considered to be the result of pyridoxal consumption within the body due to the need to remove carbonyls.

The above results suggest that the condition of schizophrenia was associated with the carbonyl stress attributed to the glyoxalase I deficiency. Specifically, it is believed that schizophrenic patients have lowered glyoxalase I activity due to abnormalities in the glyoxalase I gene, and this lowered glyoxalase I activity increases the carbonyl stress (i.e., increase the AGEs), causing the depletion of vitamin $B_6$, leading to the aggravation of the condition of schizophrenia. Therefore, the lowered glyoxalase I activity, increased carbonyl stress (increased AGEs), and reduced vitamin $B_6$ can serve as indices for a diagnosis of schizophrenia. Furthermore, AGE inhibitors (AGE-formation inhibitors), as well as carbonyl scavengers such as vitamin $B_6$ and edaravone, are considered effective as agents for treating schizophrenia or ameliorating the condition of schizophrenia.

Example 2

Measurement of the AGE Content in the Skin

AGE contents in the skin were measured in healthy subjects (12 females and 12 males, a total of 24 subjects; average age: 48.88+3.17 years) and schizophrenic patients (12 females and 12 males, a total of 24 subjects; average age: 48.38+2.23 years), using an AGE Reader (manufactured by DiagnOptics, the Netherlands).

FIG. 7 shows a comparison of the AGE contents in the skin between the healthy subjects and schizophrenic patients. The results show that the AGE contents in the skin of the schizophrenic patients are significantly increased as compared to those of the healthy subjects. FIG. 8A and FIG. 8B show comparison of the AGE contents in the skin between the healthy subjects and schizophrenic patients according to age. The results revealed a strong positive correlation between the AGE content and age for the healthy subjects, but no such correlation was observed for the schizophrenic patients (FIG. 8A). However, as shown in FIG. 8B, the AGE contents in the skin of the schizophrenic patients tended to be high as compared to the healthy subjects, even for those over the age of 50, not to mention those under the age of 50.

This shows that, as previously demonstrated in Example 1, schizophrenic patients have increased AGE contents over healthy subjects, and this tendency can also be evaluated using the AGE Reader for measuring AGE contents in the skin.

Example 3

Analysis of Glyoxalase I Gene of Schizophrenic Patients (1) Analysis of the glyoxalase I (GLO-I) gene was conducted on schizophrenic patients (n=700) and healthy subjects (n=600).

A frameshift mutation in the GLO-I gene (an insertion of a single base between positions 79 and 80 of the base sequence (SEQ ID NO: 1) of the coding region of the GLO-I gene) was identified by PCR-direct sequencing using Blend Taq (TOYOBO Cat#BTQ-101S), in which PCR was performed using PCR primers, F: 5'-GAGTTTGCCTCCTTTATGCG-3' (SEQ ID NO: 8) and R: 5'-AACAGATCCCCTCCACACTT-3' (SEQ ID NO: 9), under the conditions of (i) 1 cycle of 94° C. for 2 minutes; (ii) 40 cycles of 94° C. for 30 seconds, 62.5° C. for 20 seconds, 72° C. for 30 seconds; and (iii) 1 cycle of 72° C. for 2 minutes. A base substitution mutation (the mutation of alanine to cytosine at position 332 of the base sequence (SEQ ID NO: 1) of the coding region of the GLO-I gene), inducing the mutation of the amino acid (Glu→Ala) at position 111 of the GLO-I was identified by PCR-direct sequencing using Blend Taq (TOYOBO Cat#BTQ-101S), in which PCR was performed using F: 5'-TCAGAGTGTGT-GATTTCGTG-3' (SEQ ID NO: 10) and R: 5'-CATGGT-GAGATGGTAAGTGT-3' (SEQ ID NO: 11), under the conditions of (i) 1 cycle of 94° C. for 2 minutes; (ii) 40 cycles of 94° C. for 30 seconds, 62.5° C. for 20 seconds, 72° C. for 30 seconds; and (iii) 1 cycle of 72° C. for 2 minutes.

The results revealed a significant difference mainly in the single nucleotide polymorphism (SNP) in which Glu is replaced with Ala at position 111 of the amino acid sequence (SEQ ID NO: 2) of GLO-I. While four cases of Ala/Ala homozygotes were detected among schizophrenic patients (n=700), no such cases were found among healthy subjects (n=600).

(2) Erythrocyte glyoxalase activities were measured in three of the four schizophrenic patients with Ala/Ala homozygotes, according to the method described in Section (1) of Example 1. The medical histories and conditions of these three patients are as follows:

(a) Patient B (inpatient): female, 50 years, CREAT 0.57, onset age 41 years:

Although delusions or hallucinations have currently faded, negative symptoms (e.g., apathy, affective flattening) are prominent.

(b) Patient C (inpatient): male, 66 years, CREAT 0.86, onset age 15 years:

Serious negative symptoms are present, and little or no voluntary speech is produced; the patient only nods yes or no in reply to questions.

(c) Patient D (outpatient): male, 50 years, CREAT 0.72, onset age 19 years:

The patient has the delusion of being "harassed by neighbors", and has repeatedly changed addresses.

Similarly, erythrocyte glyoxalase activities were also measured in schizophrenic patients with Glu/Ala heterozygotes and Glu/Glu homozygotes, as well as in healthy subjects. The results are shown in FIG. 9. The results show that the schizophrenic patients with Ala/Ala homozygotes have significantly lowered erythrocyte glyoxalase activity. Further, a construct (pAcGFP-GLO1-Ala) consisting of GFP and mutant GLO-I having an Ala at position 111 of the amino acid sequence (SEQ ID NO: 2) of GLO-I; and a construct (pAcGFP-GLO1-Glu) consisting of GFP and normal GLO-I having a Glu at position 111 were each expressed in COS cells according to a routine method, and the GOL-I activities were measured. As a result, mutant GLO-I was confirmed to have significantly lowered GLO-I activity as compared to normal GLO-I (FIG. 10).

(3) FIG. 11 shows the levels of mRNA expression of GLO-I assayed for the schizophrenic patients (four) with Ala/Ala homozygotes and schizophrenic Patient A of Example 1 (GLO-1-deficient due to the frameshift caused by the point mutation of a single allele of the GLO-I gene (between positions 79 and 80 of the base sequence of the coding region of the GLO-I gene)). The results showed that the level of mRNA expression of GLO-I in the frameshift-type Patient A was decreased by 50%. The level of mRNA expression of GLO-I in the schizophrenic patients with Ala/Ala homozygotes were also decreased by 20%. This suggests the possibility that a 20% decrease, if not a 50% decrease, in the level of mRNA expression of GLO-I (GLO-I activity) will pose the risk of schizophrenia.

Example 4

Analysis of Glyoxalase I Gene and Biochemical Analysis of Schizophrenia Patients (Summary)

Schizophrenic patients were divided into the frameshift type [n=2], homozygous-type Ala/Ala[n=5], and heterozygous-type Glu/Ala [n=1]; and the glyoxalase I activity (mU-nit/$10^6$ RBC), pentosidine activity (pmol/mg protein), blood vitamin $B_6$ contents (ng/ml) (pyridoxal, pyridoxamine, and pyridoxine), blood vitamin B12 content (pg/ml), blood folate content (ng/ml), blood homocysteine content (nmol/ml), creatinine content (mg/dl), and eGFR (ml/min/1.73 $m^2$) were measured for each patient. The measurement of each activity and content was conducted according to the method described in Example 1, or a routine method. As a control, measurements were similarly conducted on healthy subjects [n=7] unaffected with schizophrenia (homozygous-type Glu/Glu).

The results, including whether or not each patient has diabetes, are shown in FIG. 12.

The results revealed the tendency for the schizophrenic patients of all types to have lowered GLO-I activities and increased pentosidine levels (AGE levels) as compared to the healthy subjects. Since all of these patients had normal creatinine and eGFR, and were not also diabetic, the increased pentosidine levels could not be explained by lowered renal function or hyperglycemia. The increased pentosidine levels are thus considered attributable to the lowered GLO-I activities. Patient MZ-65, who has a markedly high pentosidine level, is a severely schizophrenic patient who suffers from serious negative symptoms, and produces little or no voluntary speech.

Among the schizophrenic patients, the frameshift-type patients in particular showed a marked tendency for lowered GLO-I activities, increased pentosidine levels (AGE levels), reduced pyridoxal levels, and increased homocysteine contents, as compared to the healthy subjects. This suggests that the lowered GLO-I contributes to the pathogenesis of this type of schizophrenic patient. That is, the above analytical results are all considered attributable to the lowered GLO-I in the body: the lowered GLO-I causes the carbonyl level to increase, and consequently, the AGE level (pentosidine content) in the body increases to reduce the quantity of vitamin $B_6$ (pyridoxal) for removing the AGEs. Additionally, because vitamin $B_6$ plays an important role in the formation of homocysteine, the lowered quantity of vitamin $B_6$ is also considered to be reflected in the increased homocysteine levels. Hence, the use of these biochemical levels as indices enables easy diagnosis of schizophrenia.

Test Example 1

Inhibitory Effect of Edaravone Analogues on AGE Formation (1) 1-(5-Hydroxy-3-methyl-1-phenyl-1H-pyrazol-4-yl)-6-methyl-1,3-dihydro-3,4-furo[3,4-c]pyridin-7-ol (hereinafter "TM-2002") was investigated for its inhibitory effect on the formation of pentosidine, which is a representative example of an AGE.

Plasma was collected from hemodialysis patients prior to dialysis with the patients' consent, and the plasma was filtered and sterilized. To the plasma (450 µL) was added solutions of TM-2002 in dimethylsulfoxide (50 µL) (final concentrations: 0.8, 2.0, and 5.0 mM), and the mixtures were incubated for 1 week at 37° C. The levels of the pentosidine formation were measured.

Pentosidine was measured as follows. To each sample (50 µL) after incubation was added an equal volume of 10% trichloroacetic acid, and the mixture was subsequently centrifuged at 5,000 g for 5 minutes. After the supernatant was removed, the pellet was washed with 5% trichloroacetic acid (300 µL). The pellet was dried under reduced pressure, and subsequently hydrolyzed in a 6N HCl solution (100 µL) under a nitrogen atmosphere for 16 hours at 110° C. To the acid hydrolysate was then added 5N NaOH (100 µL) and 0.5 M phosphate buffer (pH 7.4) (200 µL); the mixture was subsequently filtered through a micropore filter with 0.5 µm pores and diluted with PBS.

The concentration of the released pentosidine was measured by reverse-phase HPLC using a fluorescence detector (RF-10A, Shimadzu Corporation) (Miyata, T. et al.; Proc. Natl. Acad. Sci. USA, Vol. 93, p. 2353-2358, 1996). The effluent was monitored at the excitation/emission wavelength of 335/385 nm. Synthetic pentosidine was used as the reference material. The detection limit of pentosidine was 0.1 pmol/mg protein.

The inhibitory effect was evaluated by comparison with a positive control (pyridoxamine (Sigma)), which was reacted in the same manner as Compound TM-2002. Similarly, aminoguanidine, olmesartan, and edaravone were also investigated for their inhibitory effects. The results (the quantities of pentosidine: nmol/ml) are shown in FIG. 13, wherein the "control" hereinbelow means a negative control using only the solvent. It is understood from these results that TM-2002 significantly inhibits the pentosidine formation as compared to pyridoxamine used as the positive control.

(2) Other edaravone analogues (Compounds (1) or (2)) were investigated for their inhibitory activities on pentosidine formation in the same manner as in Section (1) above, except that the samples were incubated with BSA and arabinose instead of the patient plasma. The results are shown in the following tables. In the tables, "-" means that the test was not conducted.

TABLE 4

| No. | Chemical Name | Chemical Structure | Pentosidine Formation Ratio (%) at 5 mM Drug Concentration |
|---|---|---|---|
| 1 | 2-(3-amino-5-oxo-1-phenyl-4,5-hydro-1H-pyrazol-4-yl)-2-oxo-N-phenyl-acetamide | 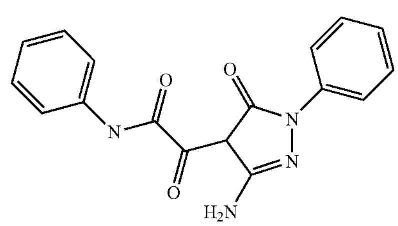 [SMILES: NC1=NN(c2ccccc2)C(=O)C1C(=O)C(=O)Nc1ccccc1] | — |
| 2 | 2-(3-amino-5-oxo-1-phenyl-4,5-hydro-1H-pyrazol-4-yl)-2-oxo-N-thiazol-2-yl-acetamide | 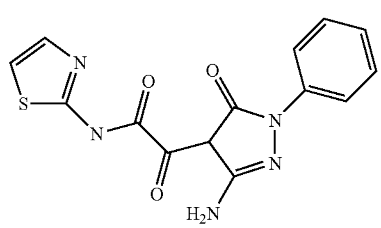 [SMILES: NC1=NN(c2ccccc2)C(=O)C1C(=O)C(=O)Nc1nccs1] | — |

TABLE 4-continued

| No. | Chemical Name | Chemical Structure | Pentosidine Formation Ratio (%) at 5 mM Drug Concentration |
|---|---|---|---|
| 3 | 2-(3-amino-5-oxo-1-phenyl-4,5-hydro-1H-pyrazol-4-yl)-2-oxo-acetamide | 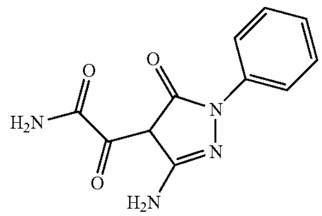 [SMILES: NC(=O)C(=O)C1C(=O)N(c2ccccc2)N=C1N] | — |
| 4 | 2-(3-amino-5-oxo-1-phenyl-4,5-hydro-1H-pyrazol-4-yl)-N-(3,4-dimethyl-phenyl)-4-oxo-butyramide | 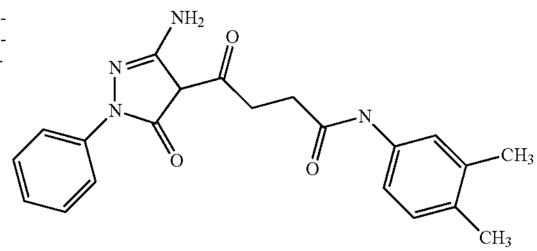 | — |
| 5 | 2-(4-amino-phenyl)-4-(2-hydroxy-ethyl)-5-methyl-2,4-hydro-pyrazol-3-one | 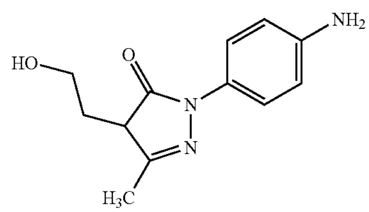 [SMILES: CC1=NN(c2ccc(N)cc2)C(=O)C1CCO] | — |
| 6 | 5-amino-2-phenyl-4-(1-phenyl-1H-tetrazol-5-ylsulfanyl)-2,4-dihydro-pyrazol-3-one | 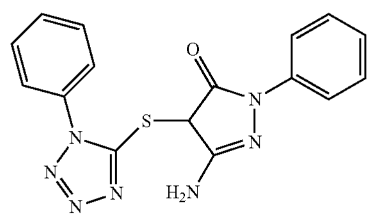 [SMILES: NC1=NN(c2ccccc2)C(=O)C1Sc1nnnn1-c1ccccc1] | — |
| 7 | 3-(3-methyl-5-oxo-1-penyl-4,5-dihydro-1H-pyrazol-4-yl)-propionic acid | 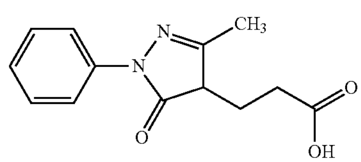 [SMILES: CC1=NN(c2ccccc2)C(=O)C1CCC(=O)O] | 64.64 |

TABLE 5

| No. | Chemical Name | Chemical Structure | Pentosidine Formation Ratio (%) at 5 mM Drug Concentration |
|---|---|---|---|
| 8 | N-(3-methyl-5-oxo-1-phenyl-4,5-dihydro-1H-pyrazol-4-yl)-acetamide | 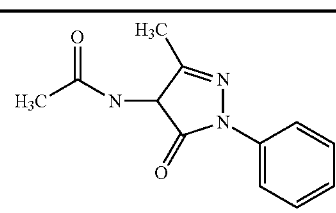 | — |

TABLE 5-continued

| No. | Chemical Name | Chemical Structure | Pentosidine Formation Ratio (%) at 5 mM Drug Concentration |
|---|---|---|---|
| 9 | 4-[(5-hydroxy-3-methyl-1-phenyl-1H-pyrazol-4-yl)-phenyl-methyl]-5-methyl-2-phenyl-2,4-dihydro-pyrazol-3-one | 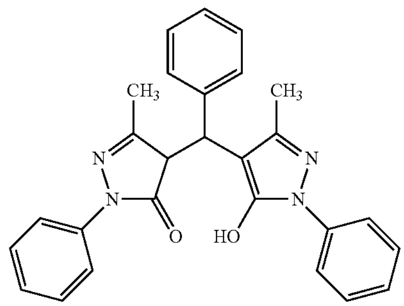 [SMILES: CC1=NN(c2ccccc2)C(=O)C1C(c1ccccc1)c1c(C)nn(-c2ccccc2)c1O] | 7.52 |
| 10 | 2-phenyl-3a,4,5,6-tetrahydro-2H-cyclopentapyrazol-3-one | 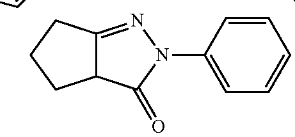 | — |
| 11 | 4-methyl-N-(3-methyl-5-oxo-1-phenyl-4,5-dihydro-1H-pyrazol-4-yl)-benzenesulfonamide | 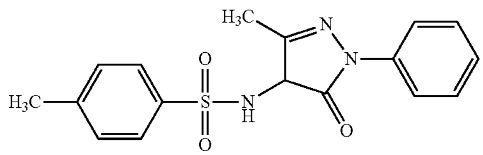 [SMILES: CC1=NN(c2ccccc2)C(=O)C1NS(=O)(=O)c1ccc(C)cc1] | — |
| 12 | N-(3-methyl-5-oxo-1-phenyl-4,5-dihydro-1H-pyrazol-4-yl)-acetamide | 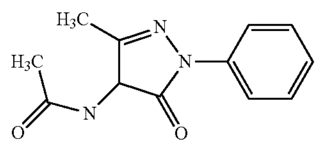 [SMILES: CC(=O)NC1C(=O)N(c2ccccc2)N=C1C] | 54.21 |
| 13 | 5-methyl-2-(3-nitro-phenyl)-4-(1-phenyl-1H-tetrazol-5-ylsulfanyl)-2,4-dihydro-pyrazol-3-one | 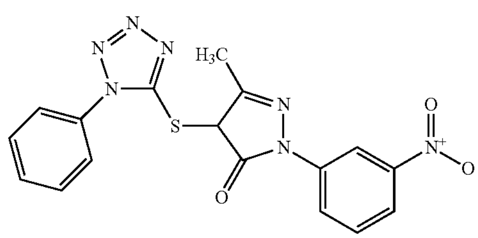 | 74.66 |
| 14 | N-[5-oxo-1-phenyl-4-(1-phenyl-1H-tetrazol-5-ylsulfanyl)-4,5-dihydro-1H-pyrazol-3-yl]-benzamide | 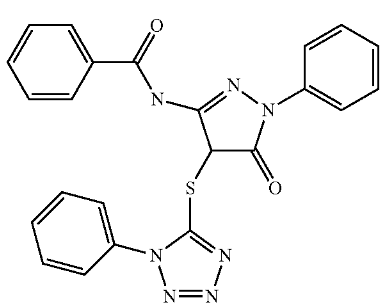 [SMILES: O=C(NC1=NN(c2ccccc2)C(=O)C1Sc1nnnn1-c1ccccc1)c1ccccc1] | 61.27 |
| 15 | 4-(hydroxy-phenyl-methyl)-2-phenyl-5-trifluoromethyl-2,4-dihydro-pyrazol-3-one | 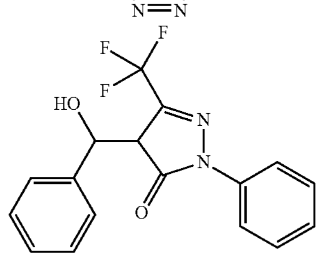 | — |

TABLE 6

| No. | Chemical Name | Chemical Structure | Pentosidine Formation Ratio (%) at 5 mM Drug Concentration |
|---|---|---|---|
| 16 | 4-(1-hydroxyimino-ethyl)-2,5-diphenyl-2,4-dihydro-pyrazol-3-one | 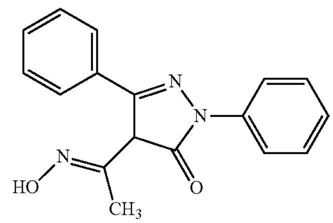 [SMILES: C/C(=N\O)C1C(=O)N(c2ccccc2)N=C1c1ccccc1] | — |
| 17 | 5,5'-dimethyl-2,2'-diphenyl-2,4,2',4'-tetrahydro-[4,4']bipyrazole-3,3'-dione | 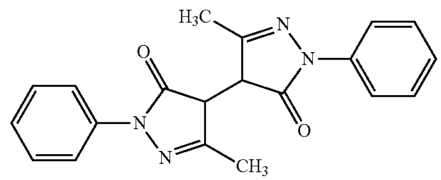 [SMILES: CC1=NN(c2ccccc2)C(=O)C1C1C(=O)N(c2ccccc2)N=C1C] | 60.96 |
| 18 | 2-(4-chloro-phenyl)-4-ethyl-5-methyl-2,4-dihydro-pyrazol-3-one | 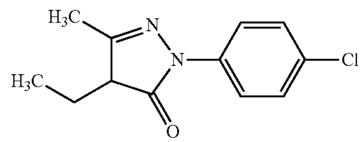 [SMILES: CCC1C(=O)N(c2ccc(Cl)cc2)N=C1C] | — |
| 19 | 4-[4-(4-methoxy-phenyl)-thiazol-2-ylsulfanyl]-5-methyl-5-phenyl-2,4-dihydro-pyrazol-3-one | 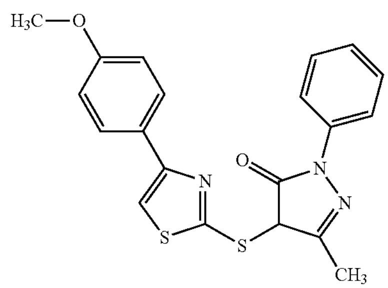 [SMILES: COc1ccc(-c2csc(SC3C(=O)N(c4ccccc4)N=C3C)n2)cc1] | 40.19 |
| 20 | 4-(2-oxo-2-phenyl-ethyl)-2-phenyl-5-propyl-2,4-dihydro-pyrazol-3-one | 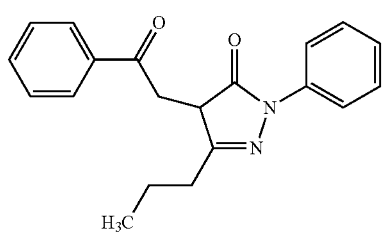 [SMILES: CCCC1=NN(c2ccccc2)C(=O)C1CC(=O)c1ccccc1] | 83.12 |
| 21 | 5-methyl-2-phenyl-4-(4-p-toluyl-thiazol-2-ylsulfanyl)-2,4-dihydro-pyrazol-3-one | 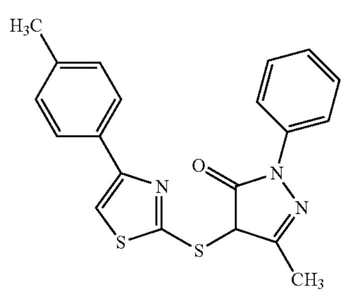 [SMILES: CC1=NN(c2ccccc2)C(=O)C1Sc1nc(-c2ccc(C)cc2)cs1] | 42.07 |

TABLE 6-continued

| No. | Chemical Name | Chemical Structure | Pentosidine Formation Ratio (%) at 5 mM Drug Concentration |
|---|---|---|---|
| 22 | 2-(4-fluoro-phenyl)-4-[[1-(4-fluoro-phenyl)-5-hydroxy-3-methyl-1H-pyrazol-4-yl]-(2-hydroxy-phenyl)-methyl]-5-methyl-2,4-dihydro-pyrazol-3-one | 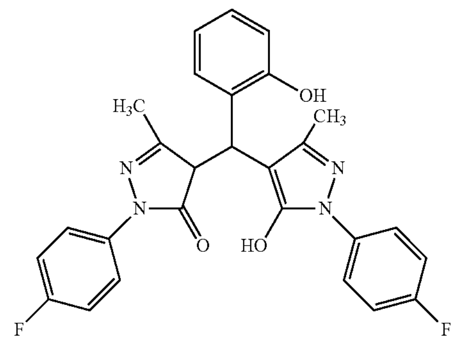 [SMILES: CC1=NN(c2ccc(F)cc2)C(=O)C1C(c1ccccc1O)c1c(C)nn(-c2ccc(F)cc2)c1O] | 2.9 |

TABLE 7

| No. | Chemical Name | Chemical Structure | Pentosidine Formation Ratio (%) at 5 mM Drug Concentration |
|---|---|---|---|
| 23 | N-(3,4-dimethyl-phenyl)-2-(3-methyl-5-oxo-1-phenyl-4,5-dihydro-1H-pyrazol-4-yl)-2-oxo-acetamide | 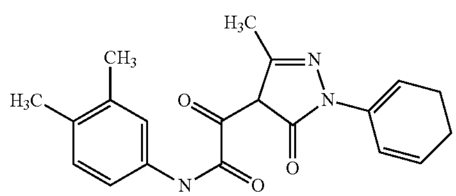 [SMILES: CC1=NN(C2=CCCC=C2)C(=O)C1C(=O)C(=O)Nc1ccc(C)c(C)c1] | — |
| 24 | 5-(4-chloro-benzoyl)-4,4-dihydroxy-2-phenyl-2,4-dihydro-pyrazol-3-one | 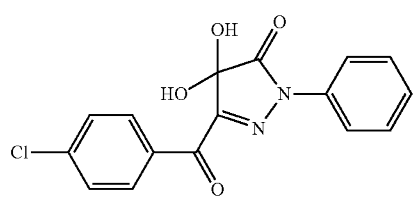 [SMILES: O=C(C1=NN(c2ccccc2)C(=O)C1(O)O)c1ccc(Cl)cc1] | — |
| 25 | sodium 4-hydroxy-3-methyl-5-oxo-1-phenyl-4,5-dihydro-1H-pyrazole-4-sulfonate | 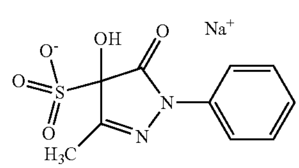 [SMILES: [Na+] ; CC1=NN(c2ccccc2)C(=O)C1(O)S(=O)(=O)[O-]] | 38.80 |
| 26 | 5-methyl-4,4-dimorpholine-4-yl-2-phenyl-2,4-dihydro-pyrazol-3-one | 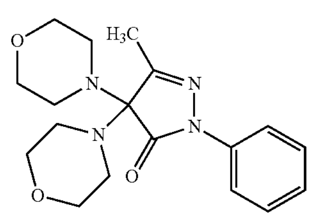 [SMILES: CC1=NN(c2ccccc2)C(=O)C1(N1CCOCC1)N1CCOCC1] | 50.68 |

TABLE 7-continued

| No. | Chemical Name | Chemical Structure | Pentosidine Formation Ratio (%) at 5 mM Drug Concentration |
|---|---|---|---|
| 27 | Sodium 3-benzoylamino-4-hydroxy-5-oxo-1-phenyl-4,5-dihydro-1H-pyrazole-4-sulfonate | 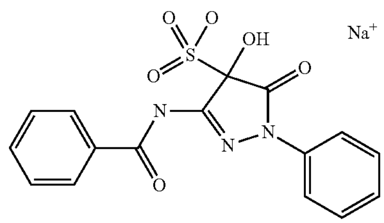 [SMILES: O=C(NC1=NN(c2ccccc2)C(=O)C1(O)S(=O)(=O)O)c1ccccc1 ; [Na+]] | 2.83 |
| 28 | 3-methyl-1-phenyl-5-oxo-4-spiro(3-oxo-2,3-dihydro-benzo[b]thiophen-2-yl)-4,5-dihydro-1H-pyrazole | 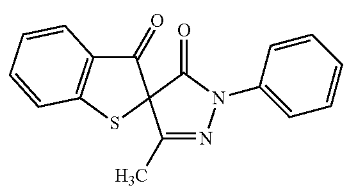 [SMILES: CC1=NN(c2ccccc2)C(=O)C12Sc1ccccc1C2=O] | 22.83 |
| 29 | 4,4,5-trimethyl-2-phenyl-2,4-dihydro-pyrazol-3-one | 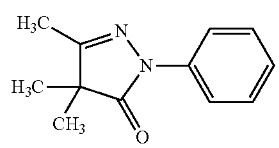 | — |
| 30 | 4,10-dimethyl-2,8,11-triphenyl-2,3,8,9-tetraza-dispiro[4.0.4.1]undeca-3,9-diene-1,7-dione | 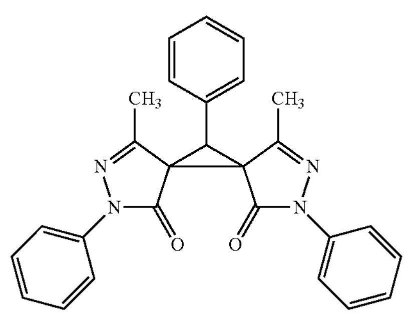 [SMILES: CC1=NN(c2ccccc2)C(=O)C12C(c1ccccc1)C21C(=O)N(c2ccccc2)N=C1C] | 62.43 |

TABLE 8

| No. | Chemical Name | Chemical Structure | Pentosidine Formation Ratio (%) at 5 mM Drug Concentration |
|---|---|---|---|
| 31 | 2-(2-chloro-phenyl)-4-(3-ethoxy-4-hydroxy-benzylidene)-5-methyl-2,4-dihydro-pyrazol-3-one | 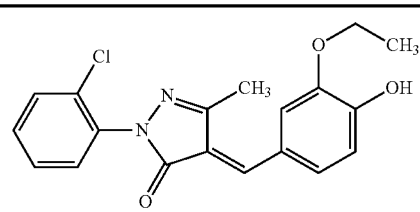 | 15.57 |

TABLE 8-continued

| No. | Chemical Name | Chemical Structure | Pentosidine Formation Ratio (%) at 5 mM Drug Concentration |
|---|---|---|---|
| 32 | 2-(2-chloro-phenyl)-4-(4-dimethylamino-benzylidene)-5-methyl-2,4-dihydro-pyrazol-3-one | 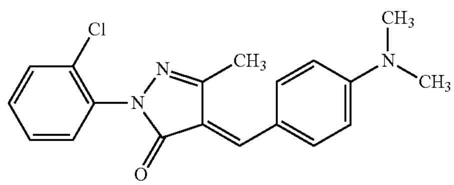 [SMILES: CC1=NN(c2ccccc2Cl)C(=O)/C1=C/c1ccc(N(C)C)cc1] | 8.7 |
| 33 | 5-methyl-4-(3-phenyl-allylidene)-2-(3-trifluoromethyl-phenyl)-2,4-dihydro-pyrazol-3-one | 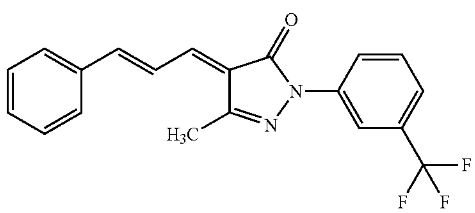 [SMILES: CC1=NN(c2cccc(C(F)(F)F)c2)C(=O)/C1=C/C=C/c1ccccc1] | 80.08 |
| 34 | 3-{5-[3-methyl-5-oxo-1-(4-sulfamoyl-phenyl)-1,5-dihydro-pyrazol-4-ylidenemethyl]-furan-2-yl}-benzoic acid | 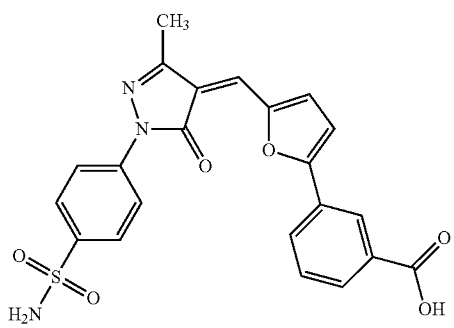 [SMILES: CC1=NN(c2ccc(S(N)(=O)=O)cc2)C(=O)/C1=C\c1ccc(-c2cccc(C(=O)O)c2)o1] | — |
| 35 | 4-(4-dimethylamino-benzylidene)-2-(3-fluoro-phenyl)-5-methyl-2,4-dihydro-pyrazol-3-one | 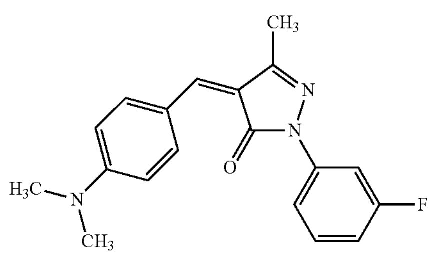 [SMILES: CC1=NN(c2cccc(F)c2)C(=O)/C1=C\c1ccc(N(C)C)cc1] | 76.31 |
| 36 | 3-{4-[4-(3-chloro-4,5-dihydro-pyrazol-1-yl)-benzylidene]-3-methyl-5-oxo-4,5-dihydro-pyrazol-1-yl}-benzoic acid | 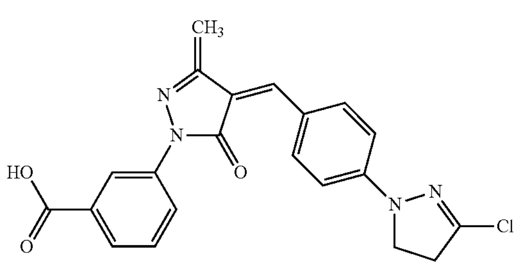 | 26.37 |

TABLE 8-continued

| No. | Chemical Name | Chemical Structure | Pentosidine Formation Ratio (%) at 5 mM Drug Concentration |
|---|---|---|---|
| 37 | 3-[4-(2-hydroxy-benzyliden)-5-oxo-3-phenyl-4,5-dihydro-pyrazol-1-yl]-benzoic acid | 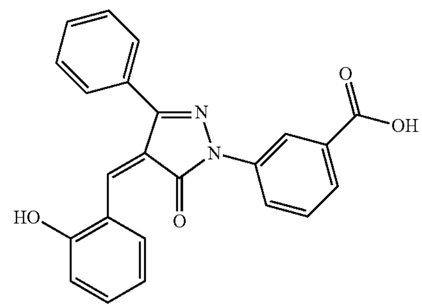 [SMILES: O=C(O)c1cccc(N2N=C(c3ccccc3)/C(=C/c3ccccc3O)C2=O)c1] | 0.02 |
| 38 | 3-[1-(3-chloro-phenyl)-3-methyl-5-oxo-1,5-dihydro-pyrazol-4-ylidenemethyl]-1H-quinolin-2-one | 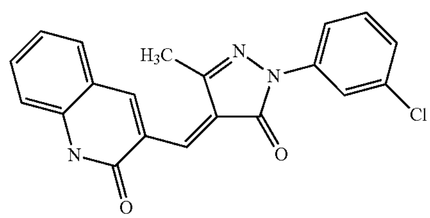 [SMILES: CC1=NN(c2cccc(Cl)c2)C(=O)/C1=C/c1cc2ccccc2[nH]c1=O] | 84.95 |

TABLE 9

| No. | Chemical Name | Chemical Structure | Pentosidine Formation Ratio (%) at 5 mM Drug Concentration |
|---|---|---|---|
| 39 | 3-{5-[3-methyl-5-oxo-1-(4-sulfamoyl-phenyl)-1,5-dihydro-pyrazol-4-ylidenemethyl]-furan-2-yl}-benzoic acid methyl ester | 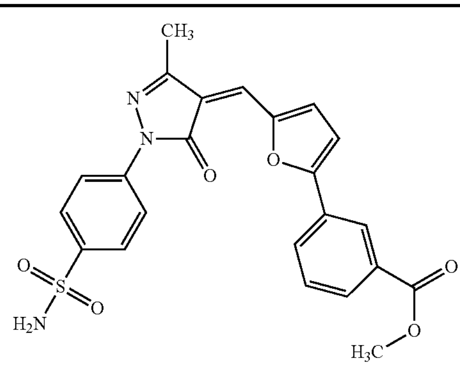 | 16.87 |
| 40 | 4-(4-benzo[1,3]dioxol-5-ylmethylene-3-methyl-5-oxo-4,5-dihydro-pyrazol-1-yl)-benzoic acid methyl ester | 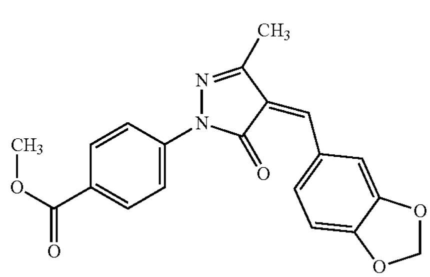 [SMILES: COC(=O)c1ccc(N2N=C(C)/C(=C/c3ccc4c(c3)OCO4)C2=O)cc1] | 32.37 |

TABLE 9-continued

| No. | Chemical Name | Chemical Structure | Pentosidine Formation Ratio (%) at 5 mM Drug Concentration |
|---|---|---|---|
| 41 | 4-{3-methyl-5-oxo-4-[5-(4-sulfamoyl-phenyl)-furan-2-ylmethylene]-4,5-dihydro-pyrazol-1-yl}-benzoic acid methyl ester | 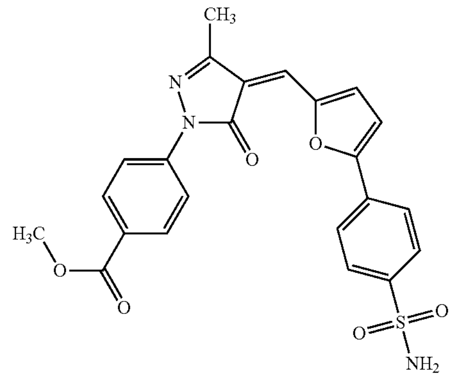 [SMILES: COC(=O)c1ccc(N2N=C(C)/C(=C/c3ccc(-c4ccc(S(N)(=O)=O)cc4)o3)C2=O)cc1] | 37.81 |
| 42 | 2-(4-chloro-phenyl)-4-(2,4-dihydroxy-benzylidene)-5-methyl-2,4-dihydro-pyrazol-3-one | 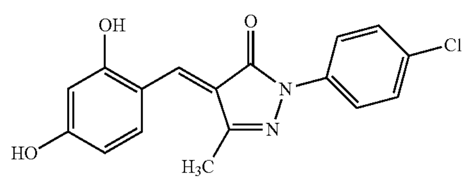 [SMILES: CC1=NN(c2ccc(Cl)cc2)C(=O)/C1=C/c1ccc(O)cc1O] | 68.32 |
| 43 | 2-(4-chloro-phenyl)-4-(3-hydroxy-benzylidene)-5-methyl-2,4-dihydropyrazol-3-one | 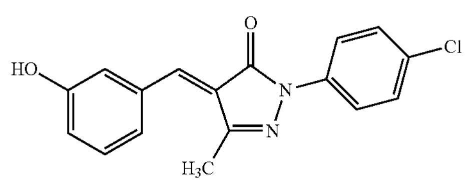 [SMILES: CC1=NN(c2ccc(Cl)cc2)C(=O)/C1=C/c1cccc(O)c1] | 3.00 |
| 44 | 4-(3,4-dihydroxy-benzylidene)-5-methyl-2-p-toluyl-2,4-dihydro-pyrazol-3-one | 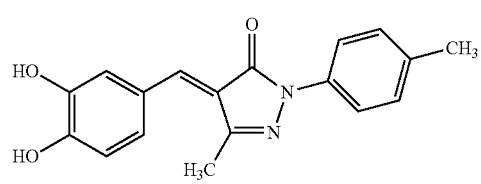 [SMILES: CC1=NN(c2ccc(C)cc2)C(=O)/C1=C/c1ccc(O)c(O)c1] | 66.19 |
| 45 | 3-[1-(4-acetyl-phenyl)-3-methyl-5-oxo-1,5-dihydro-pyrazol-4-ylidene]-1,3-dihydro-indol-2-one | 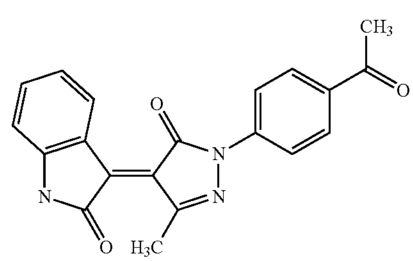 [SMILES: CC(=O)c1ccc(N2N=C(C)/C(=C3\C(=O)Nc4ccccc43)C2=O)cc1] | 19.22 |

TABLE 10

| No. | Chemical Name | Chemical Structure | Pentosidine Formation Ratio (%) at 5 mM Drug Concentration |
|---|---|---|---|
| 46 | 2-(4-fluoro-phenyl)-4-(5-hydroxy-3-methyl-1-o-toluyl-1H-pyrazol-4-ylmethylene)-5-methyl-2,4-dihydro-pyrazol-3-one | 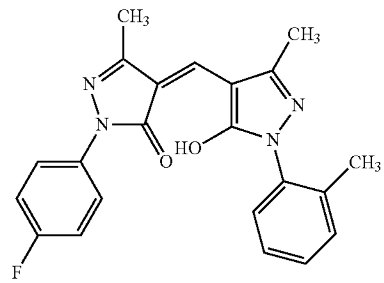 [SMILES: CC1=NN(c2ccc(F)cc2)C(=O)/C1=C\c1c(C)nn(-c2ccccc2C)c1O] | 15.69 |
| 47 | 2-(4-chloro-phenyl)-4-(4-hydroxy-3-methoxy-benzylidene)-5-trifluoromethyl-2,4-dihydro-pyrazol-3-one | 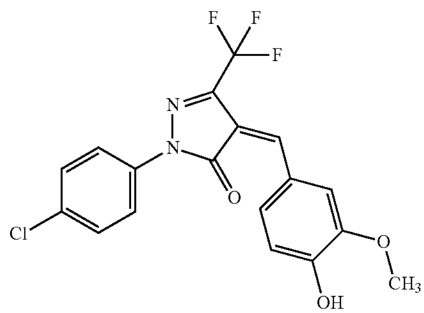 [SMILES: COc1cc(/C=C2\C(=O)N(c3ccc(Cl)cc3)N=C2C(F)(F)F)ccc1O] | 28.86 |
| 48 | 2-(4-ethyl-phenyl)-4-(4-hydroxy-benzylidene)-5-methyl-2,4-dihydro-pyrazol-3-one | 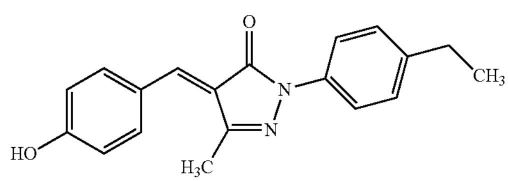 [SMILES: CCc1ccc(N2N=C(C)/C(=C\c3ccc(O)cc3)C2=O)cc1] | 0.02 |
| 49 | 4-[4-(4-hydroxy-benzylidene)-3-methyl-5-oxo-4,5-dihydro-pyrazol-1-yl]-benzenesulfonamide | 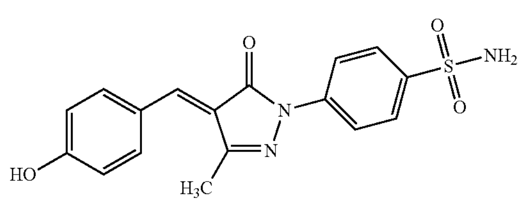 [SMILES: CC1=NN(c2ccc(S(N)(=O)=O)cc2)C(=O)/C1=C/c1ccc(O)cc1] | 7.09 |
| 50 | 4-(5-oxo-4-thiophen-2-ylmethylene-3-trifluoromethyl-4,5-dihydro-pyrazol-1-yl)-benzoic acid ethyl ester | 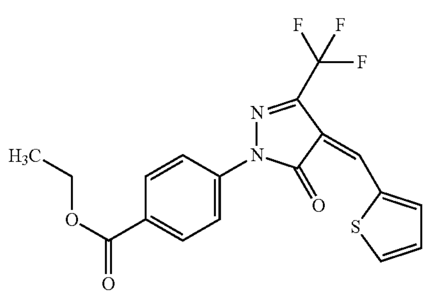 [SMILES: CCOC(=O)c1ccc(N2N=C(C(F)(F)F)/C(=C/c3cccs3)C2=O)cc1] | 63.17 |

TABLE 10-continued

| No. | Chemical Name | Chemical Structure | Pentosidine Formation Ratio (%) at 5 mM Drug Concentration |
|---|---|---|---|
| 51 | 4-[4-(4-dimethylamino-benzyliden)-5-oxo-3-trifluoromethyl-4,5-dihydro-pyrazol-1-yl]-benzenesulfonamide | 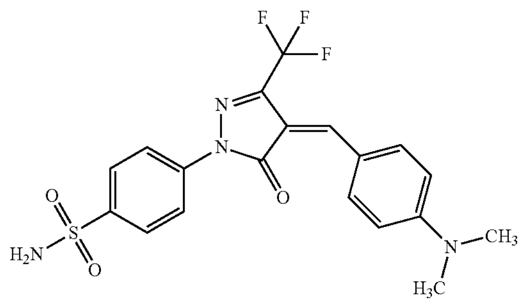 [SMILES: CN(C)c1ccc(/C=C2\C(=O)N(c3ccc(S(N)(=O)=O)cc3)N=C2C(F)(F)F)cc1] | 41.68 |
| 52 | 4-isopropylidene-5-methyl-2-phenyl-2,4-dihydro-pyrazol-3-one | 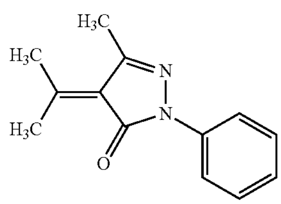 [SMILES: CC1=NN(c2ccccc2)C(=O)C1=C(C)C] | — |

TABLE 11

| No. | Chemical Name | Chemical Structure | Pentosidine Formation Ratio (%) at 5 mM Drug Concentration |
|---|---|---|---|
| 53 | 4-(4-hydroxy-benzylidene)-2-phenyl-5-trifluoromethyl-2,4-dihydro-pyrazol-3-one | 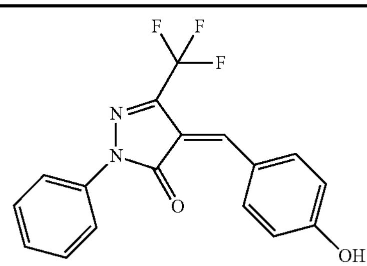 | 66.76 |
| 54 | 4-(2,4-dihydroxy-benzylidene)-2-(3,4-dimethyl-phenyl)-5-methyl-2,4-dihydro-pyrazol-3-one | 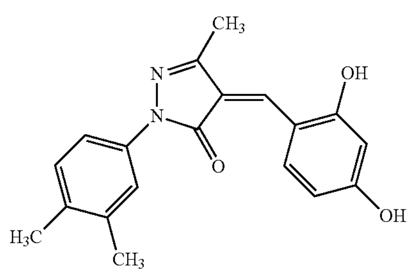 [SMILES: CC1=NN(c2ccc(C)c(C)c2)C(=O)/C1=C\c1ccc(O)cc1O] | 73.48 |
| 55 | 3-[4-(3-ethoxy-4-hydroxy-benzylidene)-3-methyl-5-oxo-4,5-dihydro-pyrazol-1-yl]-benzoic acid | 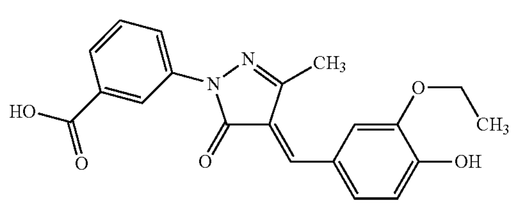 [SMILES: CCOc1cc(/C=C2/C(=O)N(c3cccc(C(=O)O)c3)N=C2C)ccc1O] | — |

TABLE 11-continued

| No. | Chemical Name | Chemical Structure | Pentosidine Formation Ratio (%) at 5 mM Drug Concentration |
|---|---|---|---|
| 56 | 4-[4-(3,5-di-tert-butyl-4-hydroxy-benzylidene)-3-methyl-5-oxo-4,5-dihydro-pyrazol-1-yl]-benzoic acid | 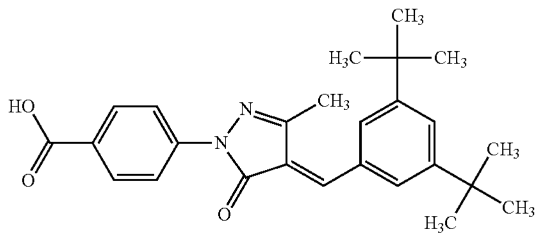 [SMILES: CC1=NN(c2ccc(C(=O)O)cc2)C(=O)/C1=C/c1cc(C(C)(C)C)cc(C(C)(C)C)c1] | — |
| 57 | 3-[3-(4-hydroxy-3-methoxy-benzylidene)-3-methyl-5-oxo-4,5-dihydro-pyrazol-1-yl]-benzoic acid | 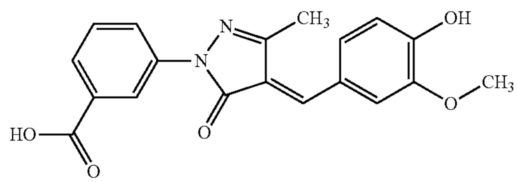 [SMILES: COc1cc(/C=C2/C(=O)N(c3cccc(C(=O)O)c3)N=C2C)ccc1O] | — |
| 58 | 3-[3-hydroxy-4-(4-hydroxy-3-methoxy-benzyliden)-5-oxo-pyrazolidin-1-yl]-benzoic acid | 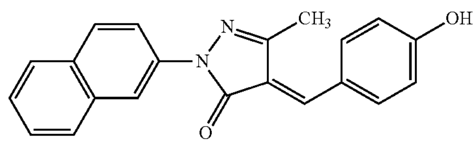 [SMILES: CC1=NN(c2ccc3ccccc3c2)C(=O)/C1=C/c1ccc(O)cc1] | 0.07 |
| 59 | 4-(3-hydroxy-2,4-dimethoxy-benzylidene)-5-methyl-2-phenyl-2,4-dihydro-pyrazol-3-one | 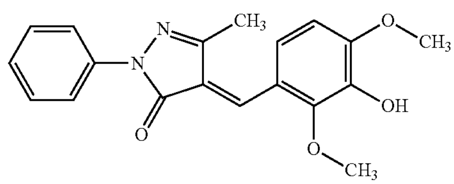 [SMILES: COc1ccc(/C=C2/C(=O)N(c3ccccc3)N=C2C)c(OC)c1O] | 5.3 |
| 60 | 4-[4-(4-hydroxy-3-methoxy-benzylidene)-3-methyl-5-oxo-pyrazolidin-1-yl]-benzoic acid isopropyl ester | 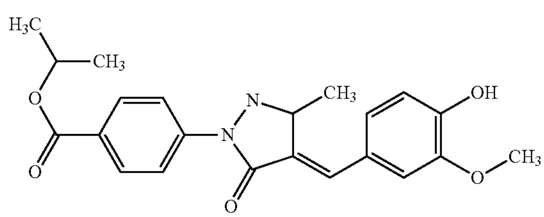 [SMILES: COc1cc(/C=C2/C(=O)N(c3ccc(C(=O)OC(C)C)cc3)NC2C)ccc1O] | 9.02 |

TABLE 12

| No. | Chemical Name | Chemical Structure | Pentosidine Formation Ratio (%) at 5 mM Drug Concentration |
|---|---|---|---|
| 61 | 2-chloro-5-[4-(2-chloro-4-hydroxy-5-methoxy-benzylidene)-3-methyl-5-oxo-4,5-dihydro-pyrazol-1-yl]-benzoic acid | 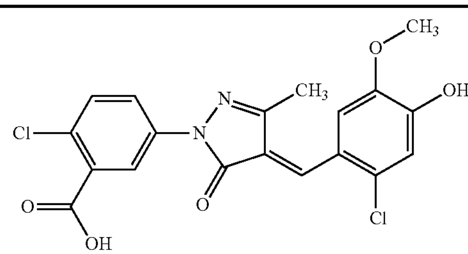 | 46.52 |

TABLE 12-continued

| No. | Chemical Name | Chemical Structure | Pentosidine Formation Ratio (%) at 5 mM Drug Concentration |
|---|---|---|---|
| 62 | 4-[4-(4-hydroxy-benzylidene)-3-methyl-5-oxo-4,5-dihydro-pyrazol-1-yl]-benzoic acid ethyl ester | 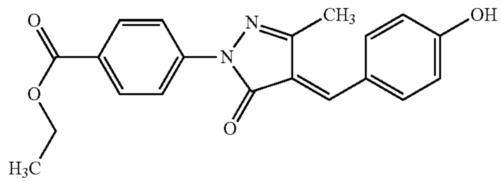 [SMILES: CCOC(=O)c1ccc(N2N=C(C)/C(=C\c3ccc(O)cc3)C2=O)cc1] | — |
| 63 | 4-[4-(4-hydroxy-benzylidene)-5-oxo-3-trifluoromethyl-4,5-dihydro-pyrazol-1-yl]-benzoic acid ethyl ester | 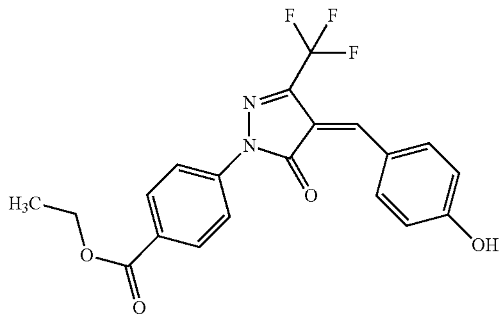 [SMILES: CCOC(=O)c1ccc(N2N=C(C(F)(F)F)/C(=C/c3ccc(O)cc3)C2=O)cc1] | — |
| 64 | 4-[4-(4-hydroxy-benzylidene)-3-methyl-5-oxo-4,5-dihydro-pyrazol-1-yl]-benzoic acid | 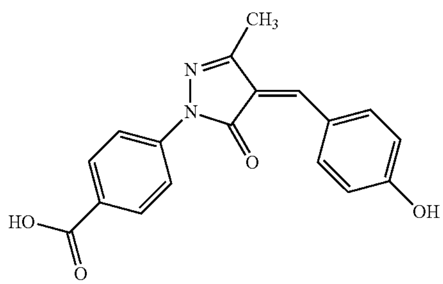 [SMILES: CC1=NN(c2ccc(C(=O)O)cc2)C(=O)/C1=C\c1ccc(O)cc1] | — |
| 65 | 4-dimethylaminomethylene-5-methyl-2-phenyl-2,4-dihydro-pyrazol-3-one | 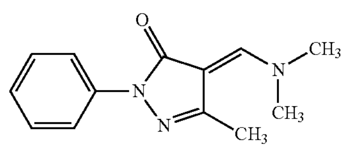 [SMILES: CC1=NN(c2ccccc2)C(=O)/C1=C/N(C)C] | 62.43 |
| 66 | 4-(5-hydroxy-3-methyl-1-phenyl-1H-pyrazol-4-ylmethylene)-5-methyl-2-phenyl-2,4-dihydro-pyrazol-3-one | 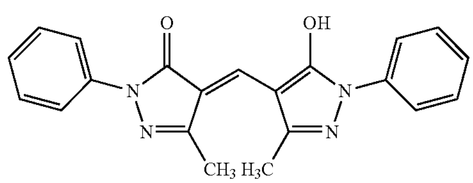 [SMILES: CC1=NN(c2ccccc2)C(=O)/C1=C/c1c(C)nn(-c2ccccc2)c1O] | 15.17 |
| 67 | 4-(4-chloro-benzylidene)-5-methyl-2-phenyl-2,4-dihydro-pyrazol-3-one | 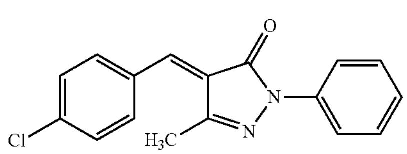 [SMILES: CC1=NN(c2ccccc2)C(=O)/C1=C/c1ccc(Cl)cc1] | 9.09 |
| 68 | 1-(5-hydroxy-3-methyl-1-phenyl-1H-pyrazol-4-yl)-6-methyl-1,3-dihydro-furo[3,4-c]pyridin-7-ol | 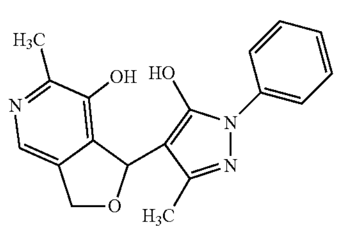 [SMILES: Cc1ncc2c(c1O)C(c1c(C)nn(-c3ccccc3)c1O)OC2] | 2.82 |

TABLE 13

| No. | Chemical Name | Chemical Structure | Pentosidine Formation Ratio (%) at 5 mM Drug Concentration |
|---|---|---|---|
| 69 | 1-(5-hydroxy-3-methyl-1-phenyl-1H-pyrazol-4-yl)-6-methyl-1,3-dihydro-furo[3,4-c]pyridin-7-ol; hydrochloric acid salt | 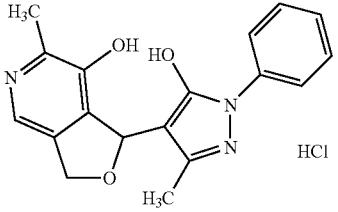 [SMILES: Cc1ncc2c(c1O)C(c1c(C)nn(-c3ccccc3)c1O)OC2 ; Cl] | 2.94 |
| 70 | 4-(4-hydroxy-benzylidene)-5-methyl-2-phenyl-2,4-dihydro-pyrazol-3-one | 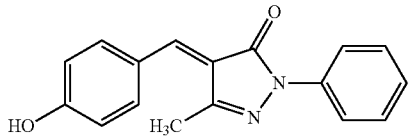 | 0.04 |
| 71 | 2-(3-chloro-phenyl)-4-(4-hydroxy-benzylidene)-5-methyl-2,4-dihydropyrazol-3-one | 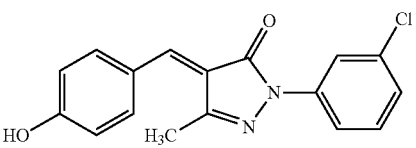 | 4.63 |
| 72 | 4-(4-benzyloxy-benzylidene)-5-methyl-2-phenyl-2,4-dihydropyrazol-3-one | 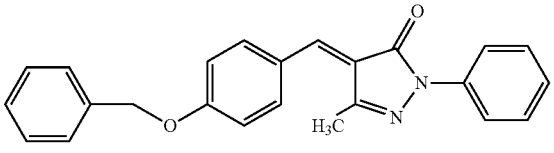 [SMILES: CC1=NN(c2ccccc2)C(=O)/C1=C/c1ccc(OCc2ccccc2)cc1] | 7.63 |
| 73 | 2-(3-chloro-phenyl)-5-methyl-2H-pyrazole-3,4-dione-4-oxime | 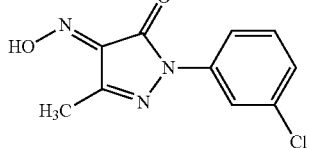 | 66.42 |
| 74 | 5-(5-oxo-1,3-diphenyl-1,5-dihydro-pyrazol-4-ylidene)-4-phenyl-4,5-dihydro-[1,3,4]thiazole-2-carboxylic acid ethyl ester | 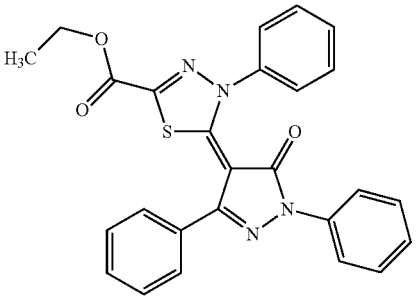 [SMILES: CCOC(=O)C1=NN(c2ccccc2)/C(=C2\C(=O)N(c3ccccc3)N=C2c2ccccc2)S1] | 87.24 |
| 75 | 4-[1,3]dithiolan-2-ylidene-5-methyl-2-phenyl-2,4-dihydro-pyrazol-3-one | 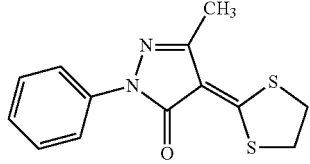 [SMILES: CC1=NN(c2ccccc2)C(=O)C1=C1SCCS1] | — |

TABLE 13-continued

| No. | Chemical Name | Chemical Structure | Pentosidine Formation Ratio (%) at 5 mM Drug Concentration |
|---|---|---|---|
| 76 | 5-(4-chloro-phenylsulfanylmethyl)-2-phenyl-4-[N'-(3-trifluoromethyl-phenyl)-hydrazino]-2,4-dihydro-pyrazol-3-one | 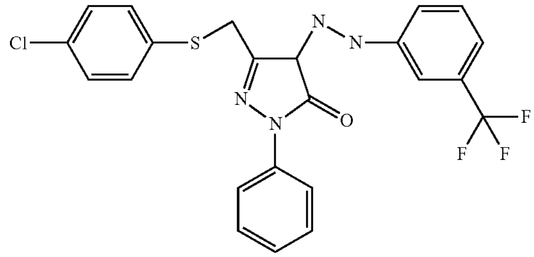 [SMILES: O=C1C(NNc2cccc(C(F)(F)F)c2)C(CSc2ccc(Cl)cc2)=NN1c1ccccc1] | — |

TABLE 14

| No. | Chemical Name | Chemical Structure | Pentosidine Formation Ratio (%) at 5 mM Drug Concentration |
|---|---|---|---|
| 77 | 4-(5-benzoyl-3-phenyl-3H-[1,3,4]thiadiazol-2-ylidene)-2,5-diphenyl-2,4-dihydro-pyrazol-3-one | 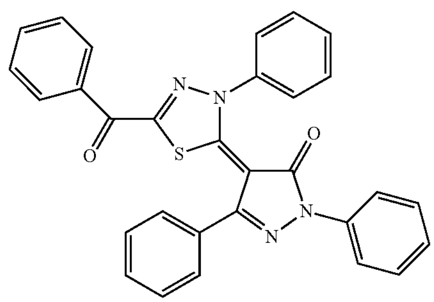 [SMILES: O=C(C1=NN(c2ccccc2)/C(=C2\C(=O)N(c3ccccc3)N=C2c2ccccc2)S1)c1ccccc1] | — |
| 78 | phosphoric acid mono-[5-hydroxy-6-methyl-4-(3-methyl-5-oxo-1-phenyl-1,5-dihydro-pyrazol-4-ylidenemethyl)-pyridin-3-ylmethyl]ester | 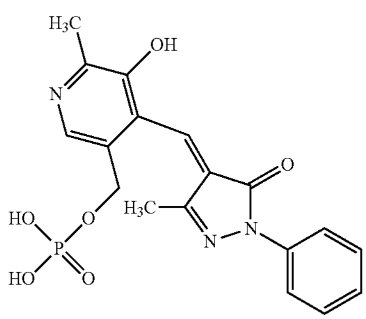 [SMILES: CC1=NN(c2ccccc2)C(=O)/C1=C/c1c(COP(=O)(O)O)cnc(C)c1O] | — |

As can be seen from these results, all Test Compounds (1) to (78) exhibited inhibitory effects on pentosidine formation.

Test Example 2

Inhibitory Effects of Phenylene Derivatives (I) on AGEs Formation

The following test compounds belonging to the phenylene derivatives represented by Formula (1) of the present invention were investigated for their inhibitory effects on AGEs formation.

(1) 3-[N-[[4-[2-(1H-tetrazol-5-yl)phenyl]phenyl]methyl]-N-pentanoylamino]benzoic acid;
(2) 3-[N-[[4-[2-(1H-tetrazol-5-yl)phenyl]phenyl]methyl]-N-acetylamino]benzoic acid;
(3) 3-[N-[[4-[2-(1H-tetrazol-5-yl)phenyl]phenyl]methyl]-N-propanoylamino]benzoic acid;
(4) 3-[N-[[4-[2-(1H-tetrazol-5-yl)phenyl]phenyl]methyl]-N-butanoylamino]benzoic acid;
(5) 3-[N-[[4-[2-(1H-tetrazol-5-yl)phenyl]phenyl]methyl]-N-octanoylamino]benzoic acid;
(6) 3-[N-[[4-[2-(1H-tetrazol-5-yl)phenyl]phenyl]methyl]-N-pentanoylamino]benzoic acid(5-methyl-2-oxo-1,3-dioxolan-4-yl)methyl;
(7) 3-[N-[[4-(1H-tetrazol-5-yl)phenyl]methyl]-N-pentanoylamino]benzoic acid;
(8) 2-[N-[[4-[2-(1H-tetrazol-5-yl)phenyl]phenyl]methyl]-N-pentanoylamino]benzoic acid;
(9) 4-[N-[[4-[2-(1H-tetrazol-5-yl)phenyl]phenyl]methyl]-N-pentanoylamino]benzoic acid;

(10) 2-oxo-3-propyl-1-[[4-[2-(1H-tetrazol-5-yl)phenyl]phenyl]methyl]-1,3,4-trihydroquinoline-7-carboxylic acid;
(11) 2-oxo-3-propyl-1-[[4-[2-(1H-tetrazol-5-yl)phenyl]phenyl]methyl]-1,3,4-trihydroquinoline-6-carboxylic acid;
(12) 2-oxo-3-propyl-1-[[4-[2-(1H-tetrazol-5-yl)phenyl]phenyl]methyl]-1,3,4-trihydroquinoline-7-carboxylic acid(5-methyl-2-oxo-1,3-dioxolan-4-yl)methyl;
(13) 1-[[4-[2-(1H-tetrazol-5-yl)phenyl]phenyl]methyl]-1,3,4-trihydroquinolin-2-one;
(14) 3-oxo-2-propyl-4-[[4-[2-(1H-tetrazol-5-yl)phenyl]phenyl]methyl]-2H-benzo[e]1,4-oxazine-6-carboxylic acid;
(15) 3-oxo-2-propyl-4-[4-[4-(1H-tetrazol-5-yl)phenyl]methyl]-2H-benzo[e]1,4-oxazine-6-carboxylic acid;
(16) 3-oxo-2-propyl-4-[[4-[2-(1H-tetrazol-5-yl)phenyl]phenyl]methyl]-2H-benzo[e]1,4-thiazine-6-carboxylic acid;
(17) 3-oxo-2-propyl-4-[[4-(1H-tetrazol-5-yl)phenyl]methyl]-2H-benzo[e]1,4-thiazine-6-carboxylic acid;
(18) 5-[4-[(2-ethyl-5,7-dimethylimidazo[4,5-b]pyridin-3-yl)methyl]phenyl]-1,3-thiazolidine-2,4-dione;
(19) 5-[4-[(5,7-dimethyl-2-propylimidazo[4,5-b]pyridin-3-yl)methyl]phenyl]-1,3-thiazolidine-2,4-dione; and
(20) 3-[N-[4-(2,4-dioxothiazolidin-5-yl)benzyl]-N-pentanoylamino]benzoic acid.

To 450 μl of protein (serum of renal failure patients with an informed consent) was added 50 μl of a solution of each test compound in dimethylsulfoxide (final concentration: 5 mM), and the resulting mixture was incubated for 1 week at 37° C. The quantity of pentosidine, which is one of the AGEs formed, was subsequently measured as follows.

First, in order to release the pentosidine formed in the protein, 50 μl of 10% trichloroacetic acid was added to 50 μl of the reacted sample, and the mixture was centrifuged to precipitate the protein that was then collected. The collected protein was washed with 300 μl of 5% trichloroacetic acid and dried; 100 μl of 6 N hydrochloric acid was subsequently added, and hydrolysis was performed for 16 hours at 110° C. The quantity of pentosidine (nmol/l) formed was measured by HPLC using a fluorescence detector (ODS C18, 4.6×250 mm, 335 nm, 385 nm), according to a gradient method (30 minutes, 1.0 ml/min) using a mobile phase of distilled water containing 0.1% trifluoroacetic acid/80% acetonitrile containing 0.08% trifluoroacetic acid (Miyata, T et al.,: J. Am. Soc., Nephrol., 7, 1198-1206, 1996; Miyata, T., et al., Proc. Natl. Acad. Sci., USA, 93 2353-2358, 1996).

In order to evaluate the inhibitory effect of each test compound on AGE formation, the proportion of the quantity of pentosidine formed was calculated as the ratio (%) of pentosidine formation relative to the quantity of pentosidine formed with a control as 100%. Further, from the calculated value, the ratio of inhibition of pentosidine formation (the ratio (%) of inhibition of AGE formation) was also determined. The results are shown in Table 15. As can be seen from these results, all Test Compounds (1) to (20) exhibited inhibitory effects on pentosidine formation.

TABLE 15

| Test Compound | Pentosidine Formation Ratio (%) | AGE Formation Inhibition Ratio (%) |
|---|---|---|
| (1) | 18.1 | 81.9 |
| (2) | 26.1 | 73.9 |
| (3) | 21.3 | 78.7 |
| (4) | 17.4 | 82.6 |
| (5) | 9.33 | 90.67 |
| (6) | 16.8 | 83.2 |
| (7) | 27.2 | 72.8 |
| (8) | 23.5 | 76.5 |

TABLE 15-continued

| Test Compound | Pentosidine Formation Ratio (%) | AGE Formation Inhibition Ratio (%) |
|---|---|---|
| (9) | 30.8 | 69.2 |
| (10) | 18.0 | 82.0 |
| (11) | 24.9 | 75.1 |
| (12) | 29.0 | 71.0 |
| (13) | 45.4 | 54.6 |
| (14) | 22.1 | 77.9 |
| (15) | 23.8 | 76.2 |
| (16) | 25.8 | 74.2 |
| (17) | 35.0 | 65.0 |
| (18) | 18.0 | 82.0 |
| (19) | 23.8 | 76.2 |
| (20) | 12.4 | 87.6 |

These test compounds were found to have inhibitory effects on AGE formation, based on the fact that pentosidine is one member of AGEs, and the phenylene derivatives (I) of the present invention inhibit the formation of pentosidine. Thus, the phenylene derivatives (I) of the present invention have inhibitory effects on AGE formation, and can be effectively used for treating or ameliorating schizophrenia.

Test Example 3

Inhibitory Effects of Phenylene Derivatives (II) on AGEs Formation

The following test compounds belonging to the phenylene derivatives represented by Formula (II) of the present invention were investigated for their inhibitory effects on AGEs formation, according to the same method used in Test Example 1.

(II-1) 3-{N-(3-phenylpropionyl)-N-[2'-(1H-tetrazol-5-yl)biphenyl-4-ylmethyl]amino}benzoic acid,
(II-6) 3-{N-pentyl-N-[4-(2,4-dioxo-1,3-thiazolidin-5-yl)benzyl]amino}benzoic acid;
(II-7) 1-[4-(2,4-dioxo-1,3-thiazolidin-5-yl)benzyl]-2-methyl-1,2,3,4-tetrahydroquinoline-7-carboxylic acid;
(II-8) 5-[4-(N-methylsulfonyl-N-phenylaminomethyl)phenyl]-1,3-thiazolidine-2,4-dione;
(II-9) 5-[4-(N-butylsulfonyl-N-phenylaminomethyl)phenyl]-1,3-thiazolidine-2,4-dione;
(II-10) 3-{N-[4-(2,4-dioxo-1,3-thiazolidin-5-yl)benzyl]-N-(methylsulfonyl)amino}benzoic acid;
(II-11) 3-{N-butylsulfonyl-N-[4-(2,4-dioxo-1,3-thiazolidin-5-yl)benzyl]amino}benzoic acid;
(II-15) 5-{4-[2-(2-pyridyl)benzimidazol-1-ylmethyl]phenyl}-1,3-thiazolidine-2,4-dione;
(II-16) 5-[4-(2-phenylimidazol-1-ylmethyl)phenyl]-1,3-thiazolidine-2,4-dione;
(II-17) 1-[4-(2,4-dioxo-1,3-thiazolidin-5-yl)benzyl]-2-oxo-3-propyl-1,2-dihydroquinoline-7-carboxylic acid;
(II-18) 3-{N-cyclohexanecarbonyl-N-[4-(2,4-dioxo-1,3-thiazolidin-5-yl)benzyl]amino}benzoic acid;
(II-19) 3-{N-[4-(2,4-dioxo-1,3-thiazolidin-5-yl)benzyl]-N-(pyridine-3-carbonyl)amino}benzoic acid;
(II-20) 3-{N-[4-(2,4-dioxo-1,3-thiazolidin-5-yl)benzyl]-N-(3-phenylpropionyl)amino}benzoic acid;
(II-21) 3-{N-(biphenyl-4-carbonyl)-N-[4-(2,4-dioxo-1,3-thiazolidin-5-yl)benzyl]amino}benzoic acid;
(II-22) 3-{N-(phenylsulfonyl)-N-[4-(2,4-dioxo-1,3-thiazolidin-5-yl)benzyl]amino}benzoic acid;
(II-23) 3-{N-(4-methylphenylsulfonyl)-N-[4-(2,4-dioxo-1,3-thiazolidin-5-yl)benzyl)amino)benzoic acid;

(II-24) 3-{N-(biphenyl-4-sulfonyl)-N-[4-(2,4-dioxo-1,3-thiazolidin-5-yl)benzyl]amino}benzoic acid;

(II-25) 3-{N-(2-naphthylsulfonyl)-N-[4-(2,4-dioxo-1,3-thiazolidin-5-yl)benzyl]amino}benzoic acid;

(II-27) 1-[4-(2,4-dioxo-1,3-thiazolidin-5-yl)benzyl]-2-oxo-3-propyl-2, 3-1H-indole-6-carboxylic acid;

(II-28) 1-[4-(2,4-dioxo-1,3-thiazolidin-5-yl)benzyl]-2-oxo-3-propyl-2,3,4,5-tetrahydro-1H-benzo[b]azepine-8-carboxylic acid;

(II-29) 3,3-dimethyl-1-[4-(2,4-dioxo-1,3-thiazolidin-5-yl)benzyl]-2-oxo-1,2,3,4-tetrahydroquinoline-7-carboxylic acid;

(II-30) 1'-[4-(2,4-dioxo-1,3-thiazolidin-5-yl)benzyl]-2'-oxo-1',4'-dihydro-2'H-spiro[cyclopropane-1,3'-quinoline]-7'-carboxylic acid;

(II-32) 3-{N-phenethyl-N-[2'-(1H-tetrazol-5-yl)biphenyl-4-ylmethyl]amino}benzoic acid;

(II-33) 3-{N-[4-(2,4-dioxo-1,3-thiazolidin-5-yl)benzyl]-N-[(5-methyl-2-phenyl-1,3-oxazol-4-yl)acetyl]amino}benzoic acid;

(II-36) 3-{N-(3-cyclohexylpropanoly)-N-[2'-(1H-tetrazol-5-yl)biphenyl-4-ylmethyl]amino}benzoic acid;

(II-42) 3-{N-(2-oxo-2-phenylethyl)-N-[2'-(1H-tetrazol-5-yl)biphenyl-4-ylmethyl]amino}benzoic acid;

(II-63) 3-{N-[4-(2,4-dioxo-1,3-thiazolidin-5-yl)benzyl]-N-[4-(2-methylthiazol-4-yl)benzenesulfonyl]amino}benzoic acid; and (II-68) 3-{N-(biphenyl-4-ylmethyl)-N-[4-(2,4-dioxo-1,3-thiazolidin-5-yl)benzyl]amino}benzoic acid.

The results are shown in Table 16. As can be seen from the results, the test compounds all showed inhibitory effects on pentosidine formation.

TABLE 16

| Test Compound | Pentosidine Formation Ratio (%) | AGE Formation Inhibition Ratio (%) |
|---|---|---|
| (II-1) | 20 | 80 |
| (II-6) | 20 | 80 |
| (II-7) | 13 | 87 |
| (II-8) | 19 | 81 |
| (II-9) | 20 | 80 |
| (II-10) | 14 | 86 |
| (II-11) | 11 | 89 |
| (II-15) | 20 | 80 |
| (II-16) | 15 | 85 |
| (II-17) | 16 | 84 |
| (II-18) | 15 | 85 |
| (II-19) | 20 | 80 |
| (II-20) | 8 | 92 |
| (II-21) | 2 | 98 |
| (II-22) | 15 | 85 |
| (II-23) | 10 | 90 |
| (II-24) | 9 | 91 |
| (II-25) | 1 | 99 |
| (II-27) | 12 | 88 |
| (II-28) | 16 | 84 |
| (II-29) | 14 | 86 |
| (II-30) | 13 | 87 |
| (II-32) | 19 | 81 |
| (II-33) | 18 | 82 |
| (II-36) | 20 | 80 |
| (II-42) | 7 | 93 |
| (II-63) | 20 | 80 |
| (II-68) | 20 | 80 |

The results show that the phenylene derivatives (II) of the present invention have inhibitory effects on AGE formation because they inhibit the formation of pentosidine. The phenylene derivatives (II) of the present invention thus have inhibitory effects on AGE formation, and can be effectively used for treating or ameliorating schizophrenia.

Preparation Example 1

Capsule

| | |
|---|---|
| Test compound* | 10 mg |
| Lactose | 100 mg |
| Corn starch | 58 mg |
| Magnesium stearate | 2 mg |
| Total: | 180 mg |

*compound (1), compound (2), phenylene derivative (I) or (II).

The ingredients listed above in powder form are mixed well, and the mixture is passed through a 60-mesh sieve (based on the Tyler Standard Screen Scale). 180 mg of the resulting powder is weighed out into each gelatin capsule (No. 3) to prepare a therapeutic or ameliorating agent for schizophrenia.

Preparation Example 2

Tablet

| | |
|---|---|
| Test compound* | 10 mg |
| Lactose | 85 mg |
| Corn starch | 34 mg |
| Microcrystalline cellulose | 10 mg |
| Magnesium stearate | 1 mg |
| Total | 150 mg |

*compound (1), compound (2), phenylene derivative (I) or (II).

The ingredients listed above in powder form are mixed well, and the mixture is compression-formed into tablets each weighing 150 mg. If necessary, these tablets may be coated with a sugar or a film. A therapeutic or ameliorating agent for schizophrenia in tablet form is thus prepared.

Preparation Example 3

Granules

| | |
|---|---|
| Test compound* | 10 mg |
| Lactose | 839 mg |
| Corn starch | 150 mg |
| Hydroxypropylcellulose | 1 mg |
| Total | 1,000 mg |

*compound (1), compound (2), phenylene derivative (I) or (II).

The ingredients listed above are mixed well, and the mixture is wetted with pure water, granulated in a basket granulator, and dried to prepare a therapeutic or ameliorating agent for schizophrenia in granular form.

BRIEF DESCRIPTION OF THE DRAWINGS

FIG. 1 shows diagnostic criteria for schizophrenia as outlined by the "International Classification of Diseases, Tenth Revision" (ICD-10) of the World Health Organization (WHO).

FIG. 2 shows diagnostic criteria for schizophrenia as outlined by the "Diagnostic and Statistical Manual, Fourth Edition" (DSM-IV) of the American Psychiatric Association (APA).

FIG. 3 is a chart listing antipsychotic drugs used for the treatment of schizophrenia.

FIGS. 5A and 5B show the results of analysis of the glyoxalase I gene for a severely schizophrenic patient (Patient A), wherein in each figure Gene M and Gene X both mean the glyoxalase I gene; and in FIG. 5A, Case 2 means the schizophrenic patient (Patient A).

FIG. 8 shows a comparison of the AGE contents in the skin according to age (under the age of 50, or over the age of 50) between healthy subjects (n=24) and schizophrenic patients (n=24) (Example 2).

FIG. 12 shows a summary of the measured results for glyoxalase I activity (mUnit/$10^6$ RBC), pentosidine activity (pmol/mg protein), blood vitamin $B_6$ contents (ng/ml) (pyridoxal, pyridoxamine, and pyridoxine), blood vitamin B12 content (pg/ml), blood folate content (ng/ml), blood homocysteine content (nmol/ml), creatinine content (mg/dl), and eGFR (ml/min/1.73 $m^2$) on schizophrenic patients of various types (i.e., the frameshift type [n=2], homozygous-type Ala/Ala [n=5], heterozygous-type Glu/Ala [n=1]), and healthy subjects (homozygous-type Glu/Glu) [n=7].

SEQUENCE LISTING FREE TEXT

Figure 4:
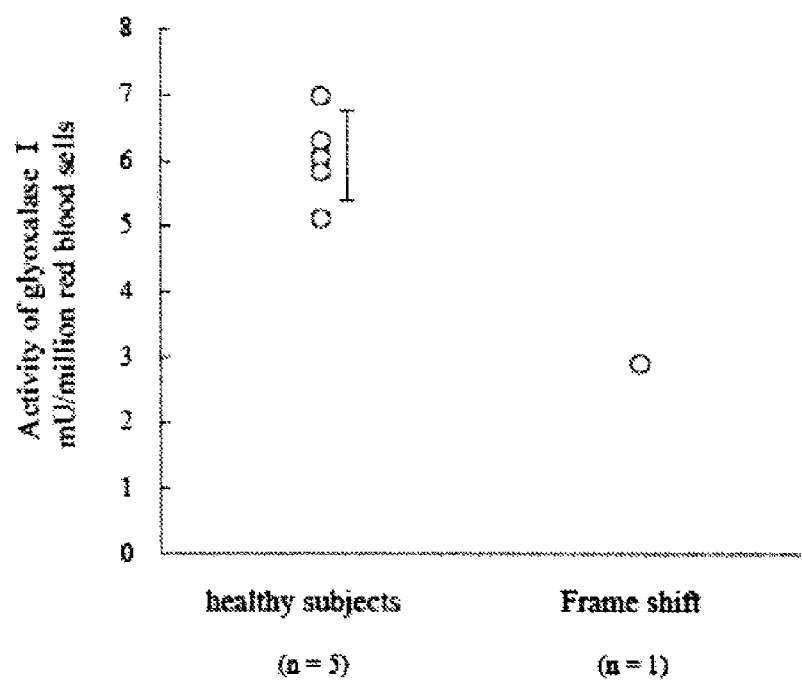
FIG. 4 is a graph showing a comparison of the erythrocyte glyoxalase activities between a severely schizophrenic patient (n=1) and healthy subjects (n=5) (Example 1).
Figure 6:
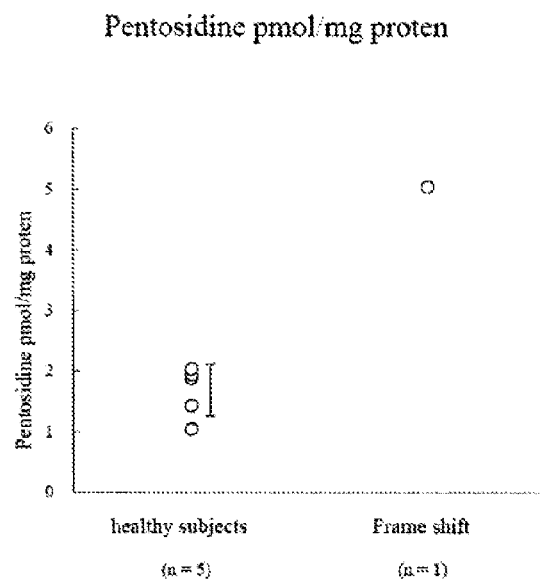
FIG. 6 is a graph showing a comparison of the serum AGE levels (the quantities of pentosidine) between a severely schizophrenic patient (n=1) and healthy subjects (n=5) (Example 1).
Figure 7:
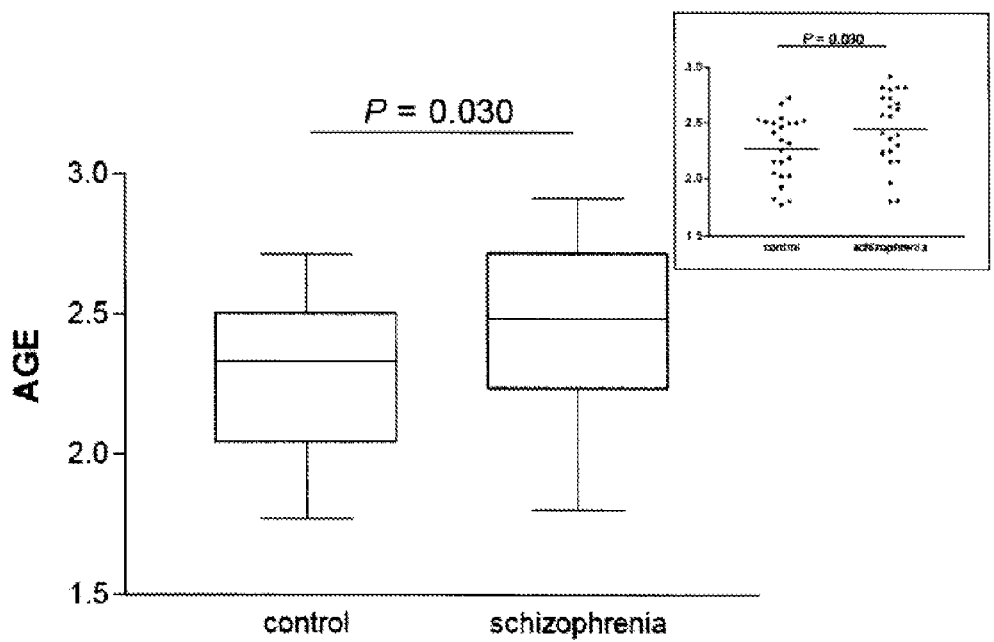
FIG. 7 is a graph showing a comparison of the AGE contents in the skin between the healthy subjects (n=24, male: 12, female: 12, average age: 48.88±3.17 years) and schizophrenic patients (n=24, male: 12, female: 12, average age: 48.38±2.23 years) (Example 2).
Figure 9:
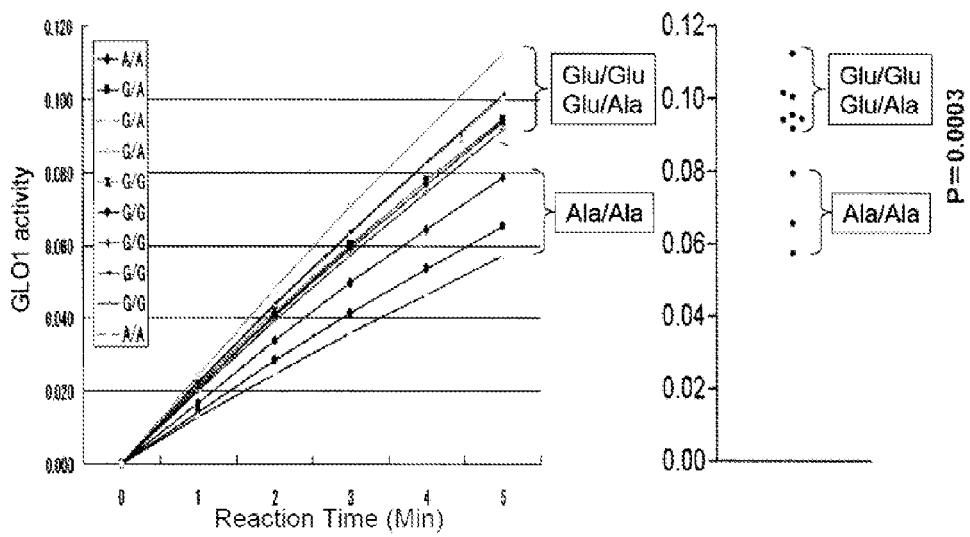
FIG. 9 is a graph showing the erythrocyte glyoxalase activities measured for schizophrenic patients with Ala/Ala homozygotes, schizophrenic patients with Glu/Ala heterozygotes and Glu/Glu homozygotes, and healthy subjects (Example 3).
Figure 10:
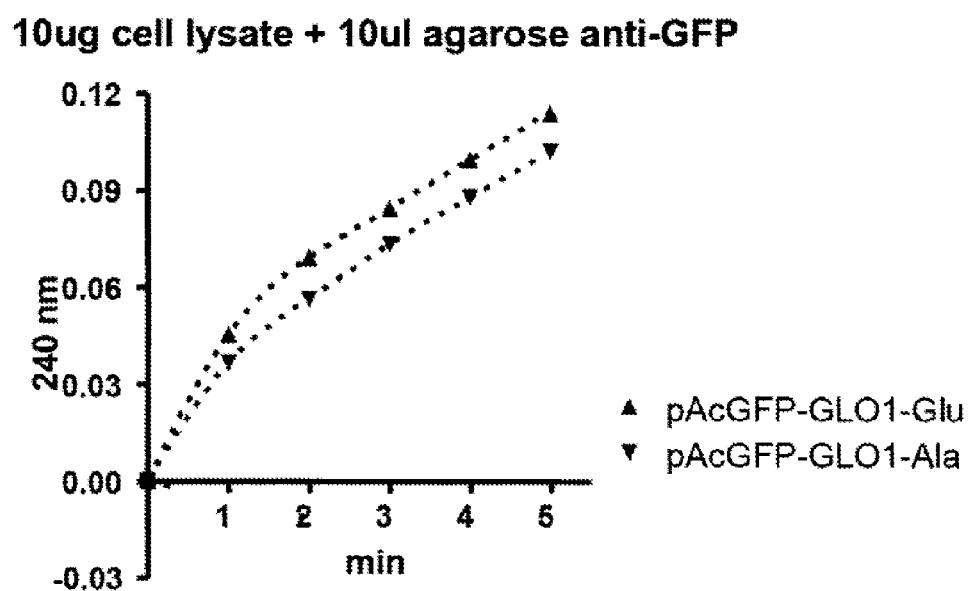
FIG. 10 is a graph showing the GLO-I activities measured by expressing in COS cells each of a construct (pAcGFP-GLO1-Ala) consisting of GFP and mutant GLO-I having an Ala at position 111; and a construct (pAcGFP-GLO1-Glu) consisting of GFP and normal GLO-I having a Glu at position 111 (Example 3).
Figure 11:
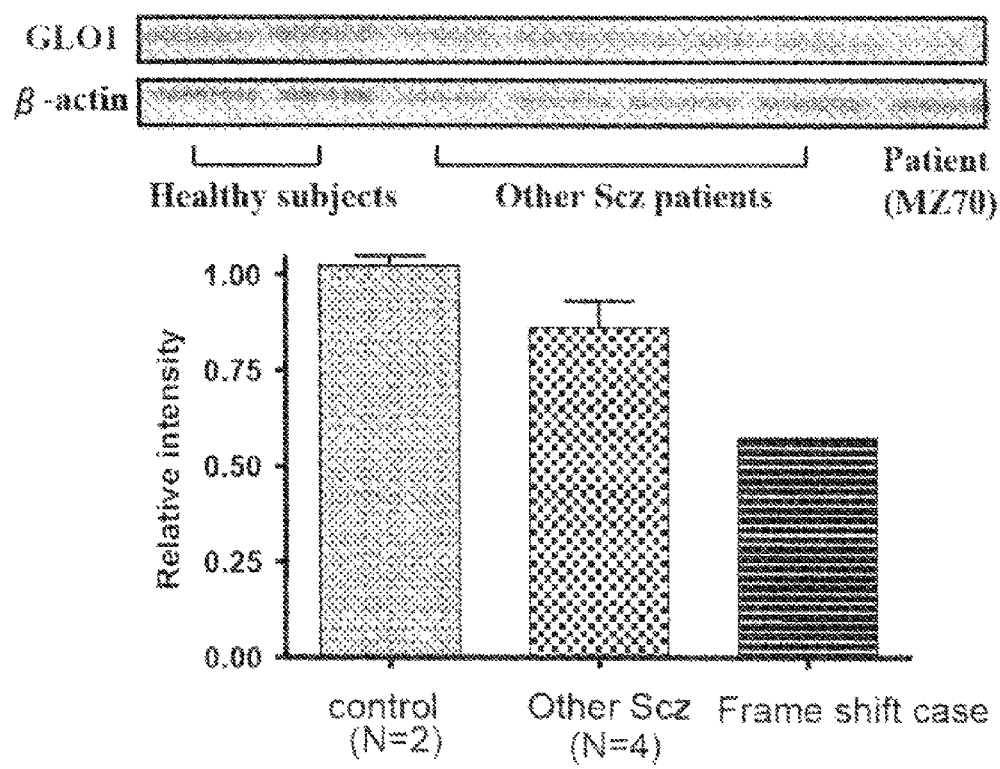
FIG. 11 shows the levels of mRNA expression of glyoxalase I measured for schizophrenic patients with Ala/Ala homozygotes (n=4) and severely schizophrenic Patient A (glyoxalase I-deficient due to a frameshift).
Figure 13:
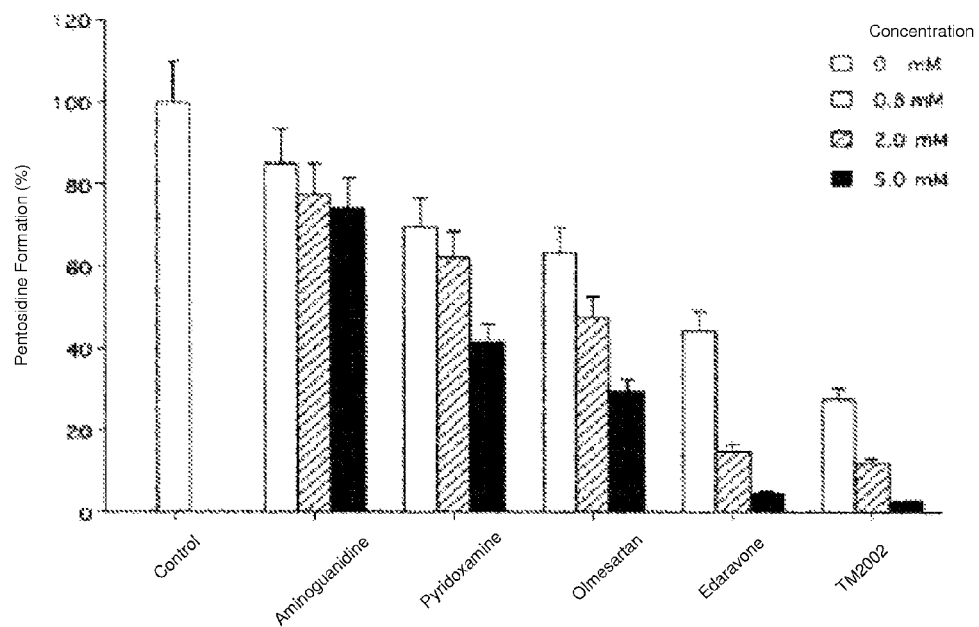
FIG. 13 shows the inhibitory effects on pentosidine formation investigated for aminoguanidine, pyridoxamine, olmesartan, edaravone, and TM2002 (Test Example 1 (2)).

SEQ ID NO: 4 shows a base sequence of a region from positions 1 to 200 upstream of adenine at position 201 of the base sequence (SEQ ID NO: 1) of the glyoxalase I (GLO-I) gene (corresponding to position 79 of the base sequence (SEQ ID NO: 2) of the coding region).

SEQ ID NO: 5 shows a base sequence of a region from positions 203 to 502 downstream of cytosine at position 202 of the base sequence (SEQ ID NO: 1) of the GLO-I gene (corresponding to position 80 of the base sequence (SEQ ID NO: 2) of the coding region).

SEQ ID NO: 6 shows a base sequence of a region from positions 154 to 453 upstream of adenine at position 454 of the base sequence (SEQ ID NO: 1) of the GLO-I gene (corresponding to position 332 of the base sequence (SEQ ID NO: 2) of the coding region).

SEQ ID NO: 7 shows a base sequence of a region from positions 455 to 754 downstream of adenine at position 454 of the base sequence (SEQ ID NO: 1) of the GLO-I gene (corresponding to position 332 of the base sequence (SEQ ID NO: 2) of the coding region).

SEQ ID NO: 8 shows a base sequence of a forward primer used in PCT-direct sequencing for detecting an insertion mutation between positions 79 and 80 of the base sequence (SEQ ID NO: 2) of the coding region of the GLO-I gene.

SEQ ID NO: 9 shows a base sequence of a reverse primer used in PCT-direct sequencing for detecting an insertion mutation between positions 79 and 80 of the base sequence (SEQ ID NO: 2) of the coding region of the GLO-I gene.

SEQ ID No. 10 shows a base sequence of a forward primer used in PCT-direct sequencing for detecting a base substitution mutation at position 332 of the base sequence (SEQ ID NO: 2) of the coding region of the GLO-I gene.

SEQ ID NO: 11 shows a base sequence of a reverse primer used in PCT-direct sequencing for detecting a base substitution mutation at position 332 of the base sequence (SEQ ID NO: 2) of the coding region of the GLO-I gene.

The invention claimed is:

1. A method for treating or ameliorating schizophrenia in a warm-blooded animal having schizophrenia, comprising administering a preparation comprising a pharmaceutically effective amount of pyridoxamine, or a pharmaceutically acceptable salt or ester thereof having a carbonyl scavenger effect, as an active ingredient to the warm-blooded animal having schizophrenia.

2. The method according to claim 1, wherein the warm-blooded animal is a patient diagnosed as having schizophrenia.

3. The method according to claim 2, wherein the patient is one having abnormality in detoxification of an advanced Glycation End product precursor.

4. The method according to claim 3, wherein the abnormality in detoxification of an advanced Glycation End product precursor is due to lowered glyoxalase I activity in the patient.

5. The method according to claim 2, wherein the patient is one having a genetic abnormality of glyoxalase I activity that lowers glyoxalase I activity.

6. The method according to claim 1, wherein administration to the warm-blooded animal is by an oral route, an intravenous route, an intramuscular route, an intradermal route, an subcutaneous route, an intraperitoneal route or an intrarectal route.

7. A method for treating or ameliorating schizophrenia in a warm-blooded animal having schizophrenia, comprising administering a preparation containing a pharmaceutically effective amount of pyridoxamine, or a pharmaceutically acceptable salt or ester thereof having a carbonyl scavenger effect, as the sole active ingredient for ameliorating schizophrenia to the warm-blooded animal having schizophrenia.

8. The method according to claim 7, wherein the warm-blooded animal is a patient diagnosed as having schizophrenia.

9. The method according to claim 8, wherein the patient is one having abnormality in detoxification of an advanced Glycation End product precursor.

10. The method according to claim 9, wherein the abnormality in detoxification of an advanced Glycation End product precursor is due to lowered glyoxalase I activity in the patient.

11. The method according to claim 10, wherein the patient is one having a genetic abnormality of glyoxalase I activity that lowers glyoxalase I activity.

12. The method according to claim 7, which is administered to the warm-blooded animal by the oral route, the intravenous route, the intramuscular route, the intradermal route, the subcutaneous route, the intraperitoneal route, or the intrarectal route.

* * * * *